(12) United States Patent
Babkin et al.

(10) Patent No.: US 11,564,725 B2
(45) Date of Patent: Jan. 31, 2023

(54) ABLATION CATHETER HAVING A SHAPE MEMORY STYLET

(71) Applicant: ADAGIO MEDICAL, INC., Laguna Hills, CA (US)

(72) Inventors: Alexei Babkin, Dana Point, CA (US); Pedram Nourian, Tustin, CA (US); Meital Mazor, Laguna Hills, CA (US); Faysal S. Ahmed, Irvine, CA (US); David Cabrita, Brussels (BE)

(73) Assignee: Adagio Medical, Inc., Laguna Hills, CA (US)

( * ) Notice: Subject to any disclaimer, the term of this patent is extended or adjusted under 35 U.S.C. 154(b) by 491 days.

(21) Appl. No.: 16/121,791

(22) Filed: Sep. 5, 2018

(65) Prior Publication Data

US 2019/0076179 A1    Mar. 14, 2019

Related U.S. Application Data

(60) Provisional application No. 62/669,039, filed on May 9, 2018, provisional application No. 62/575,998, filed
(Continued)

(51) Int. Cl.
*A61B 18/02* (2006.01)
*A61B 18/14* (2006.01)
(Continued)

(52) U.S. Cl.
CPC .......... *A61B 18/02* (2013.01); *A61B 18/1477* (2013.01); *A61B 18/1492* (2013.01);
(Continued)

(58) Field of Classification Search
CPC . A61B 18/02; A61B 18/1477; A61B 18/1492; A61B 2018/00166;
(Continued)

(56) References Cited

U.S. PATENT DOCUMENTS 3,062,017 A    11/1962    Balcar et al.
3,613,689 A    10/1971    Crump et al.
(Continued)

FOREIGN PATENT DOCUMENTS

GB    1422535 A    1/1976
GB    2283678 A    5/1995
(Continued)

OTHER PUBLICATIONS

International Search Report dated Dec. 28, 2016 for PCT/US2016/33833.
(Continued)

*Primary Examiner* — Daniel W Fowler
(74) *Attorney, Agent, or Firm* — Richard Batt

(57) ABSTRACT

An ablation apparatus for creating a lesion in target tissue, the ablation apparatus having an ablation shaft including a handle, a first portion, an ablation portion, distal tip, at least one ablation energy delivery lumen, at least one ablation energy return lumen, and a stylet lumen that extends substantially along a length of the ablation shaft from the handle to at least the ablation portion. The ablation apparatus also includes a stylet that is capable of being inserted into the stylet lumen where the stylet is made of a shape-memory material.

16 Claims, 43 Drawing Sheets

Related U.S. Application Data on Oct. 23, 2017, provisional application No. 62/554,483, filed on Sep. 5, 2017.

(51) Int. Cl.
*A61B 18/00* (2006.01)
*A61B 17/00* (2006.01)

(52) U.S. Cl.
CPC ........... *A61B 2017/00243* (2013.01); *A61B 2017/00867* (2013.01); *A61B 2018/00166* (2013.01); *A61B 2018/00214* (2013.01); *A61B 2018/00351* (2013.01); *A61B 2018/00577* (2013.01); *A61B 2018/00625* (2013.01); *A61B 2018/00702* (2013.01); *A61B 2018/00791* (2013.01); *A61B 2018/0212* (2013.01); *A61B 2018/0262* (2013.01); *A61B 2018/0287* (2013.01); *A61B 2018/1407* (2013.01); *A61B 2018/1435* (2013.01)

(58) Field of Classification Search
CPC ........... A61B 2018/00214; A61B 2018/00351; A61B 2018/00577; A61B 2018/00625; A61B 2018/00702; A61B 2018/00791; A61B 2018/00212; A61B 2018/0262
See application file for complete search history.

(56) References Cited

U.S. PATENT DOCUMENTS

| | | |
|---|---|---|
| 3,889,680 A | 6/1975 | Armao |
| 3,942,010 A | 3/1976 | Peterson et al. |
| 3,993,123 A | 11/1976 | Chu et al. |
| 4,034,251 A | 7/1977 | Haas |
| 4,167,771 A | 9/1979 | Simons |
| 4,226,281 A | 10/1980 | Chu |
| 4,281,268 A | 7/1981 | Sawa et al. |
| 4,384,360 A | 5/1983 | Kitadate et al. |
| 4,418,421 A | 11/1983 | Kitadate et al. |
| 4,519,389 A | 5/1985 | Gudkin et al. |
| 4,548,045 A | 10/1985 | Altares et al. |
| 4,802,475 A | 2/1989 | Weshahy |
| 4,838,041 A | 6/1989 | Bellows et al. |
| 4,843,446 A | 6/1989 | Nishino et al. |
| 4,945,562 A | 7/1990 | Staub |
| 4,946,460 A | 8/1990 | Merry et al. |
| 4,982,080 A | 1/1991 | Wilson et al. |
| 5,012,505 A | 4/1991 | Zupancic et al. |
| 5,037,395 A | 8/1991 | Spencer |
| 5,108,390 A | 4/1992 | Potocky et al. |
| 5,147,355 A | 9/1992 | Friedman et al. |
| 5,147,538 A | 9/1992 | Wright et al. |
| 5,155,093 A | 10/1992 | Den et al. |
| 5,173,606 A | 12/1992 | Weinberger et al. |
| 5,211,646 A | 5/1993 | Alperovich et al. |
| 5,212,626 A | 5/1993 | Bell et al. |
| 5,214,925 A | 6/1993 | Hoy et al. |
| 5,237,824 A | 8/1993 | Pawliszyn |
| 5,254,116 A | 10/1993 | Baust et al. |
| 5,274,237 A | 12/1993 | Gallagher et al. |
| RE34,502 E | 1/1994 | Webster, Jr. |
| 5,275,595 A | 1/1994 | Dobak |
| 5,324,286 A | 6/1994 | Fowle |
| 5,334,181 A | 8/1994 | Rubinsky et al. |
| 5,369,384 A | 11/1994 | Heins |
| 5,400,602 A | 3/1995 | Chang et al. |
| 5,405,533 A | 4/1995 | Hazlebeck et al. |
| 5,417,072 A | 5/1995 | Silver et al. |
| 5,433,717 A | 7/1995 | Rubinsky et al. |
| 5,452,582 A | 9/1995 | Longsworth |
| 5,471,844 A | 12/1995 | Levi |
| 5,494,039 A | 2/1996 | Onik et al. |
| 5,504,924 A | 4/1996 | Ohashi et al. |
| 5,520,682 A | 5/1996 | Baust et al. |
| 5,531,742 A | 7/1996 | Barken |
| 5,573,532 A | 11/1996 | Chang et al. |
| 5,603,221 A | 2/1997 | Maytal |
| 5,661,980 A | 9/1997 | Gallivan |
| 5,702,435 A | 12/1997 | Maytal |
| 5,716,353 A | 2/1998 | Matsuura et al. |
| 5,733,280 A | 3/1998 | Avitall |
| 5,741,248 A | 4/1998 | Stern et al. |
| 5,757,885 A | 5/1998 | Yao et al. |
| 5,800,487 A | 9/1998 | Mikus et al. |
| 5,800,488 A | 9/1998 | Crockett |
| 5,816,052 A | 10/1998 | Foote et al. |
| 5,885,276 A | 3/1999 | Ammar et al. |
| 5,899,897 A | 5/1999 | Rabin et al. |
| 5,899,898 A | 5/1999 | Arless et al. |
| 5,899,899 A | 5/1999 | Arless et al. |
| 5,901,783 A | 5/1999 | Dobak et al. |
| 5,910,104 A | 6/1999 | Dobak et al. |
| 5,916,212 A | 6/1999 | Baust et al. |
| 5,924,975 A | 7/1999 | Goldowsky |
| 5,947,960 A | 9/1999 | Griswold |
| 5,950,444 A | 9/1999 | Matsunaga |
| 5,954,714 A | 9/1999 | Saadat et al. |
| 5,957,963 A | 9/1999 | Dobak |
| 5,978,697 A | 11/1999 | Maytal et al. |
| 5,993,444 A | 11/1999 | Ammar et al. |
| 5,997,781 A | 12/1999 | Nishikawa et al. |
| 6,004,269 A | 12/1999 | Crowley et al. |
| 6,039,730 A | 3/2000 | Rabin et al. |
| 6,074,412 A | 6/2000 | Mikus et al. |
| 6,096,068 A | 8/2000 | Dobak et al. |
| 6,106,518 A | 8/2000 | Wittenberger et al. |
| 6,123,699 A | 9/2000 | Webster, Jr. |
| 6,129,704 A | 10/2000 | Forman et al. |
| 6,139,544 A | 10/2000 | Mikus et al. |
| 6,142,991 A | 11/2000 | Schatzberger |
| 6,161,543 A | 12/2000 | Cox et al. |
| 6,171,277 B1 | 1/2001 | Ponzi |
| 6,179,831 B1 | 1/2001 | Bliweis |
| 6,182,666 B1 | 2/2001 | Dobak |
| 6,190,378 B1 | 2/2001 | Jarvinen |
| 6,190,382 B1 | 2/2001 | Ormsby et al. |
| 6,193,644 B1 | 2/2001 | Dobak et al. |
| 6,198,974 B1 | 3/2001 | Webster, Jr. |
| 6,235,018 B1 | 5/2001 | LePivert |
| 6,237,355 B1 | 5/2001 | Li |
| 6,241,722 B1 | 6/2001 | Dobak et al. |
| 6,251,105 B1 | 6/2001 | Mikus et al. |
| 6,263,046 B1 | 7/2001 | Rogers |
| 6,270,493 B1 | 8/2001 | Lalonde et al. |
| 6,307,916 B1 | 10/2001 | Rogers et al. |
| 6,324,852 B1 | 12/2001 | Cheng |
| 6,341,629 B1 | 1/2002 | Clark et al. |
| 6,347,675 B1 | 2/2002 | Kollé |
| 6,355,029 B1 | 3/2002 | Joye et al. |
| 6,368,304 B1 | 4/2002 | Aliberto et al. |
| 6,377,659 B1 | 4/2002 | Snyder et al. |
| 6,396,901 B1 | 5/2002 | Hell et al. |
| 6,432,174 B1 | 8/2002 | Heung |
| 6,440,126 B1 | 8/2002 | Abboud et al. |
| 6,451,011 B2 | 9/2002 | Tu |
| 6,471,694 B1 | 10/2002 | Kudaravalli et al. |
| 6,475,212 B2 | 11/2002 | Dobak et al. |
| 6,477,231 B2 | 11/2002 | Snyder et al. |
| 6,486,078 B1 | 11/2002 | Rangarajan et al. |
| 6,520,933 B1 | 2/2003 | Evans et al. |
| 6,527,765 B2 | 3/2003 | Kelman et al. |
| 6,530,420 B1 | 3/2003 | Takada et al. |
| 6,537,271 B1 | 3/2003 | Murray et al. |
| 6,544,176 B2 | 4/2003 | Mikus et al. |
| 6,551,309 B1 | 4/2003 | LePivert |
| 6,554,797 B1 | 4/2003 | Worthen |
| 6,572,610 B2 | 6/2003 | Kovalcheck et al. |
| 6,584,332 B2 | 6/2003 | Yoshitake et al. |
| 6,592,581 B2 | 7/2003 | Bowe |
| 6,602,276 B2 | 8/2003 | Dobak et al. |
| 6,613,046 B1 | 9/2003 | Jenkins et al. |
| 6,622,494 B1 | 9/2003 | Pourrahimi |
| 6,622,507 B2 | 9/2003 | Cotte et al. |

(56) References Cited

U.S. PATENT DOCUMENTS

| | | |
|---|---|---|
| 6,628,002 B2 | 9/2003 | Ritz et al. |
| 6,648,879 B2 | 11/2003 | Joye et al. |
| 6,685,720 B1 | 2/2004 | Wu et al. |
| 6,706,037 B2 | 3/2004 | Zvuloni et al. |
| 6,726,653 B2 | 4/2004 | Noda et al. |
| 6,737,225 B2 | 5/2004 | Miller |
| 6,746,445 B2 | 6/2004 | Abboud et al. |
| 6,767,346 B2 | 7/2004 | Damasco et al. |
| 6,771,996 B2 | 8/2004 | Bowe et al. |
| 6,776,765 B2 | 8/2004 | Soukup et al. |
| 6,812,464 B1 | 11/2004 | Sobolewski et al. |
| 6,848,458 B1 | 2/2005 | Shrinivasan et al. |
| 6,848,502 B2 | 2/2005 | Bishop et al. |
| 6,893,419 B2 | 5/2005 | Noda et al. |
| 6,893,433 B2 | 5/2005 | Lentz |
| 6,905,492 B2 | 6/2005 | Zvuloni et al. |
| 6,905,493 B2 | 6/2005 | Lentz |
| 6,936,045 B2 | 8/2005 | Yu et al. |
| 6,941,953 B2 | 9/2005 | Feld et al. |
| 6,984,230 B2 | 1/2006 | Scheller et al. |
| 6,989,009 B2 | 1/2006 | Lafontaine |
| 7,004,937 B2 | 2/2006 | Lentz et al. |
| 7,013,170 B2 | 3/2006 | Bowe |
| 7,022,120 B2 | 4/2006 | Lafontaine |
| 7,083,612 B2 | 8/2006 | Littrup et al. |
| 7,110,506 B2 | 9/2006 | Radley et al. |
| 7,160,290 B2 | 1/2007 | Eberl et al. |
| 7,195,625 B2 | 3/2007 | Lentz |
| 7,220,252 B2 | 5/2007 | Shah |
| 7,220,257 B1 | 5/2007 | Lafontaine |
| 7,258,161 B2 | 8/2007 | Cosley et al. |
| 7,273,479 B2 | 9/2007 | Littrup et al. |
| 7,410,484 B2 | 8/2008 | Littrup et al. |
| 7,507,233 B2 | 3/2009 | Littrup et al. |
| 7,648,497 B2 | 1/2010 | Lane et al. |
| 7,740,627 B2 | 6/2010 | Gammie et al. |
| 7,758,571 B2 | 7/2010 | Saadat |
| 7,842,031 B2 | 11/2010 | Abboud et al. |
| 7,921,657 B2 | 4/2011 | Littrup et al. |
| 8,012,147 B2 | 9/2011 | Lafontaine |
| 8,177,780 B2 | 5/2012 | Cox et al. |
| 8,298,217 B2 | 10/2012 | Lane et al. |
| 8,387,402 B2 | 3/2013 | Littrup et al. |
| 8,475,441 B2 | 7/2013 | Babkin et al. |
| 8,491,520 B2 | 7/2013 | Smith et al. |
| 8,591,503 B2 | 11/2013 | Littrup et al. |
| 8,641,704 B2 | 2/2014 | Werneth et al. |
| 8,679,104 B2 | 3/2014 | Abboud et al. |
| 8,685,014 B2 | 4/2014 | Babkin et al. |
| 8,740,891 B2 | 6/2014 | Babkin et al. |
| 8,740,892 B2 | 6/2014 | Babkin et al. |
| 8,845,628 B2 | 9/2014 | Babkin et al. |
| 8,888,768 B2 | 11/2014 | Babkin et al. |
| 8,945,106 B2 | 2/2015 | Arless et al. |
| 9,095,320 B2 | 8/2015 | Littrup et al. |
| 9,155,476 B2 | 10/2015 | Fojtik |
| 9,408,656 B2 | 8/2016 | Littrup et al. |
| 9,480,521 B2 | 11/2016 | Kim et al. |
| 10,159,521 B2 | 12/2018 | Jannicke et al. |
| 10,182,742 B2 | 1/2019 | Condie et al. |
| 10,194,978 B2 | 2/2019 | Coulombe |
| 10,271,899 B2 | 4/2019 | Deac |
| 10,405,919 B2 | 9/2019 | Fung et al. |
| 10,575,156 B2 | 2/2020 | Shedletsky et al. |
| 2001/0024485 A1 | 9/2001 | Rogers |
| 2001/0037812 A1 | 11/2001 | Dobak et al. |
| 2001/0047134 A1 | 11/2001 | Holdaway et al. |
| 2002/0007180 A1 | 1/2002 | Wittenberger et al. |
| 2002/0049409 A1 | 4/2002 | Noda et al. |
| 2002/0062831 A1 | 5/2002 | Beyar et al. |
| 2002/0072741 A1 | 6/2002 | Sliwa et al. |
| 2002/0087152 A1 | 7/2002 | Mikus et al. |
| 2002/0151331 A1 | 10/2002 | Abdelmonem et al. |
| 2002/0151880 A1* | 10/2002 | Lafontaine ............ A61B 18/02 606/21 |
| 2003/0040740 A1 | 2/2003 | Kovalcheck et al. |
| 2003/0055415 A1 | 3/2003 | Yu et al. |
| 2003/0065371 A1 | 4/2003 | Satake |
| 2003/0088240 A1 | 5/2003 | Saadat |
| 2003/0195605 A1 | 10/2003 | Kovalcheck et al. |
| 2003/0199817 A1 | 10/2003 | Thompson et al. |
| 2004/0027462 A1 | 2/2004 | Hing |
| 2004/0044334 A1 | 3/2004 | Lafontaine |
| 2004/0082948 A1* | 4/2004 | Stewart ............ A61B 18/1492 606/41 |
| 2004/0118144 A1 | 6/2004 | Hsu et al. |
| 2004/0148004 A1 | 7/2004 | Wallsten |
| 2004/0215294 A1 | 10/2004 | Littrup et al. |
| 2004/0215295 A1 | 10/2004 | Littrup et al. |
| 2005/0027247 A1 | 2/2005 | Carrison et al. |
| 2005/0027289 A1 | 2/2005 | Castellano et al. |
| 2005/0049345 A1 | 3/2005 | Greiner et al. |
| 2005/0101903 A1 | 5/2005 | Kohler et al. |
| 2005/0107678 A1* | 5/2005 | Bowe ................ A61B 18/1492 600/374 |
| 2005/0209587 A1 | 9/2005 | Joye et al. |
| 2005/0261573 A1 | 11/2005 | Satoh et al. |
| 2005/0283146 A1* | 12/2005 | Lentz .................... A61B 18/02 606/23 |
| 2006/0212028 A1 | 9/2006 | Joye et al. |
| 2006/0235357 A1 | 10/2006 | Woodward et al. |
| 2006/0235375 A1 | 10/2006 | Littrup et al. |
| 2006/0247611 A1 | 11/2006 | Abboud et al. |
| 2006/0253114 A1 | 11/2006 | Saadat |
| 2008/0119836 A1 | 5/2008 | Littrup et al. |
| 2008/0312644 A1 | 12/2008 | Fourkas et al. |
| 2009/0118723 A1 | 5/2009 | Lalonde et al. |
| 2010/0057063 A1 | 3/2010 | Arless et al. |
| 2010/0256621 A1 | 10/2010 | Babkin et al. |
| 2011/0009854 A1 | 1/2011 | Babkin et al. |
| 2011/0028960 A1 | 2/2011 | Tin |
| 2011/0029048 A1 | 2/2011 | Mahrouche |
| 2011/0040297 A1 | 2/2011 | Babkin et al. |
| 2011/0054453 A1 | 3/2011 | Lalonde |
| 2011/0125143 A1 | 5/2011 | Gross et al. |
| 2011/0162390 A1 | 7/2011 | Littrup et al. |
| 2011/0184399 A1 | 7/2011 | Wittenberger |
| 2012/0059364 A1 | 3/2012 | Baust et al. |
| 2012/0109118 A1 | 5/2012 | Lalonde et al. |
| 2012/0184955 A1 | 7/2012 | Pivotto et al. |
| 2012/0253336 A1 | 10/2012 | Littrup et al. |
| 2013/0073014 A1 | 3/2013 | Lim et al. |
| 2013/0197498 A1 | 8/2013 | Laske et al. |
| 2013/0204241 A1 | 8/2013 | Baust |
| 2013/0218150 A1 | 8/2013 | Amann et al. |
| 2013/0324987 A1 | 12/2013 | Leung et al. |
| 2013/0331829 A1 | 12/2013 | Babkin et al. |
| 2013/0345688 A1 | 12/2013 | Babkin et al. |
| 2014/0031804 A1 | 1/2014 | Lalonde |
| 2014/0364848 A1 | 12/2014 | Heimbecher et al. |
| 2015/0018809 A1 | 1/2015 | Mihalik |
| 2015/0112328 A1 | 4/2015 | Willard et al. |
| 2015/0250524 A1 | 9/2015 | Moriarty et al. |
| 2016/0135864 A1 | 5/2016 | Babkin |
| 2016/0220294 A1 | 8/2016 | Babkin et al. |
| 2016/0227600 A1 | 8/2016 | Shedletsky et al. |
| 2016/0249859 A1 | 9/2016 | Babkin et al. |
| 2016/0249976 A1 | 9/2016 | Yu et al. |
| 2017/0049495 A1 | 2/2017 | Yu et al. |
| 2017/0151008 A1 | 6/2017 | Mazor et al. |
| 2018/0303535 A1 | 10/2018 | Yu et al. |
| 2019/0038171 A1 | 2/2019 | Howard |
| 2019/0076179 A1 | 3/2019 | Babkin et al. |
| 2019/0125422 A1 | 5/2019 | Babkin et al. |
| 2019/0209229 A1 | 7/2019 | Babkin et al. |
| 2019/0254735 A1 | 8/2019 | Stewart et al. |
| 2019/0262056 A1 | 8/2019 | Yang et al. |
| 2019/0357959 A1 | 11/2019 | Hou et al. |

(56) References Cited

U.S. PATENT DOCUMENTS

| | | | |
|---|---|---|---|
| 2020/0261136 A1 | 8/2020 | Babkin et al. | |
| 2021/0307824 A1 | 10/2021 | Asirvatham et al. | |

FOREIGN PATENT DOCUMENTS

| | | | |
|---|---|---|---|
| JP | 7136180 | A | 5/1995 |
| JP | H07136180 | A | 5/1995 |
| JP | 2008515469 | A | 5/2008 |
| WO | 9308751 | A1 | 5/1993 |
| WO | 1993008751 | A1 | 5/1993 |
| WO | 9749344 | A1 | 12/1997 |
| WO | 1997049344 | A1 | 12/1997 |
| WO | 0211638 | A1 | 2/2002 |
| WO | 2002058576 | A1 | 8/2002 |
| WO | 2002096270 | A2 | 12/2002 |
| WO | 2002011638 | A9 | 4/2003 |
| WO | 2004064914 | A2 | 3/2005 |
| WO | 2006137887 | A2 | 12/2006 |
| WO | 2009009398 | A1 | 1/2009 |
| WO | 2009067497 | A1 | 5/2009 |
| WO | 2013007831 | A1 | 1/2013 |
| WO | 2013013098 | A1 | 1/2013 |
| WO | 2013013099 | A1 | 1/2013 |
| WO | 2015047961 | A2 | 4/2015 |
| WO | 2015057450 | A1 | 4/2015 |
| WO | 2015160574 | A1 | 10/2015 |
| WO | 2016123390 | A1 | 8/2016 |
| WO | 2017048965 | A1 | 3/2017 |
| WO | 2017095756 | A1 | 6/2017 |

OTHER PUBLICATIONS

Arai, Y., et al., "Supercritical Fluids," pp. 161 and 199, ISBN 3540412484, Springer 2002.
Barron, Randall F., "Cryogenic Heat Transfer," pp. 97, 129 and 130, Taylor & Francis, 1999.
Bunch TJ, Cutler MJ, Is pulmonary vein isolation still the cornerstone in atrial fibrillation ablation? J Thorac Dis. Feb. 2015;7(2):132-41.a.
Callans DJ, Gerstenfeld EP, Dixit S, et al. Efficacy of repeat pulmonary vein isolation procedures in patients with recurrent atrial fibrillation. J Cardiovasc Electrophysiol 2004;15:1050-5.
European Search Report for EP04702597 dated Sep. 18, 2007.
European Search Report for EP05858178.6 dated Nov. 5, 2010.
European Search Report for EP08852254 dated Nov. 19, 2010.
European Search Report for EP10184565 dated Feb. 21, 2011.
European Search Report for EP16803999 dated Jan. 7, 2019.
International Preliminary Examination Report dated Oct. 18, 2016 for PCT/US2015/24778.
International Search Report/Written Opinion dated Jan. 14, 2009 for PCT/US2008/84004.
International Search Report dated Oct. 1, 2012 for PCT/US2012/47487.
International Search Report dated Jan. 21, 2015 for PCT/US2014/59684.
International Search Report dated Mar. 18, 2015 for PCT/US14/56839.
International Search Report dated Jul. 8, 2015 for PCT/US2015/24778.
International Search Report dated Jan. 15, 2016 for PCT/US2015/56780.
International Search Report dated Jan. 31, 2017 for PCT/US2016/51954.
International Search Report dated Frb. 2, 2017 for PCT/US2016/63882.
Kim et al. Linear ablation in addition to circumferential pulmonary vein isolation (Dallas lesion set) does not improve clinical outcome in patients with paroxysmal atrial fibrillation: a prospective randomized study. Europace. Mar. 2015;17 (3):388-95.
Kowalski M, Grimes MM, Perez FJ, et al. Histopathologic characterization of chronic radiofrequency ablation lesions for pulmonary vein isolation. J Am Coll Cardiol 2012;59:930-8.
Lemola, Kristina, MD, et al., "Pulmonary Vein Isolation as an End Point for Left Atrial Circumferential Ablation of Atrial Fibrillation," Journal of American College of Cardiology, vol. 46, No. 6, 2005.
Lide, D.R. and Keihiaian, H.V., "CRC Handbook of Thermophysical and Thermochemical Data," p. 375, CRC Press 1994.
McGann CJ, Kholmovski EG, Oakes RS, et al. New magnetic resonance imaging-based method for defining the extent of left atrial wall injury after the ablation of atrial fibrillation. J Am Coll Cardiol 2008;52:1263-71.
Ouyang F, Tilz R, Chun J, et al. Long-term results of catheter ablation in paroxysmal atrial fibrillation: lessons from a 5-year follow-up. Circulation 2010;122:2368-77.
Ranjan R, Kato R, Zviman MM, et al. Gaps in the ablation line as a potential cause of recovery from electrical isolation and their visualization using MRI. Circ Arrhythm Electrophysiol 2011;4:279-86.
Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.
Sawhney N, Anousheh R, Chen WC, et al. Five-year outcomes after segmental pulmonary vein isolation for paroxysmal atrial fibrillation. Am J Cardiol 2009;104:366-72.
Skanes, Allan C., et al., "Cryoblation: Potentialsand Pitfalls," doi:10.1046/j.1540-8167.2004.15106.x, Jul. 6, 2004.
Stuehlinger, M., et al., "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.
Sun, Ya-ping, Supercritical Fluid Technology in Materials Science and Engineering, pp. 1 and 26, CRC Press 2002.
Thakore, S.B. and Bhatt, B.I., "Introduction to Process Engineering and Design," Chemical Engineering Series, pp. 27-28, McGraw-Hill 2008.
Verma A, Kilicaslan F, Pisano E, et al. Response of atrial fibrillation to pulmonary vein antrum isolation is directly related to resumption and delay of pulmonary vein conduction. Circulation 2005;112:627-35.
International Preliminary Examination Report dated Mar. 19, 2020 for PCT/US2018/049467.
Australian Examination Report No. 1, dated Jul. 31, 2018 for 2014327045.
International Search Report dated Mar. 18, 2015 of PCT/US2014/056839.
International Search Report dated Apr. 25, 2019 of PCT/US2019/012754.
International Search Report dated May 24, 2019 of PCT/US2019/012789.
International Search Report dated Nov. 21, 2018 of PCT/US2018/049467.
Office Action dated Jul. 13, 2018 for U.S. Appl. No. 15/028,925.
Office Action dated Jul. 26, 2018 for U.S. Appl. No. 14/915,631.
Supplemental European Search Report dated Apr. 23, 2018 for EP15858716.
Supplementary European Search Report dated Jan. 7, 2019 of the counterpart application EP16803999.8.
Supp European Search Report, EP18853221, dated Apr. 22, 2021.

* cited by examiner

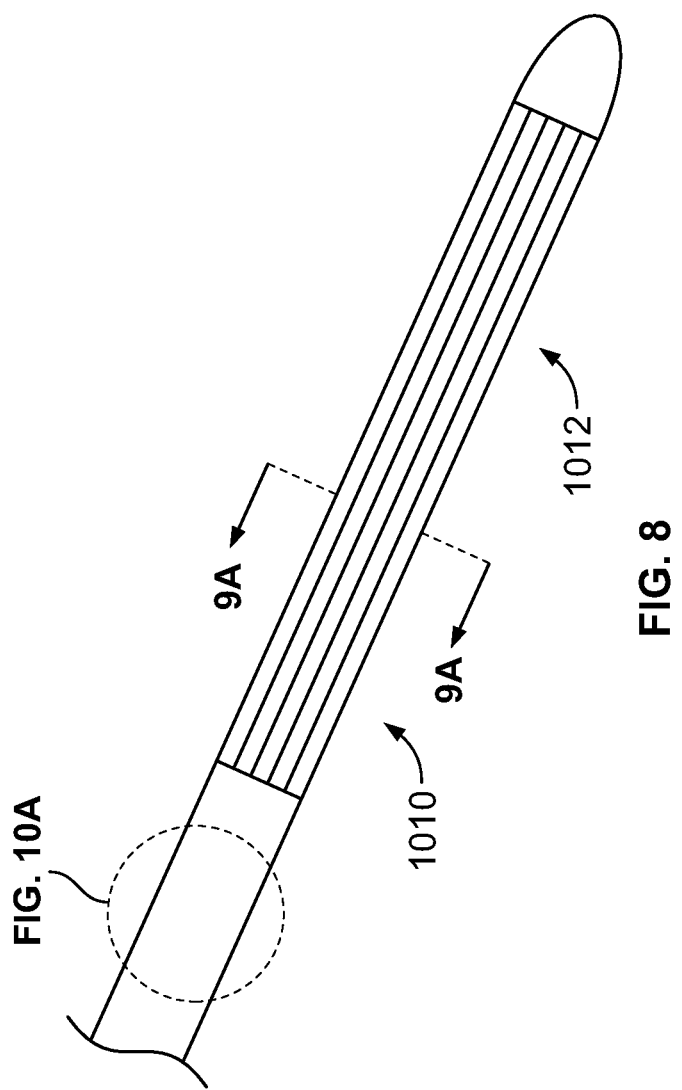

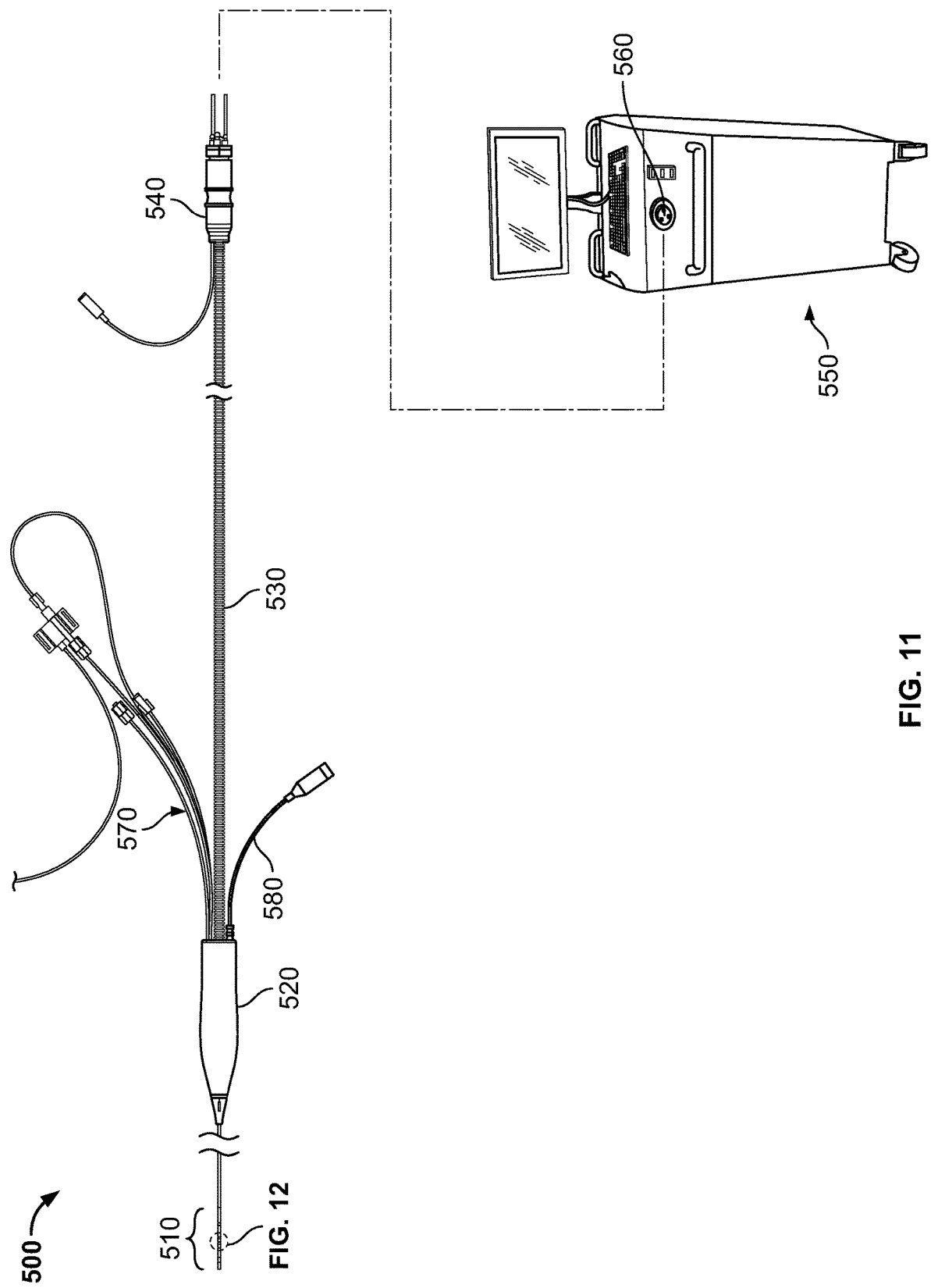

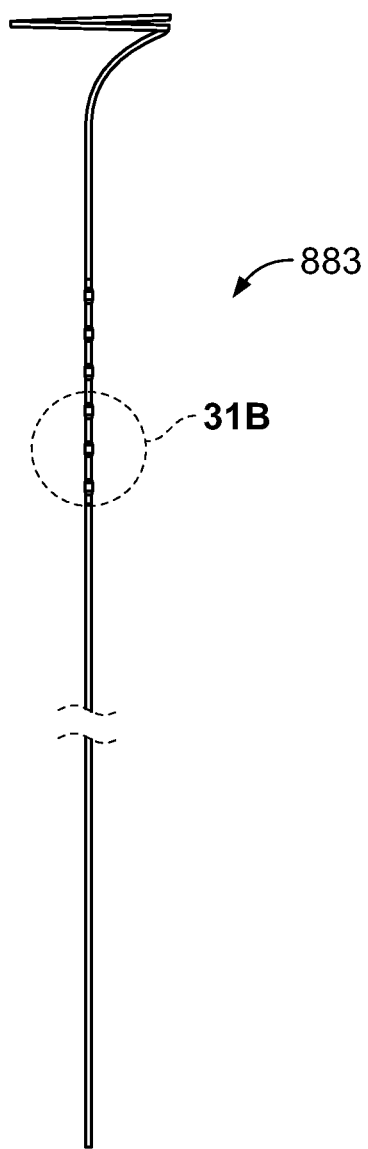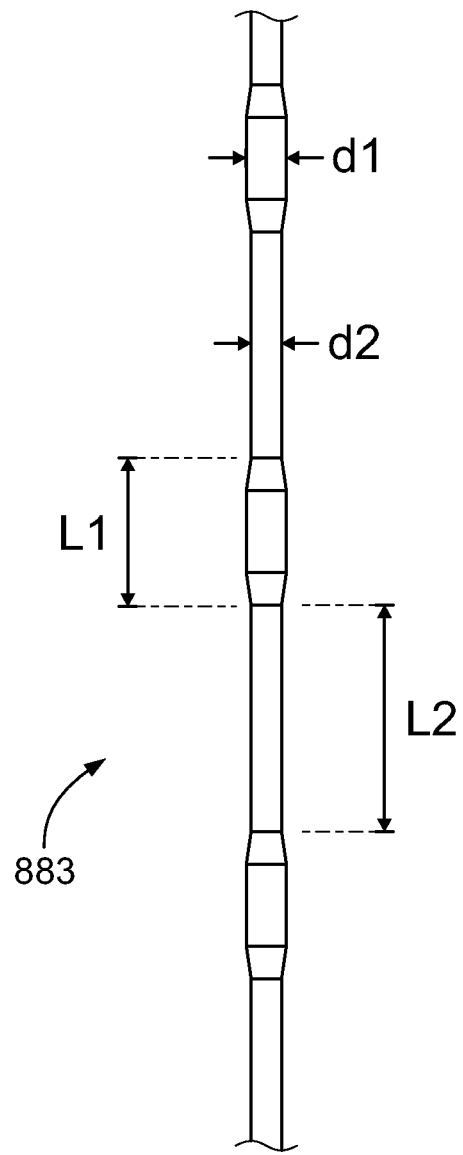
FIG. 31A
FIG. 31B

ABLATION CATHETER HAVING A SHAPE MEMORY STYLET

CROSS-REFERENCE TO RELATED APPLICATIONS

This application claims the benefit of (i) U.S. Provisional Application No. 62/554,483, filed Sep. 5, 2017, (ii) U.S. Provisional Application No. 62/575,998, filed Oct. 23, 2017 and (iii) U.S. Provisional Application No. 62/669,039, filed May 9, 2018. The entire contents of each provisional application are incorporated herein by reference in their entirety for all purposes.

BACKGROUND

1. Field of the Invention

Embodiments of the invention relate to cryosurgery and more particularly to cryoablation systems and catheters for the treatment of heart disease.

2. Description of the Related Art

Atrial flutter and atrial fibrillation are heart conditions in which the left or right atrium of the heart beat improperly. Atrial flutter is a condition when the atria beat very quickly, but still evenly. Atrial fibrillation is a condition when the atria beat very quickly, but unevenly.

These conditions are often caused by aberrant electrical behavior of some portion of the atrial wall. Certain parts of the atria, or nearby structures such as the pulmonary veins, can misfire in their production or conduction of the electrical signals that control contraction of the heart, creating abnormal electrical signals that prompt the atria to contract between normal contractions caused by the normal cascade of electrical impulses. This can be caused by spots of ischemic tissue, referred to as ectopic foci, or by electrically active fibers in the pulmonary veins, for example.

Ventricular tachycardia (V-tach or VT) is a type of regular and fast heart rate that arises from improper electrical activity in the ventricles of the heart. In ventricular tachycardia, the abnormal electrical signals in the ventricles cause the heart to beat faster than normal, usually 100 or more beats a minute, out of sync with the upper chambers. When this happens, the heart may not be able to pump enough blood to the body and lungs because the chambers are beating so fast or out of sync with each other that the chambers do not have time to fill properly. Thus, V-tach may result in cardiac arrest and may turn into ventricular fibrillation.

Atrial fibrillation is one of the more prevalent types of heart conditions. Failing to treat atrial fibrillation can lead to a number of undesirable consequences including heart palpitations, shortness of breath, weakness and generally poor blood flow to the body.

Various techniques are practiced to treat atrial fibrillation. One technique to treat AF is pulmonary vein isolation (PVI). PVI is performed by creating lesions circumscribing the pulmonary veins. The PVI serves to block the errant or abnormal electrical signals.

A challenge in performing PVI, however, is to obtain a lasting or permanent isolation of the pulmonary veins. This shortcoming is highlighted in various studies. In one long-term follow-up study that investigated the rate of pulmonary vein reconnection after initial isolation, 53% of 161 patients were free of AF. In 66 patients, a repeat ablation was performed for repeat arrhythmia. The rate of pulmonary vein reconnection was high at 94% (62 of 66 patients). (Ouyang F, Tilz R, Chun J, et al. Long-term results of catheter ablation in paroxysmal atrial fibrillation: lessons from a 5-year follow-up. Circulation 2010; 122:2368-77.)

One reason that some PVI treatments are not durable is because of the phenomena of pulmonary vein (or electrical) reconnection. (Sawhney N, Anousheh R, Chen W C, et al. Five-year outcomes after segmental pulmonary vein isolation for paroxysmal atrial fibrillation. Am J Cardiol 2009; 104:366-72) (Callans D J, Gerstenfeld E P, Dixit S, et al. Efficacy of repeat pulmonary vein isolation procedures in patients with recurrent atrial fibrillation. J Cardiovasc Electrophysiol 2004; 15:1050-5) (Verma A, Kilicaslan F, Pisano E, et al. Response of atrial fibrillation to pulmonary vein antrum isolation is directly related to resumption and delay of pulmonary vein conduction. Circulation 2005; 112:627-35)

Pulmonary vein reconnection may be attributed to gaps and incomplete or discontinuous isolation of the veins. (Bunch T J, Cutler M J. Is pulmonary vein isolation still the cornerstone in atrial fibrillation ablation? J Thorac Dis. 2015 February; 7(2):132-41). Incomplete isolation is a result of residual gap(s) within the encircling lesion or lack of transmural lesions. (McGann C J, Kholmovski E G, Oakes R S, et al. New magnetic resonance imaging-based method for defining the extent of left atrial wall injury after the ablation of atrial fibrillation. J Am Coll Cardiol 2008; 52:1263-71.) (Ranjan R, Kato R, Zviman M M, et al. Gaps in the ablation line as a potential cause of recovery from electrical isolation and their visualization using MRI. Circ Arrhythm Electrophysiol 2011; 4:279-86.)

Additionally, early recurrence of AF post ablation may be an early marker of incomplete pulmonary vein isolation. This is supported by a study of 12 patients that underwent a maze procedure after a failed radiofrequency ablation. Notably, myocardial biopsies showed anatomic gaps and/or non-transmural lesions in pulmonary veins that had reconnected. (Kowalski M, Grimes M M, Perez F J, et al. Histopathologic characterization of chronic radiofrequency ablation lesions for pulmonary vein isolation. J Am Coll Cardiol 2012; 59:930-8.)

This is further supported in a canine study in which endocardial conduction block was demonstrated and post procedural gaps were identified using MRI within the line of ablation. Long-term follow up data demonstrated that those pulmonary veins with the MRI-identified gaps were more likely to become electrically reconnected with symptomatic recurrences. (Ranjan R, Kato R, Zviman M M, et al. Gaps in the ablation line as potential cause of recovery from electrical isolation and their visualization using MRI. Circ Arrhythm Electrophysiol 2011; 4:279-86.)

Various attempts to solve the above referenced problem include making linear ablations in combination with circumferential pulmonary vein isolation (CPVI). One study, for example, compared clinical outcomes of CPVI with additional linear ablations and CPVI in a prospective randomized controlled study among patients with paroxysmal AF. The study enrolled 100 paroxysmal AF patients (male 75.0%, 56.4±11.6 years old) who underwent radio frequency circumferential ablation (RFCA) and were randomly assigned to the CPVI group (n=50) or the catheter Dallas lesion group (CPVI, posterior box lesion, and anterior linear ablation, n=50). The catheter Dallas lesion group required longer procedure (190.3±46.3 vs. 161.1±30.3 min, P<0.001) and ablation times (5345.4±1676.4 vs. 4027.2±878.0 s, P<0.001) than the CPVI group. Complete bidirectional conduction block rate was 68.0% in the catheter Dallas lesion group and 100% in the CPVI group. Procedure-related complication rates were not significantly different between the catheter Dallas lesion (0%) and CPVI groups (4%, P=0.157). During the 16.3±4.0 months of follow-up, the clinical recurrence rates were not significantly different between the two groups, regardless of complete bidirectional conduction block achievement after linear ablation. (Kim et al. Linear ablation in addition to circumferential pulmonary vein isolation (Dallas lesion set) does not improve clinical outcome in patients with paroxysmal atrial fibrillation: a prospective randomized study. Europace. 2015 March; 17(3):388-95.)

Thus, in view of the above referenced study, adding more ablation points around the vein entries, and/or attempting to add a linear lesion by using point by point ablation, does not appear to be an optimal solution to prevent gap(s) along the encircling lesion. Additionally, adding multiple points and lines undesirably increases the procedure time.

In view of the above shortcomings, various ablation catheters have been proposed for creation of the lesion, including flexible cryoprobes or cryocatheters, bipolar RF catheters, monopolar RF catheters (using ground patches on the patient's skin), microwave catheters, laser catheters, and ultrasound catheters. U.S. Pat. No. 6,190,382 to Ormsby and U.S. Pat. No. 6,941,953 to Feld, for example, describe RF ablation catheters for ablating heart tissue. These approaches are attractive because they are minimally invasive and can be performed on a beating heart. However, these approaches have a low success rate. The low success rate may be due to incomplete lesion formation. A fully transmural lesion is required to ensure that the electrical impulse causing atrial fibrillation are completely isolated from the remainder of the atrium, and this is difficult to achieve with beating heart procedures.

Thus, the challenge for the surgeon is to place the catheter/probe along the correct tissue contour such that the probe makes complete contact with the tissue. Due to the nature of the procedure and the anatomical locations where the lesions must be created, the catheter must be sufficiently flexible and adjustable such that they can match the shape and contour of the tissue to be ablated.

Malleable and flexible cryoprobes are described in U.S. Pat. Nos. 6,161,543 and 8,177,780, both to Cox, et al. The described probes have a malleable shaft. In embodiments, a malleable metal rod is coextruded with a polymer to form the shaft. The malleable rod permits the user to plastically deform the shaft into a desired shape so that a tip can reach the tissue to be ablated.

U.S. Pat. No. 5,108,390, issued to Potocky et al, discloses a highly flexible cryoprobe that can be passed through a blood vessel and into the heart without external guidance other than the blood vessel itself.

A challenge with some of the above apparatuses, however, is making continuous contact along the anatomical surface such that a continuous lesion may be created. This challenge is amplified not only because of the varying contours and shapes of the target tissue because of the location in the body but also because of variations in anatomy between patients. Thus, different treatment procedures and patient anatomy require different catheters to be designed and used. Another challenge is to be able to adjust the shape of the catheter in situ to address these variations in anatomy, etc.

Additional challenges with some of the above apparatuses is with efficient thermal conductivity, i.e., cooling/heat transfer, between the internal cooling/heating elements of the devices and the exterior jackets/sleeves of the devices. Thus, freezing and heating temperatures may need be efficiently transferred to the tissue to be ablated.

Accordingly, there is a need for improved methods and systems for providing minimally invasive, adjustably shaped, safe and efficient cryogenic cooling of tissues. These improved systems include improved apparatuses and methods to form continuous lesions in target tissue regardless of the condition being treated and variations in patient anatomy.

There is also a need for an improved apparatus and method to treat AF, atrial flutter and V-tach and to achieve more complete, durable, and safe electrical signal isolation within the various chambers of the heart, including pulmonary vein isolation.

SUMMARY

One aspect of the embodiments of the present invention is directed to an ablation apparatus for creating a lesion in target tissue, where the ablation apparatus comprises an ablation shaft having a handle, a first portion, an ablation portion, a distal tip, at least one ablation energy delivery lumen, at least one ablation energy return lumen, and a stylet lumen that extends substantially along a length of the ablation shaft from the handle to at least the ablation portion, The ablation apparatus also includes a stylet that is capable of being inserted into the stylet lumen, where the stylet comprises a shape-memory material. In some embodiments, at least a distal portion of the stylet is pre-set with a shape that corresponds to a desired shape of the lesion to be formed.

Another aspect of the embodiments of the present invention is direct to a cryoablation catheter for creating a lesion in target tissue, where the cryoablation catheter comprises an ablation shaft comprising a handle, a freezing portion, a distal tip, a plurality of cryogen delivery lumens, a plurality of cryogen return lumens, a plurality of electrodes on an exterior surface of the freezing portion, at least one service lumen, and a stylet lumen that extends substantially along a length of the ablation shaft from the handle to at least the freezing portion. The cryoablation catheter also comprises a stylet capable of being inserted into the stylet lumen, where the stylet comprises a shape-memory material. In some embodiments, at least a distal portion of the stylet is pre-set with a shape that corresponds to a desired shape of the lesion to be formed.

Another aspect of the embodiments of the present invention is direct to a cryoablation catheter for creating a lesion in target tissue, where the cryoablation catheter comprises an ablation shaft comprising a handle, a freezing portion, a distal tip, a plurality of cryogen delivery tubes, wherein each cryogen delivery tube comprises an inner tube having an outer tube surrounding the inner tube thereby defining a gap between the inner tube and the outer tube, a plurality of cryogen return tubes, wherein each cryogen return tube comprises an inner tube having an outer tube surrounding the inner tube thereby defining a gap between the inner tube and the outer tube, a plurality of electrodes on an exterior surface of the freezing portion, at least one service lumen, and a stylet lumen that extends substantially along a length of the ablation shaft from the handle to at least the freezing portion. The cryoablation catheter also includes a stylet inserted into the stylet lumen, where the stylet comprises a shape-memory material and has a distal portion that is pre-set with a shape that corresponds to a desired shape of the lesion to be formed.

An additional aspect of the embodiments of the present invention is directed to an ablation apparatus for creating a lesion in target tissue, where the ablation apparatus comprises an ablation shaft having a handle, a first portion, an ablation portion, a distal tip, at least one ablation energy delivery lumen, at least one ablation energy return lumen, and a stylet lumen that extends substantially along a length of the ablation shaft from the handle to at least the ablation portion, The ablation apparatus also includes a stylet that is capable of being inserted into the stylet lumen, where the stylet comprises a shape-memory material. In some embodiments, at least a distal portion of the stylet is pre-set with a shape that corresponds to a desired shape of the lesion to be formed. In some embodiments, the stylet is designed to have multiple flexibilities along its length. The multiple flexibilities are due to a removal of material in portions of the stylet along its length. The removed material can be in the form of smaller diameter portions, circumferential grooves, longitudinal grooves and/or holes.

Another aspect of the embodiments of the present invention is direct to a cryoablation catheter for creating a lesion in target tissue, where the cryoablation catheter comprises an ablation shaft comprising a handle, a freezing portion, a distal tip, a plurality of cryogen delivery lumens, a plurality of cryogen return lumens, a plurality of electrodes on an exterior surface of the freezing portion, at least one service lumen, and a stylet lumen that extends substantially along a length of the ablation shaft from the handle to at least the freezing portion. The cryoablation catheter also comprises a stylet capable of being inserted into the stylet lumen, where the stylet comprises a shape-memory material. In some embodiments, at least a distal portion of the stylet is pre-set with a shape that corresponds to a desired shape of the lesion to be formed. In some embodiments, the stylet is designed to have multiple flexibilities along its length. The multiple flexibilities are due to a removal of material in portions of the stylet along its length. The removed material can be in the form of smaller diameter portions, circumferential grooves, longitudinal grooves and/or holes.

Another aspect of the embodiments of the present invention is direct to a cryoablation catheter for creating a lesion in target tissue, where the cryoablation catheter comprises an ablation shaft comprising a handle, a freezing portion, a distal tip, a plurality of cryogen delivery tubes, wherein each cryogen delivery tube comprises an inner tube having an outer tube surrounding the inner tube thereby defining a gap between the inner tube and the outer tube, a plurality of cryogen return tubes, wherein each cryogen return tube comprises an inner tube having an outer tube surrounding the inner tube thereby defining a gap between the inner tube and the outer tube, a plurality of electrodes on an exterior surface of the freezing portion, at least one service lumen, and a stylet lumen that extends substantially along a length of the ablation shaft from the handle to at least the freezing portion. The cryoablation catheter also includes a stylet inserted into the stylet lumen, where the stylet comprises a shape-memory material and has a distal portion that is pre-set with a shape that corresponds to a desired shape of the lesion to be formed. In some embodiments, the stylet is designed to have multiple flexibilities along its length. The multiple flexibilities are due to a removal of material in portions of the stylet along its length. The removed material can be in the form of smaller diameter portions, circumferential grooves, longitudinal grooves and/or holes.

Additional embodiments of the present invention is directed to an ablation apparatus for creating a lesion in target tissue, where the ablation apparatus comprises an ablation shaft having a handle, a first portion, an ablation portion, a distal non-ablation portion, at least one ablation energy delivery lumen, at least one ablation energy return lumen, and a stylet lumen that extends substantially along a length of the ablation shaft from the handle to at least the ablation portion. The ablation apparatus also includes a stylet capable of being inserted into the stylet lumen where the stylet comprises a shape-memory material and has a distal portion that is pre-set with a shape that corresponds to (i) a desired shape of the lesion to be formed and (ii) a shape of a diagnostic portion, wherein the diagnostic portion of the stylet corresponds to the distal non-ablation portion of the ablation shaft. In some embodiments, the stylet is designed to have multiple flexibilities along its length. The multiple flexibilities are due to a removal of material in portions of the stylet along its length, the alloy composition of the stylet and the shape setting/training heat treatments of the stylet. The removed material can be in the form of smaller diameter portions, circumferential grooves, longitudinal grooves and/or holes.

Another aspect of the embodiments of the present invention is directed to a cryoablation catheter for creating a lesion in target tissue where the cryoablation catheter comprises an ablation shaft having a handle, a freezing portion, a distal non-freezing portion, a plurality of cryogen delivery lumens, a plurality of cryogen return lumens, a plurality of electrodes on an exterior surface of the freezing portion, at least one service lumen, and a stylet lumen that extends substantially along a length of the ablation shaft from the handle to at least the freezing portion. The cryoablation catheter also includes a stylet capable of being inserted into the stylet lumen, where the stylet comprises a shape-memory material. A distal portion of the cryoablation catheter includes a diagnostic portion.

Another aspect of the embodiments of the present invention is directed to a cryoablation catheter for creating a lesion in target tissue. The cryoablation catheter comprises an ablation shaft having a handle, a freezing portion, a distal non-freezing portion, a plurality of cryogen delivery tubes, wherein each cryogen delivery tube comprises an inner tube having an outer tube surrounding the inner tube thereby defining a gap between the inner tube and the outer tube, a plurality of cryogen return tubes, wherein each cryogen return tube comprises an inner tube having an outer tube surrounding the inner tube thereby defining a gap between the inner tube and the outer tube, a plurality of electrodes on an exterior surface of the freezing portion, at least one service lumen, and a stylet lumen that extends substantially along a length of the ablation shaft from the handle to at least the freezing portion. The cryoablation catheter also comprises a stylet inserted into the stylet lumen, where the stylet comprises a shape-memory material and includes a distal portion that is pre-set with a shape that corresponds to (i) a desired shape of the lesion to be formed and (ii) a shape of a diagnostic portion to be received within a pulmonary vein entry, wherein the diagnostic portion of the stylet corresponds to the distal non-freezing portion of the ablation shaft.

In some embodiments, an ablation apparatus for creating a lesion in target tissue is disclosed. The ablation apparatus comprises an ablation shaft having a handle, a first portion, an ablation portion, a non-ablation distal portion, at least one ablation energy delivery lumen, at least one ablation energy return lumen, and a stylet lumen that extends substantially along a length of the ablation shaft from the handle to at least the ablation portion. The ablation apparatus also includes a stylet capable of being inserted into the stylet lumen where the stylet comprises a shape-memory material and has a distal portion that is pre-set with a shape that corresponds to (i) a desired shape of the lesion to be formed and (ii) a shape of a diagnostic portion, wherein the diagnostic portion of the stylet corresponds to the distal non-ablation portion of the ablation shaft, wherein the stylet has a plurality of flexibilities along its length, and wherein the plurality of flexibilities are due to mechanical alterations to the stylet.

Another aspect of the present invention is directed to an ablation apparatus for creating a lesion in target where the ablation apparatus comprises an ablation shaft having a handle, a first portion, an ablation portion, a non-ablation distal portion, at least one ablation energy delivery lumen, at least one ablation energy return lumen, and a stylet lumen that extends substantially along a length of the ablation shaft from the handle to at least the ablation portion. The ablation apparatus also includes a stylet capable of being inserted into the stylet lumen, where the stylet comprises a shape-memory material and has a distal portion that is pre-set with a shape that corresponds to (i) a desired shape of the lesion to be formed and (ii) a shape of a diagnostic portion, wherein the diagnostic portion of the stylet corresponds to the distal non-ablation portion of the ablation shaft, wherein the stylet has a plurality of flexibilities along its length, and wherein the plurality of flexibilities are due removal of material from portions of the stylet.

The description, objects and advantages of embodiments of the present invention will become apparent from the detailed description to follow, together with the accompanying drawings.

BRIEF DESCRIPTION OF THE DRAWINGS

The above-mentioned aspects, as well as other features, aspects and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

FIG. 8 is a perspective view of another embodiment of a cryoablation catheter having a flexible distal treatment section;

FIG. 11 is a perspective view of another embodiment of a cryoablation catheter having a flexible distal treatment section;

FIG. 31A depicts a method of altering the flexibility of a portion of a stylet, according to an embodiment of the invention;

FIG. 31B depicts View A in FIG. 31A, according to an embodiment of the invention;

DETAILED DESCRIPTION

Figure 1:
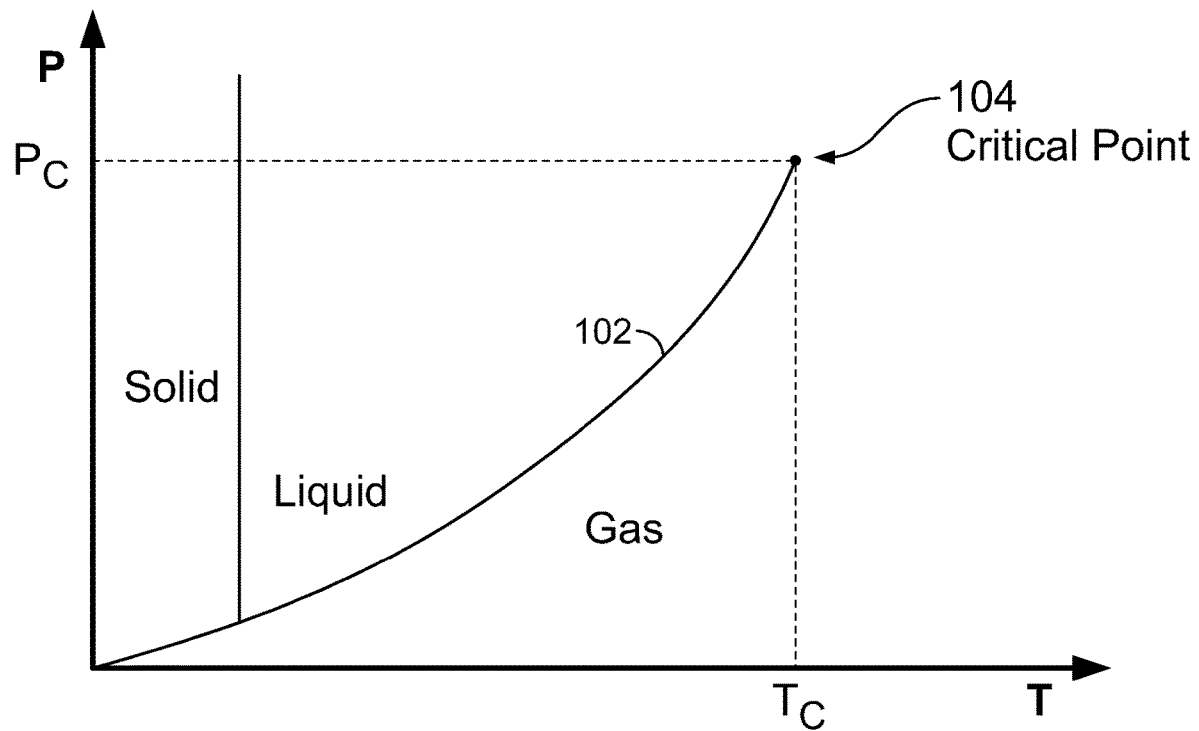
FIG. 1 illustrates a typical cryogen phase diagram.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein.

For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with that of the present invention (in which case what is present herein shall prevail).

Embodiments of the invention make use of thermodynamic processes using cryogens that provide cooling without encountering the phenomenon of vapor lock.

Cryogen Phase Diagram and Near Critical Point

This application uses phase diagrams to illustrate various thermodynamic processes. An example phase diagram is shown in FIG. 1. The phase diagram includes axes that correspond to pressure P and temperature T, and a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c=3.396$ MPa and $T_c=-147.15°$ C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are equal only at the critical point 104. The distinction between liquid and gas disappears at the critical point 104. The blockage of forward flow by gas expanding ahead of the liquid cryogen ("vapor lock") is thus avoided when a cryogen flows at conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryo-treatment region.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase, where the fluid has the properties of both a liquid and a gas (i.e., a dense fluid without surface tension capable of frictionless flow).

Van der Waals thermodynamic equation of state is a well-established equation for describing gases and liquids:

$$(p+3/v^2)(3v-1)=8t \qquad \text{[Eq. 1]}$$

where $p=P/P_c$, $v=V/V_c$, and $t=T/T_c$, and $P_c$, $V_c$, and $T_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference in its entirety for all purposes.

In embodiments of the present invention, the reduced pressure p is fixed at a constant value of approximately one, and hence at a fixed physical pressure near the critical pressure, while the reduced temperature t varies with the heat load applied to the device. If the reduced pressure p is a constant set by the engineering of the system, then the reduced molar volume v is an exact function of the reduced temperature t.

In other embodiments of the present invention, the operating pressure p may be adjusted so that over the course of variations in the temperature t of the device, v is maintained below some maximum value at which the vapor lock condition will result. It is generally desirable to maintain p at the lowest value at which this is true because boosting the pressure to achieve higher values of p may involve use of a more complex and more expensive compressor, resulting in more expensive procurement and maintenance of the entire apparatus support system and lower overall cooling efficiency.

The conditions for v depend in a complex way on the volume flow rate dV/dt, the heat capacity of the liquid and vapor phases, and the transport properties such as the thermal conductivity, viscosity, etc., in both the liquid and the vapor. The exact relationship is not derived here in closed form algebraically, but may be determined numerically by integrating the model equations that describe mass and heat transport within the cooling device. Conceptually, vapor lock occurs when the rate of heating of the tip (or other device structure for transporting the cryogen and cooling the tissue) produces the vapor phase. The cooling power of this vapor phase, which is proportional to the flow rate of the vapor multiplied by its heat capacity divided by its molar volume, is not able to keep up with the rate of heating to the tip. When this occurs, more and more of the vapor phase is formed in order to absorb the excess heat through the conversion of the liquid phase to vapor in the cryogen flow. This creates a runaway condition where the liquid converts into vapor phase to fill the tip, and effectively all cryogen flow stops due to the large pressure that results in this vapor phase as the heat flow into the tip increases its temperature and pressure rapidly. This condition is called "vapor lock."

In accordance with one embodiment of the present invention, the liquid and vapor phases are substantially identical in their molar volume. The cooling power is at the critical point, and the cooling system avoids vapor lock. Additionally, at conditions slightly below the critical point, the apparatus may avoid vapor lock as well.

Cryoablation System

Figure 2:
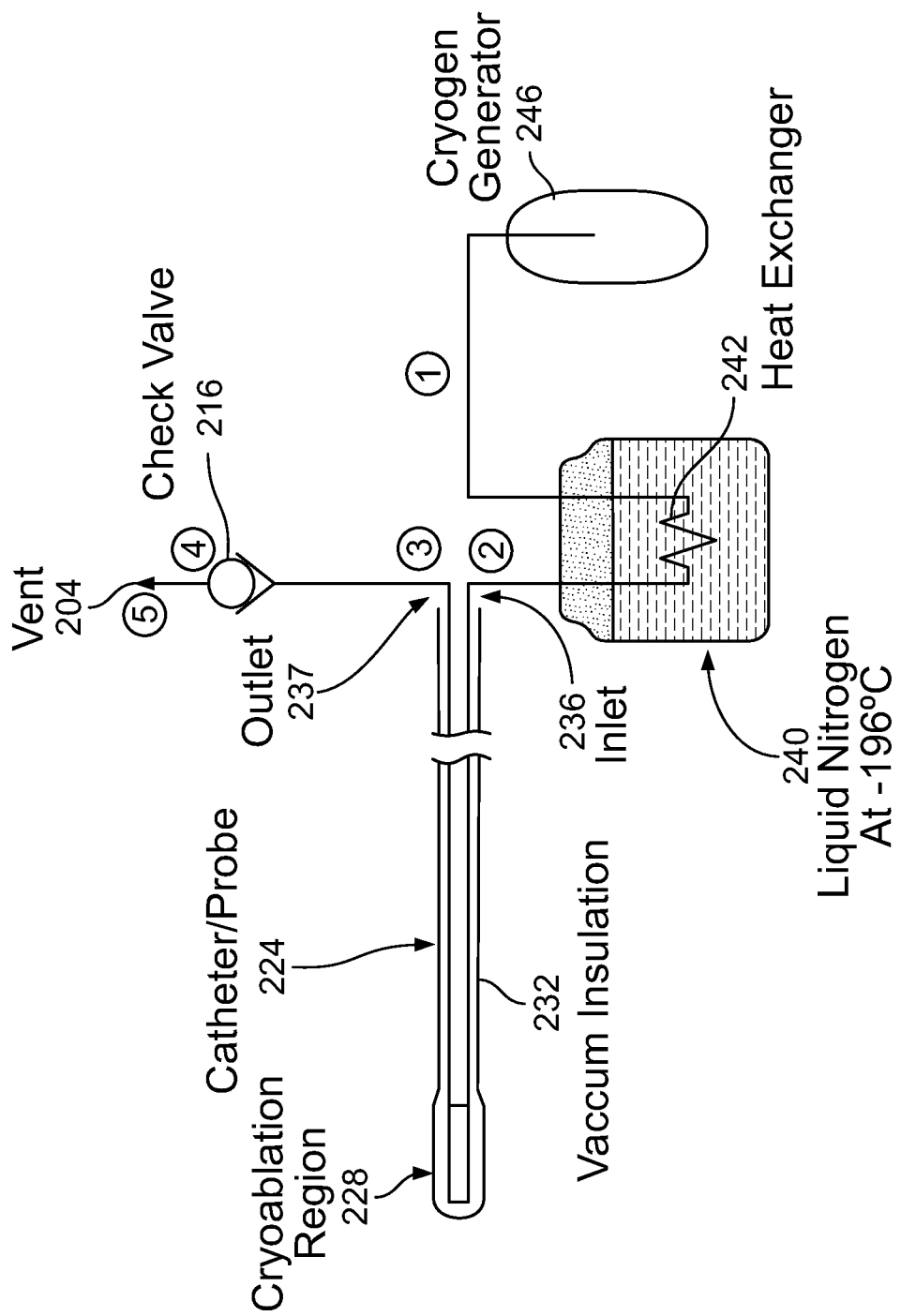
FIG. 2 is a schematic illustration of a cryogenic cooling system.
Figure 3:
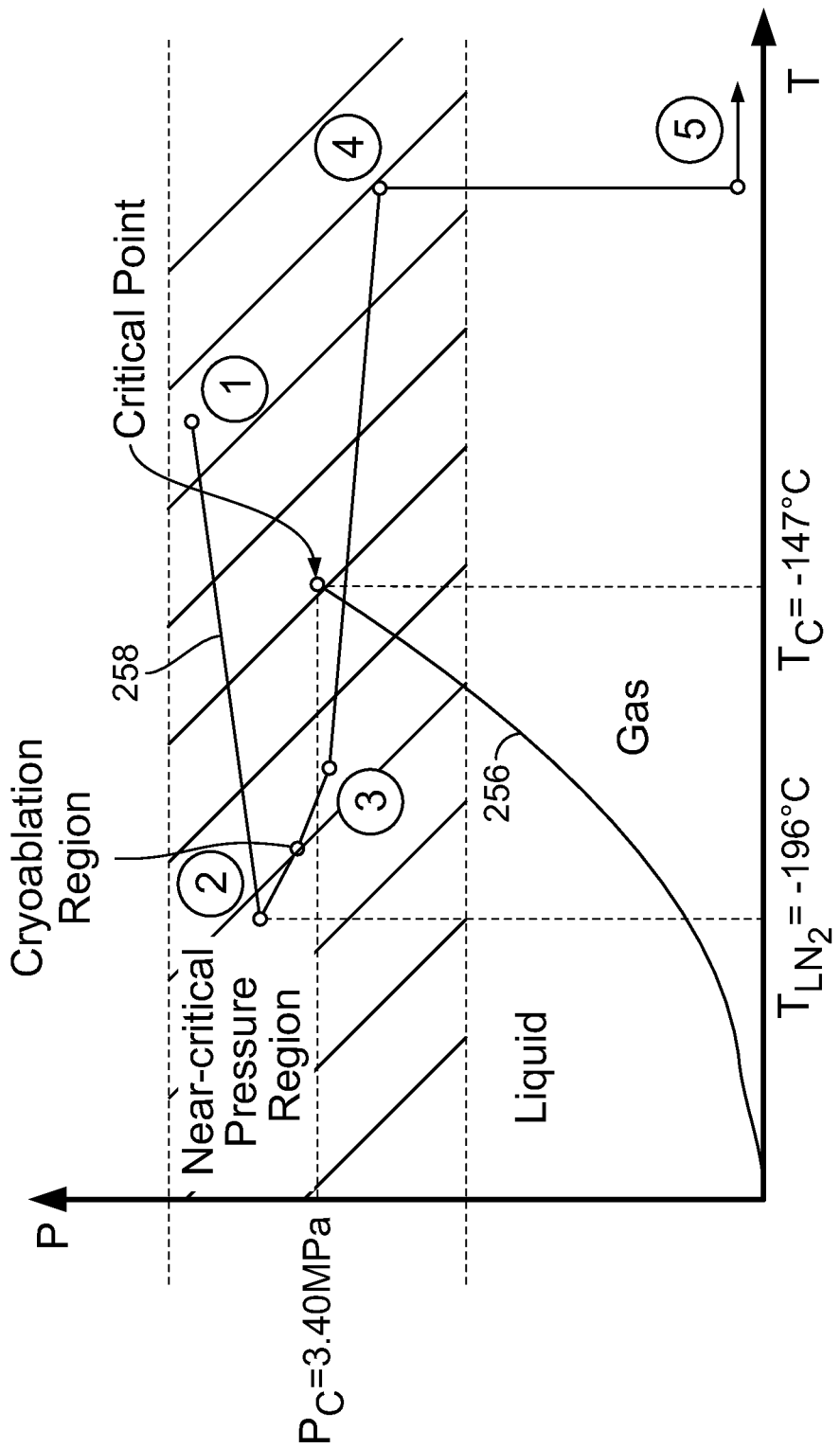
FIG. 3 is a cryogen phase diagram corresponding to the system shown in FIG. 2 where the cryogen is $N_2$.

FIG. 2 provides a schematic illustration of a structural arrangement for a cryogenic system in one embodiment, and FIG. 3 provides a phase diagram that illustrates a thermodynamic path taken by the cryogen when the system of FIG. 2 is operated. The circled numerical identifiers in the two figures correspond so that a physical position is indicated in FIG. 2 where operating points identified along the thermodynamic path are achieved. The following description thus sometimes makes simultaneous reference to both the structural drawing of FIG. 2 and to the phase diagram of FIG. 3 in describing physical and thermodynamic aspects of the cooling flow.

For purposes of illustration, both FIGS. 2 and 3 make specific reference to a nitrogen cryogen, but this is not intended to be limiting. Embodiments of the invention may more generally be used with any suitable cryogen such as, for example, argon, neon, helium, hydrogen, and oxygen.

In FIG. 3, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2 and 3 by label ①. The cooling cycle may generally begin at any point in the phase diagram having a pressure above or slightly below $P_c$, although it is advantageous for the pressure to be near the critical-point pressure $P_c$. The cooling efficiency of the process described herein is generally greater when the initial pressure is near the critical-point pressure $P_c$ so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$.

As used herein, the term "near critical" is meant to refer to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. Reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2, the cryogen is flowed through a tube, at least part of which is surrounded by a reservoir 240 of the cryogen in a liquid state, reducing its temperature without substantially changing its pressure. In FIG. 2, reservoir is shown as liquid $N_2$, with a heat exchanger 242 provided within the reservoir 240 to extract heat from the flowing cryogen. Outside the reservoir 240, thermal insulation may be provided around the tube to prevent unwanted warming of the cryogen as it is flowed from the cryogen generator 246. At point ②, after being cooled by being brought into thermal contact with the liquid cryogen, the cryogen has a lower temperature but is at substantially the initial pressure. In some instances, there may be a pressure change, as is indicated in FIG. 3 in the form of a slight pressure decrease, provided that the pressure does not drop substantially below the critical-point pressure $P_c$, i.e. does not drop below the determined minimum pressure. In the example shown in FIG. 3, the temperature drop as a result of flowing through the liquid cryogen is about 50° C.

The cryogen is then provided to a device for use in cryogenic applications. In the exemplary embodiment shown in FIG. 2, the cryogen is provided to an inlet 236 of a catheter 224, such as may be used in medical cryogenic endovascular applications, but this is not a requirement.

Indeed, the form of the medical device may vary widely and include without limitation: instruments, appliances, catheters, devices, tools, apparatus', and probes regardless of whether such probe is short and rigid, or long and flexible, and regardless of whether it is intended for open, minimal, non-invasive, manual or robotic surgeries.

In embodiments, the cryogen may be introduced through a proximal portion of a catheter, continue along a flexible intermediate section of the catheter, and into the distal treatment section of the catheter. As the cryogen is transported through the catheter, and across the cryoablation treatment region 228, between labels ② and ③ in FIGS. 2 and 3, there may be a slight change in pressure and/or temperature of the cryogen as it moves through the interface with the device, e.g. cryoablation region 228 in FIG. 2. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Flow of the cryogen from the cryogen generator 246 through the catheter 224 or other device may be controlled in the illustrated embodiment with an assembly that includes a check valve 216, a flow impedance, and/or a flow controller. The catheter 224 itself may comprise a vacuum insulation 232 (e.g., a cover or jacket) along its length and may have a cold cryoablation region 228 that is used for the cryogenic applications. Unlike a Joule-Thomson probe, where the pressure of the working cryogen changes significantly at the probe tip, these embodiments of the invention provide relatively little change in pressure throughout the apparatus. Thus, at point ④, the temperature of the cryogen has increased approximately to ambient temperature, but the pressure remains elevated. By maintaining the pressure above or near the critical-point pressure $P_c$ as the cryogen is transported through the catheter, vapor lock are avoided.

The cryogen pressure returns to ambient pressure at point ⑤. The cryogen may then be vented through vent 204 at substantially ambient conditions.

Examples of cryoablation systems, their components, and various arrangements are described in the following commonly-assigned U.S. patents and U.S. patent applications: U.S. patent application Ser. No. 10/757,768, which issued as U.S. Pat. No. 7,410,484, on Aug. 12, 2008 entitled "CRYOTHERAPY PROBE," filed Jan. 14, 2004 by Peter J. Littrup et al.; U.S. patent application Ser. No. 10/757,769, which issued as U.S. Pat. No. 7,083,612 on Aug. 1, 2006, entitled "CRYOTHERAPY SYSTEM," filed Jan. 14, 2004 by Peter J. Littrup et al.; U.S. patent application Ser. No. 10/952,531, which issued as U.S. Pat. No. 7,273,479 on Sep. 25, 2007 entitled "METHODS AND SYSTEMS FOR CRYOGENIC COOLING," filed Sep. 27, 2004 by Peter J. Littrup et al.; U.S. patent application Ser. No. 11/447,356, which issued as U.S. Pat. No. 7,507,233 on Mar. 24, 2009 entitled "CRYOTHERAPY SYSTEM," filed Jun. 6, 2006 by Peter Littrup et al.; U.S. patent application Ser. No. 11/846,226, which issued as U.S. Pat. No. 7,921,657 on Apr. 12, 2011 entitled "METHODS AND SYSTEMS FOR CRYOGENIC COOLING," filed Aug. 28, 2007 by Peter Littrup et al.; U.S. patent application Ser. No. 12/018,403, which issued as U.S. Pat. No. 8,591,503 on Nov. 26, 2013 entitled "CRYOTHERAPY PROBE," filed Jan. 23, 2008 by Peter Littrup et al.; U.S. patent application Ser. No. 13/046,274, which issued as U.S. Pat. No. 8,387,402 on Mar. 5, 2013 entitled "METHODS AND SYSTEMS FOR CRYOGENIC COOLING," filed Mar. 11, 2011 by Peter Littrup et al.; U.S. patent application Ser. No. 14/087,947, which is pending entitled "CRYOTHERAPY PROBE," filed Nov. 22, 2013 by Peter Littrup et al.; U.S. patent application Ser. No. 12/744,001, which issued as U.S. Pat. No. 8,740,891, on Jun. 3, 2014 entitled "FLEXIBLE MULTI-TUBULAR CRYOPROBE," filed Jul. 29, 2010 by Alexei Babkin et al.; U.S. patent application Ser. No. 12/744,033, which issued as U.S. Pat. No. 8,740,892, on Jun. 3, 2014 entitled "EXPANDABLE MULTI-TUBULAR CRYOPROBE," filed Jul. 29, 2010 by Alexei Babkin et al. and U.S. patent application Ser. No. 14/915,632 entitled "ENDOVASCULAR NEAR CRITICAL FLUID BASED CRYOABLATION CATHETER AND RELATED METHODS," filed Sep. 22, 2014 by Alexei Babkin, et al., the contents of each of the above-identified U.S. patents/applications are incorporated herein by reference in their entireties for all purposes.

Figure 4:
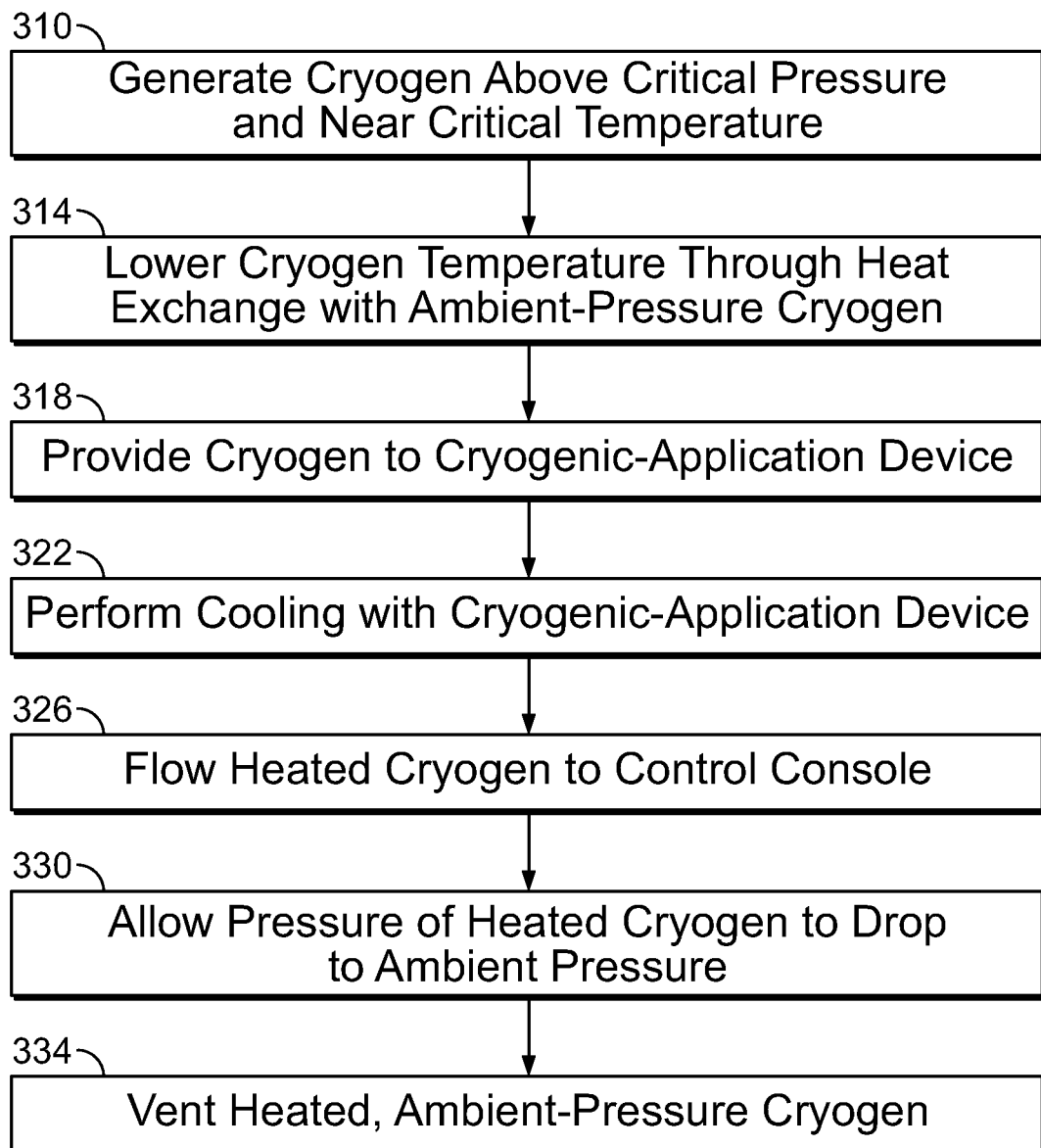
FIG. 4 provides a flow diagram that summarizes aspects of the cooling system of FIG. 2.

A method for cooling a target tissue in which the cryogen follows a thermodynamic path similar to that shown in FIG. 3 is illustrated with the flow diagram of FIG. 4. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For example, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Cryoablation Catheters

Figure 5:
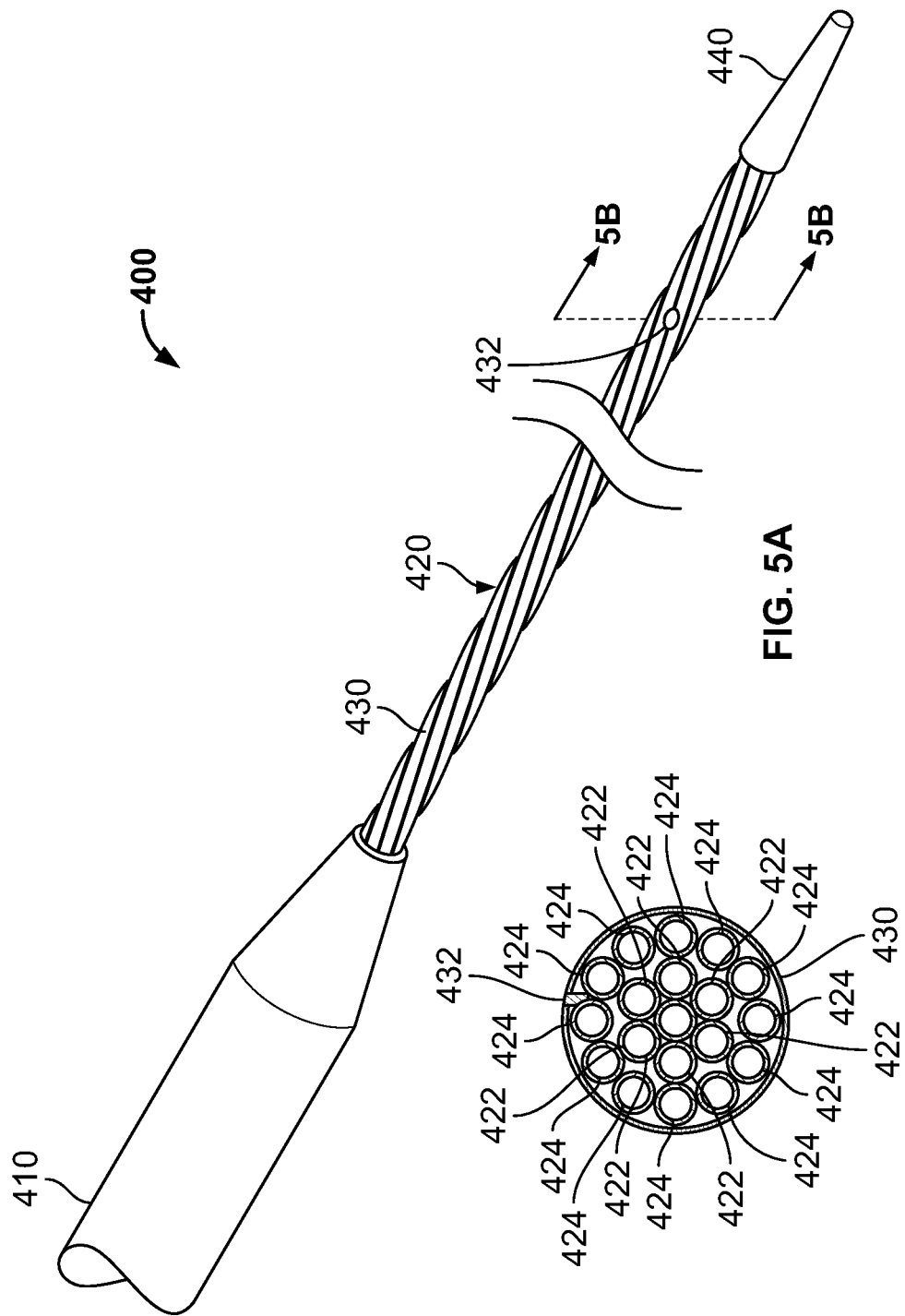
FIG. 5A is a perspective view of a cryoablation catheter, according to an embodiment of the invention.
FIG. 5B is a cross-sectional view taken along line 5B-5B of FIG. 5A.

Embodiments of the cryoablation apparatus of the present invention may have a wide variety of configurations. For example, one embodiment of the present invention is a flexible catheter 400 as shown in FIG. 5A. The catheter 400 includes a proximally disposed housing or connector 410 adapted to fluidly connect to a fluid source (not shown).

A plurality of fluid transfer tubes 420 are shown extending from the connector 410. These tubes include a set of inlet fluid transfer tubes 422 for receiving the inlet flow from the connector and a set of outlet fluid transfer tubes 424 for discharging flow from the connector 410.

In embodiments each of the fluid transfer tubes is formed of material that maintains flexibility in a full range of temperatures from −200° C. to ambient temperature. In embodiments, the fluid transfer tubes 420 are formed of annealed stainless steel or a polymer such as polyimide. In such configurations, the material may maintain flexibility at near critical temperature. In embodiments, each fluid transfer tube has an inside diameter in a range of between about 0.1 mm and 1 mm (preferably between about 0.2 mm and 0.5 mm). Each fluid transfer tube may have a wall thickness in a range of between about 0.01 mm and 0.3 mm (preferably between about 0.02 mm and 0.1 mm).

An end cap 440 is positioned at the ends of the fluid transfer tubes to provide fluid transfer from the inlet fluid transfer tubes to the outlet fluid transfer tubes. The endcap 440 is shown having an atraumatic tip. The endcap 440 may be any suitable element for providing fluid transfer from the inlet fluid transfer tubes to the outlet fluid transfer tubes. For example, endcap 440 may define an internal chamber, cavity, or passage serving to fluidly connect tubes 422,424.

With reference to FIG. 5B, an outer sheath 430 is shown surrounding the tube bundle 420. The outer sheath serves to hold the tubes in a tubular arrangement, and protect the construct from being penetrated or disrupted by foreign objects and obstacles.

A temperature sensor 432 is shown on the surface of the distal section. Temperature sensor may be a thermocouple to sense a temperature corresponding to the adjacent tissue, and sends the signal back through a wire in the tube bundle to the console for processing. Temperature sensor may be placed elsewhere along the shaft or within one or more of the fluid transport tubes to determine a temperature difference between inflow and outflow.

There are many configurations for tube arrangements. In embodiments the fluid transfer tubes are formed of a circular array, wherein the set of inlet fluid transfer tubes comprises at least one inlet fluid transfer tube 422 defining a central region of a circle and wherein the set of outlet fluid transfer tubes 424 comprises a plurality of outlet fluid transfer tubes spaced about the central region in a circular pattern. In the configuration shown in FIG. 5B, the fluid transfer tubes 422,424 fall within this class of embodiments.

During operation, the cryogen/cryogenic fluid arrives at the catheter through a supply line from a suitable cryogen source at a temperature close to −200° C. The cryogen is circulated through the multi-tubular freezing zone provided by the exposed fluid transfer tubes, and returns to the connector. Cryogen flows into the freeze zone through the inlet fluid transfer tube 422 and flows out of the freeze zone through the outlet fluid transfer tubes 424.

In embodiments, the nitrogen flow does not form gaseous bubbles inside the small diameter tubes under any heat load, so as not to create a vapor lock that limits the flow and the cooling power. By operating at the near critical condition for at least an initial period of energy application, the vapor lock is eliminated as the distinction between the liquid and gaseous phases disappears. After initially operating under near critical conditions, e.g., for nitrogen, at a temperature near the critical temperature of −147.15° C. and a pressure near the critical pressure of 3.396 MPa, the operating pressure may be decreased as is disclosed and described in commonly assigned U.S. patent application Ser. No. 14/919,681 entitled "PRESSURE MODULATED CRYOABLATION SYSTEM AND RELATED METHODS," filed Oct. 21, 2015 by Alexei Babkin, the contents of which are incorporated herein by reference in their entirety for all purposes.

A multi-tube design may be preferably to a single-tube design because the additional tubes can provide a substantial increase in the heat exchange area between the cryogen and tissue. Depending on the number of tubes used, cryoinstruments can increase the contact area several times over previous designs having similarly sized diameters with single shafts/tubes. However, embodiments of the invention are not intended to be limited to a single or multi-tubular design except where specifically recited in the appended claims.

Cryoablation Console

Figure 6:
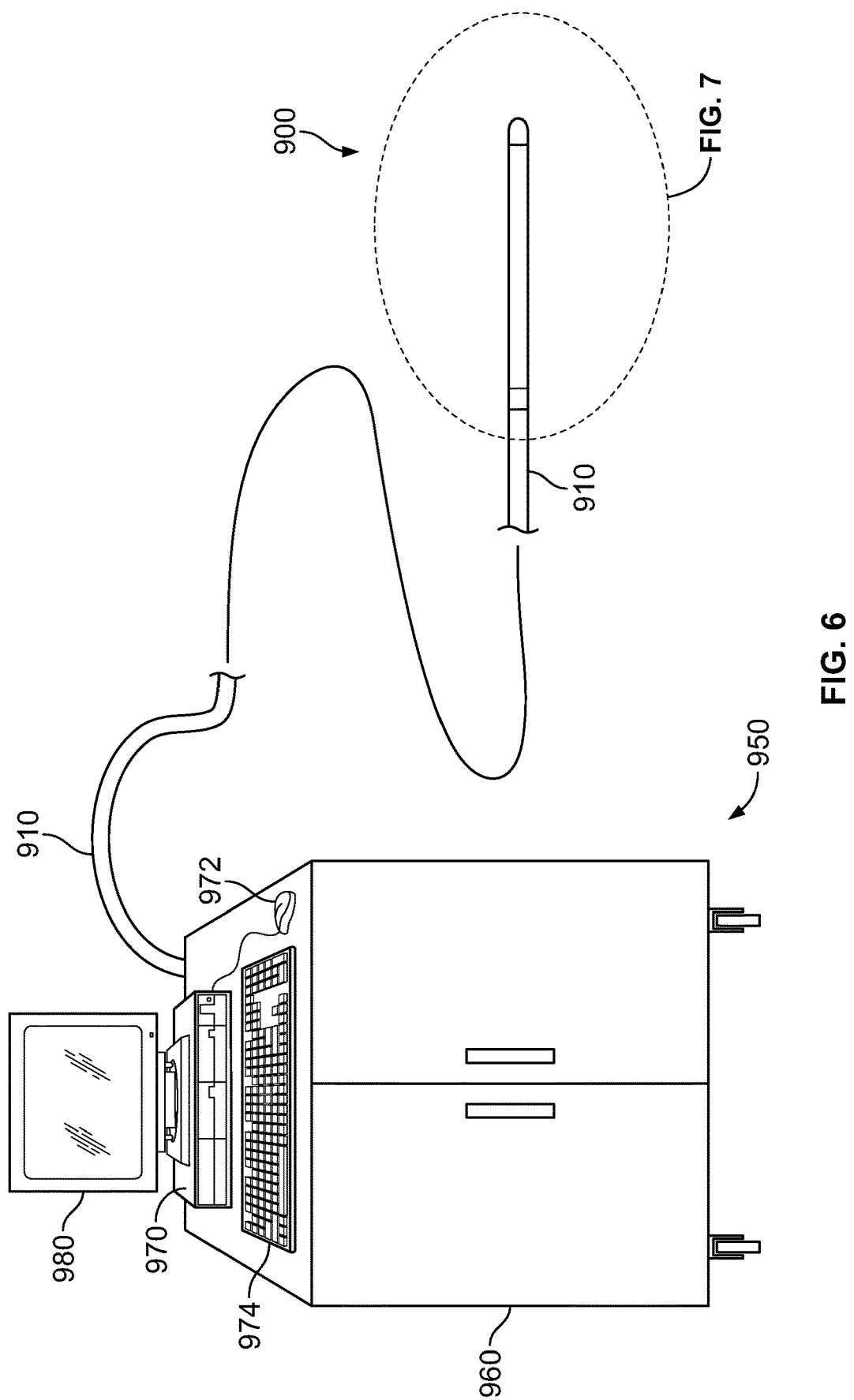
FIG. 6 is an illustration of a cryoablation system including a cryoablation catheter, according to an embodiment of the invention.

FIG. 6 illustrates a cryoablation system 950 having a cart or console 960 and a cryoablation catheter 900 detachably connected to the console via a flexible elongate tube 910. The cryoablation catheter 900, which shall be described in more detail below in connection with FIG. 7, contains one or more fluid transport tubes to remove heat from the tissue.

The console 960 may include or house a variety of components (not shown) such as, for example, a generator, controller, tank, valve, pump, etc. A computer 970 and display 980 are shown in FIG. 6 positioned on top of cart for convenient user operation. Computer may include a controller, timer, or communicate with an external controller to drive components of the cryoablation systems such as a pump, valve or generator. Input devices such as a mouse 972 and a keyboard 974 may be provided to allow the user to input data and control the cryoablation devices.

In embodiments computer 970 is configured or programmed to control cryogen flowrate, pressure, and temperatures as described herein. Target values and real time measurement may be sent to, and shown, on the display 980.

Figure 7:
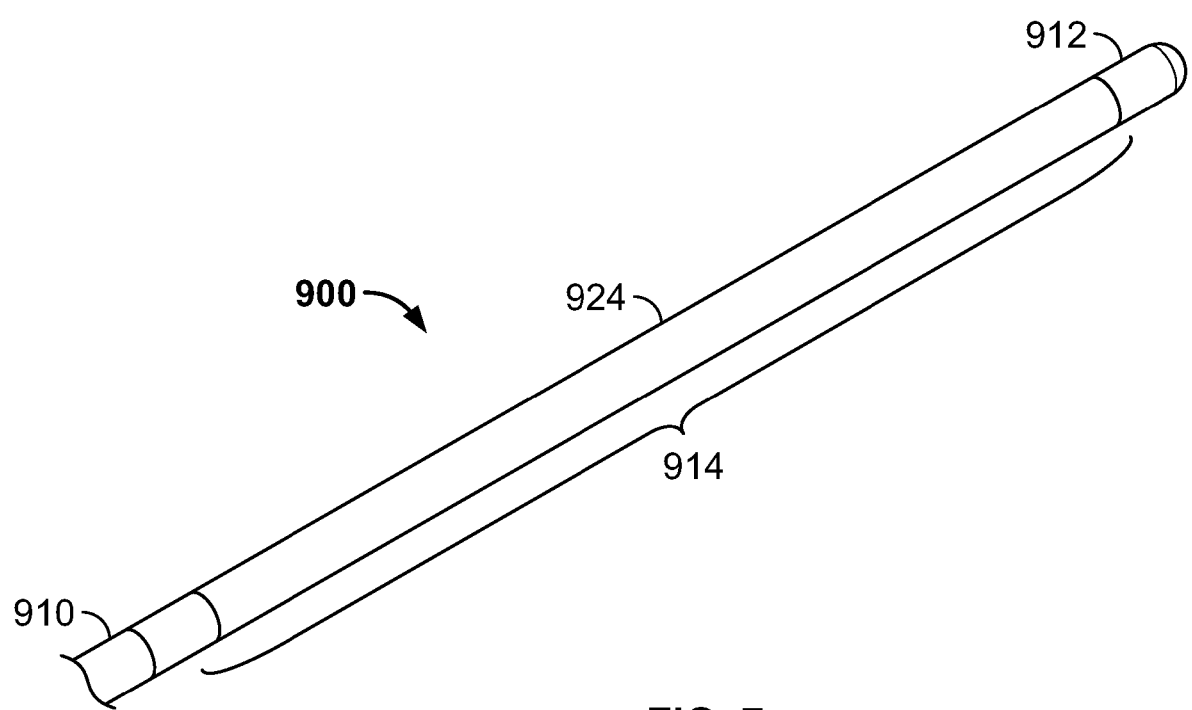
FIG. 7 is an enlarged perspective view of a distal section of the cryoablation catheter shown in FIG. 6.

FIG. 7 shows an enlarged view of distal section of cryoablation apparatus 900. The distal section 900 is similar to designs described above except that treatment region 914 includes a flexible protective cover 924. The cover serves to contain leaks of the cryogen in the event one of the fluid transport tubes is breached. Although a leak is not expected or anticipated in any of the fluid delivery transport tubes, the protective cover provides an extra or redundant barrier that the cryogen would have to penetrate in order to escape the catheter during a procedure. In embodiments the protective cover may be formed of metal.

Additionally, a thermally conducting liquid may be disposed within spaces or gaps between the transport tubes and the inner surface of the cover to enhance the device's thermal cooling efficiency during treatment. In embodiments the thermally conductive liquid is water.

Cover 924 is shown being tubular or cylindrically shaped and terminates at distal tip 912. As described herein, the cooling region 914 contains a plurality of fluid delivery and fluid return tubes to transport a cooling fluid through the treatment region 914 causing heat to be transferred/removed from the target tissue. In embodiments, the cryogen is transported through the tube bundle under physical conditions near the fluid's critical point in the phase diagram. The cover serves to, amongst other things, contain the cooling fluid and prevent it from escaping from the catheter in the event a leak forms in one of the delivery tubes.

Although a cover is shown in FIGS. 6-7, the invention is not intended to be so limited except as where recited in the appended claims. The apparatus may be provided with or without a protective cover and used to cool a target tissue.

Tube within Tube

FIG. 8 shows a partial view of a cryoablation catheter 1010 according to another embodiment of the invention having a protective means to mitigate leaks in the event a cooling fluid/cryogen escapes from the cryogen delivery tubes described above. In particular, catheter 1010 comprises a plurality or bundle 1012 of flexible multi-layer cryoenergy transfer tubes, each of which comprises two tubes in a coaxial arrangement, namely a tube within a tube.

Figure 9A:
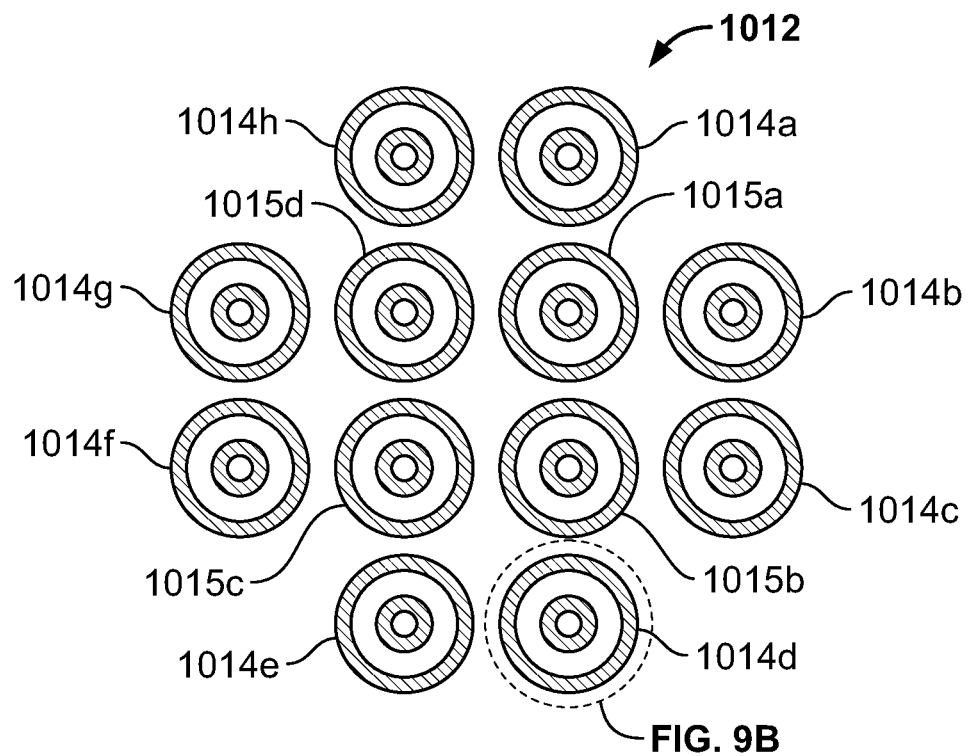
FIG. 9A is a cross-sectional view of an embodiment of a catheter shown in FIG. 8 taken along line 9A-9A in FIG. 9.

FIG. 9A shows a cross-sectional view taken along line 9A-9A of FIG. 8. The bundle 1012 of multilayer tubes is shown with the fluid delivery tubes 1014 and the fluid return tubes 1015 assembled in a parallel arrangement. The tube bundle 1012 is shown having 12 tubes/lines including four (4) fluid return tubes 1015a-1015d and eight (8) fluid delivery tubes 1014a-1014h. The fluid delivery tubes 1014a-1014h form a perimeter around the fluid return tubes 1015a-1015d. This arrangement ensures that colder delivery fluid/cryogen is adjacent to the tissue to be ablated/frozen and warmer return fluid/cryogen is shielded from the tissue to be ablated/frozen.

Figure 9B:
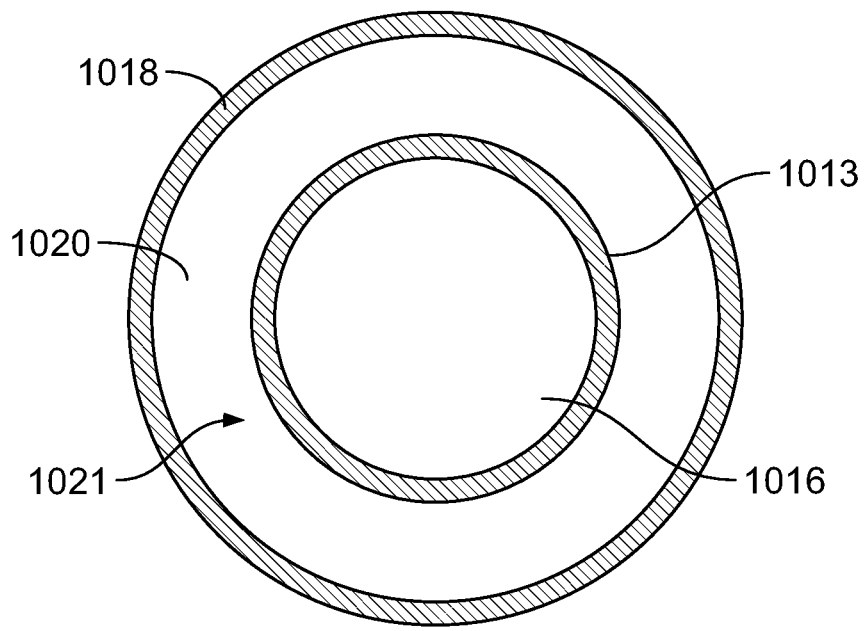
FIG. 9B is an enlarged view of one of the multi-layered tubes shown in FIG. 9A.

FIG. 9B shows an enlarged cross-sectional view of fluid delivery tube 1014d of FIG. 9A. The first or inner tube 1013 is shown coaxially surrounded by a second or outer tube 1018. A space or gap 1020 between the exterior surface of the inner tube 1013 and the interior surface of the outer tube 1018 is capable of being filled with a thermally conductive media 1021 as described herein. In embodiments, the gap 1020 has an annular shape. All of the fluid delivery tubes 1014 as well as the fluid return tubes 1015 can have a similar tube within a tube construction.

In the event of a leak of the cooling fluid 1016 or breach of the inner tube 1013 during use, the cooling fluid 1016 is contained within the gap 1020 between the inner tube 1013 and the outer tube 1018. This tube within a tube feature adds an additional safety element to the device as any leaking fluid/cryogen 1016 is contained within the catheter and is prevented from entering the patient. In some embodiments, a pressure sensor/device or gauge may be incorporated to monitor the pressure of the thermally conductive media 1021 in the gap 1020. Therefore, if fluid/cryogen 1016 breaches the inner tube 1013 and leaks into the gap 1020, the pressure in the gap 1020 and hence, the conductive media 1021 will increase. Should a change in pressure occur above a threshold limit, the system can be programmed to halt ablation thereby preventing potential harm to a patient and/or notify the user/physician of this change in pressure.

The inner tube 1013 may be fabricated and made from materials as described herein in connection with other flexible tubes for transporting the cooling fluid.

The outer tube 1018 material should also be flexible to enable elastic deflection of the distal treatment section to allow the distal treatment section to transform its shape as disclosed herein. In some embodiments, the outer tube is not inflatable, distensible nor expandable such that its size and shape remains substantially unaffected by the presence of the thermally conductive media 1021 contained therein. Non-limiting exemplary materials for the outer tube 1018 include polymers and metals or alloys. An example of an outer tube 1018 material is Nitinol or polyimide.

The number of tubes forming the tubular bundle 1012 may vary widely. In some embodiments, the tubular bundle 1012 includes 5-15 tubes, and more preferably, includes between 8-12 tubes comprising fluid delivery tubes 1014 and fluid return tubes 1015.

Figure 14:
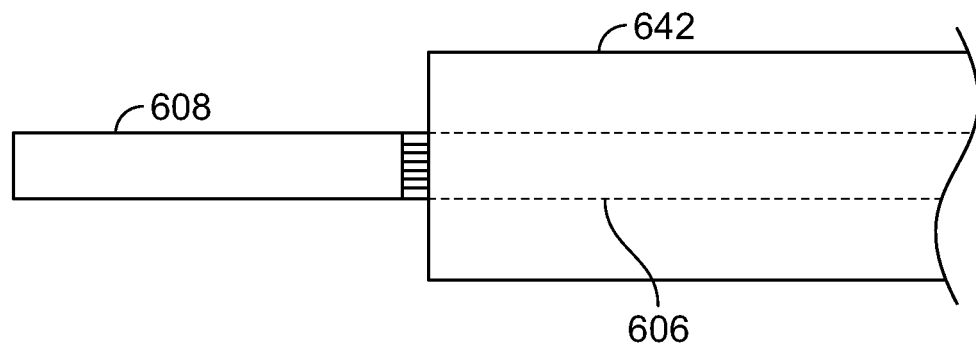
FIGS. 14-15 illustrate sequential deployment of the distal section of catheter shown in FIG. 11 from an outer sheath member.
Figure 16:
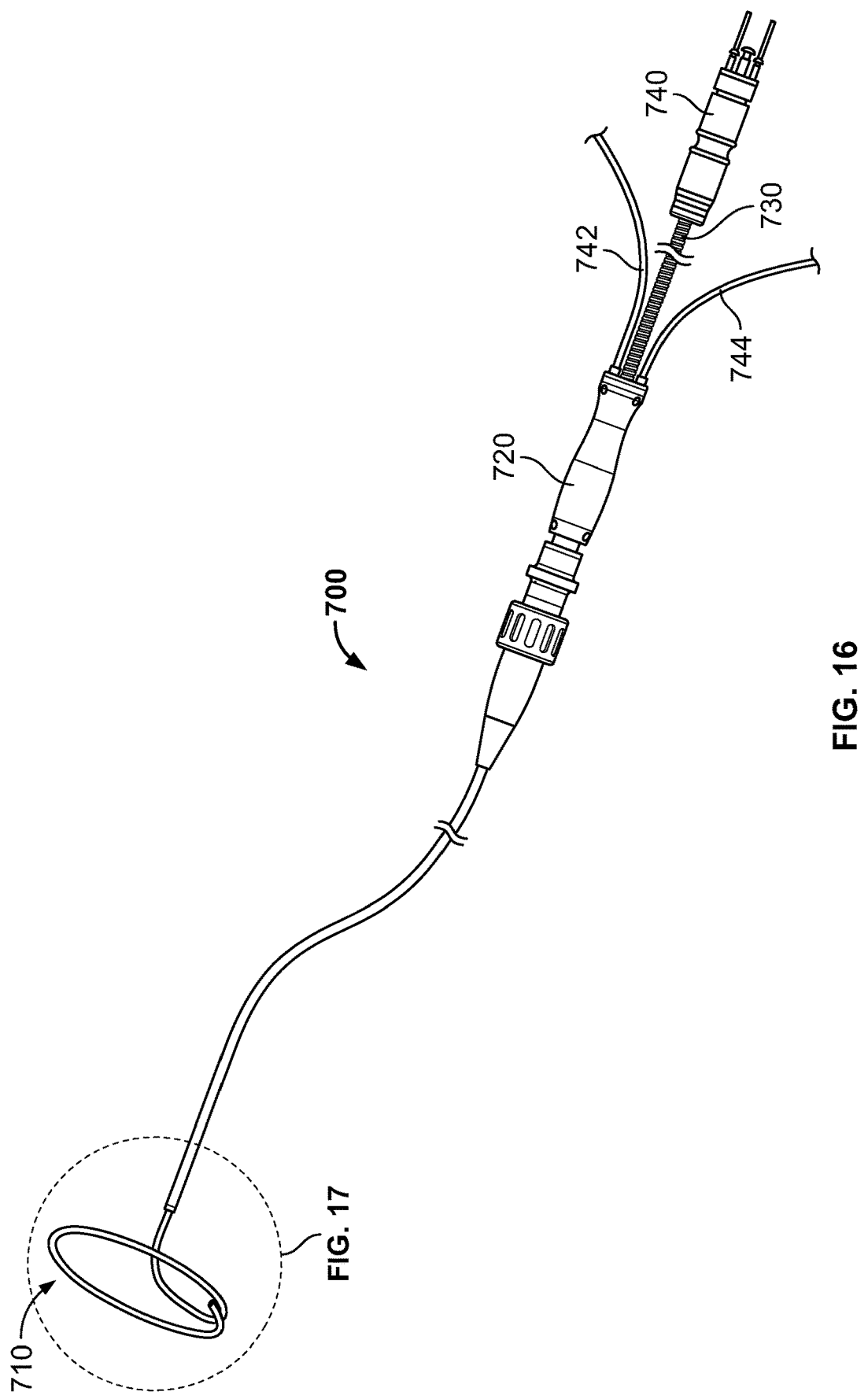
FIG. 16 is a perspective view of another embodiment of a cryoablation catheter having a flexible distal treatment section.

The cross-sectional profile of the tube bundle 1012 may also vary. Although FIG. 9A shows a substantially circular profile, in embodiments, the profile may be rectangular, square, cross or t-shaped, annular or circumferential, or another shape profile, including some of the arrangements described above. The tubes may also be braided, woven, twisted, or otherwise intertwined together, as depicted in FIGS. 9, 14 and 16 of commonly assigned U.S. patent application Ser. No. 14/915,632 entitled "ENDOVASCULAR NEAR CRITICAL FLUID BASED CRYOABLATION CATHETER AND RELATED METHODS," filed Sep. 22, 2014 by Alexei Babkin, et al., the entire contents of which are incorporated herein by reference for all purposes.

The diameter of the freezing section or tubular bundle may vary. In embodiments, the diameter of the bundle ranges from about 1-3 mm, and is preferably about 2 mm.

Figure 9C:
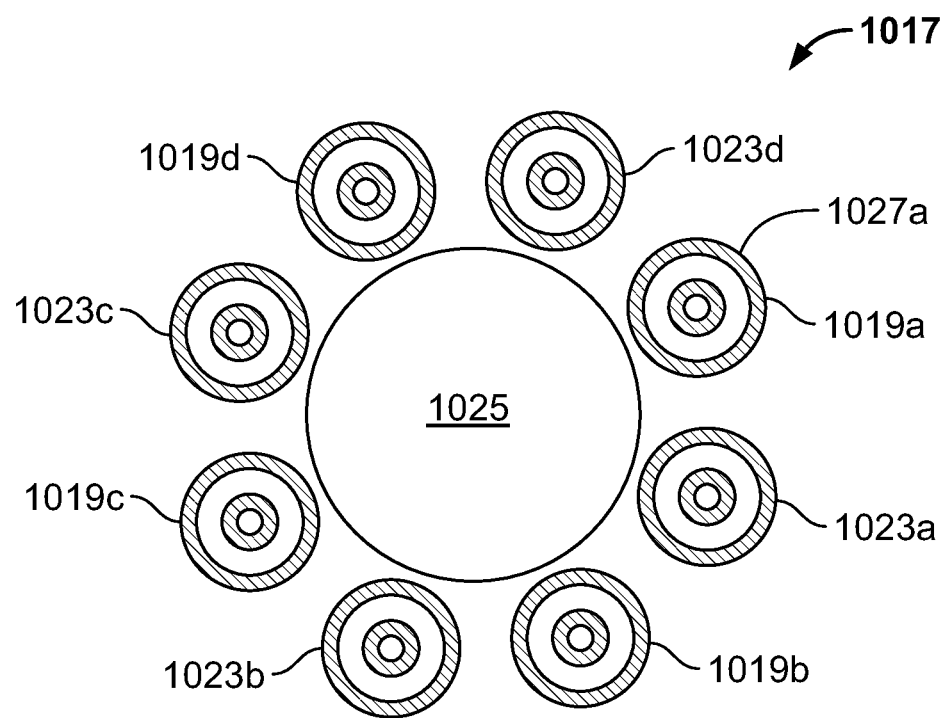
FIG. 9C is a cross sectional view of another embodiment of a cryoablation catheter.

FIG. 9C shows a cross-section of a cryoablation catheter having another tubular arrangement 1017. The eight (8) tubular elements (1019a-1019d and 1023a-1023d) are spaced or distributed circumferentially about a core element 1025. Preferably, as shown, fluid delivery elements/tubes (1019a-1019d) and fluid return elements/tubes (1023a-1023d) alternate along the circumference of the catheter.

Each inner tubular element (e.g., 1019a) includes an outer tubular element (e.g., 1027a) coaxially surrounding the inner tubular element thereby creating a space or gap which can be filled with a thermally conductive media/fluid as described with respect to FIG. 9B.

Steering elements, sensors and other functional elements may be incorporated into the catheter. In embodiments, steering elements are incorporated into a mechanical core such as the mechanical core 1025 shown in FIG. 9C.

Figure 10A:
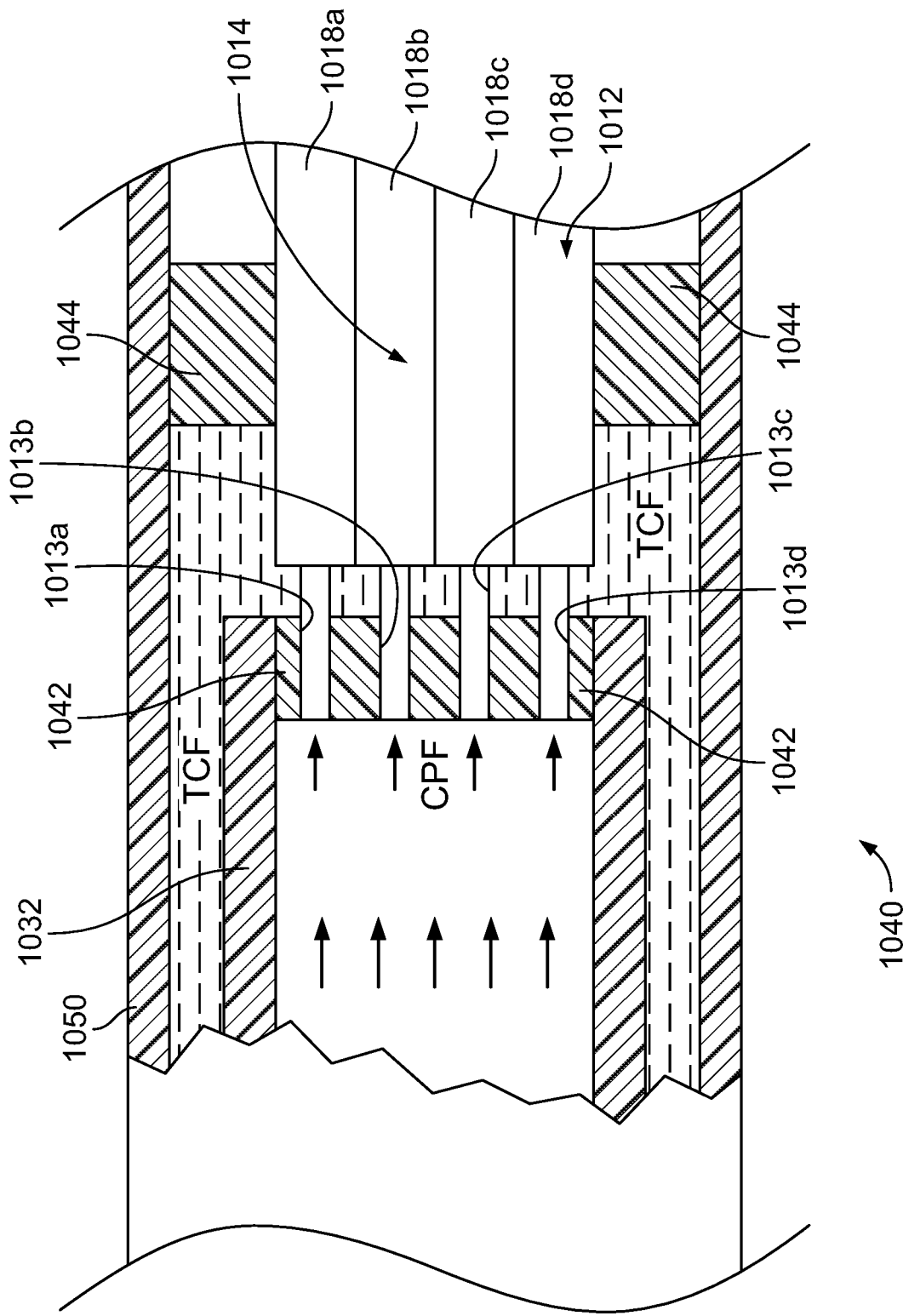
FIG. 10A is a partial sectional view of an embodiment of a catheter shown in FIG. 8.

FIG. 10A shows an enlarged cut-away view of the catheter at detail 10A in FIG. 8, illustrating tube bundle 1012 fluidly connected to the end portion 1040 of an intermediate section of the catheter 1010.

Figure 10B:
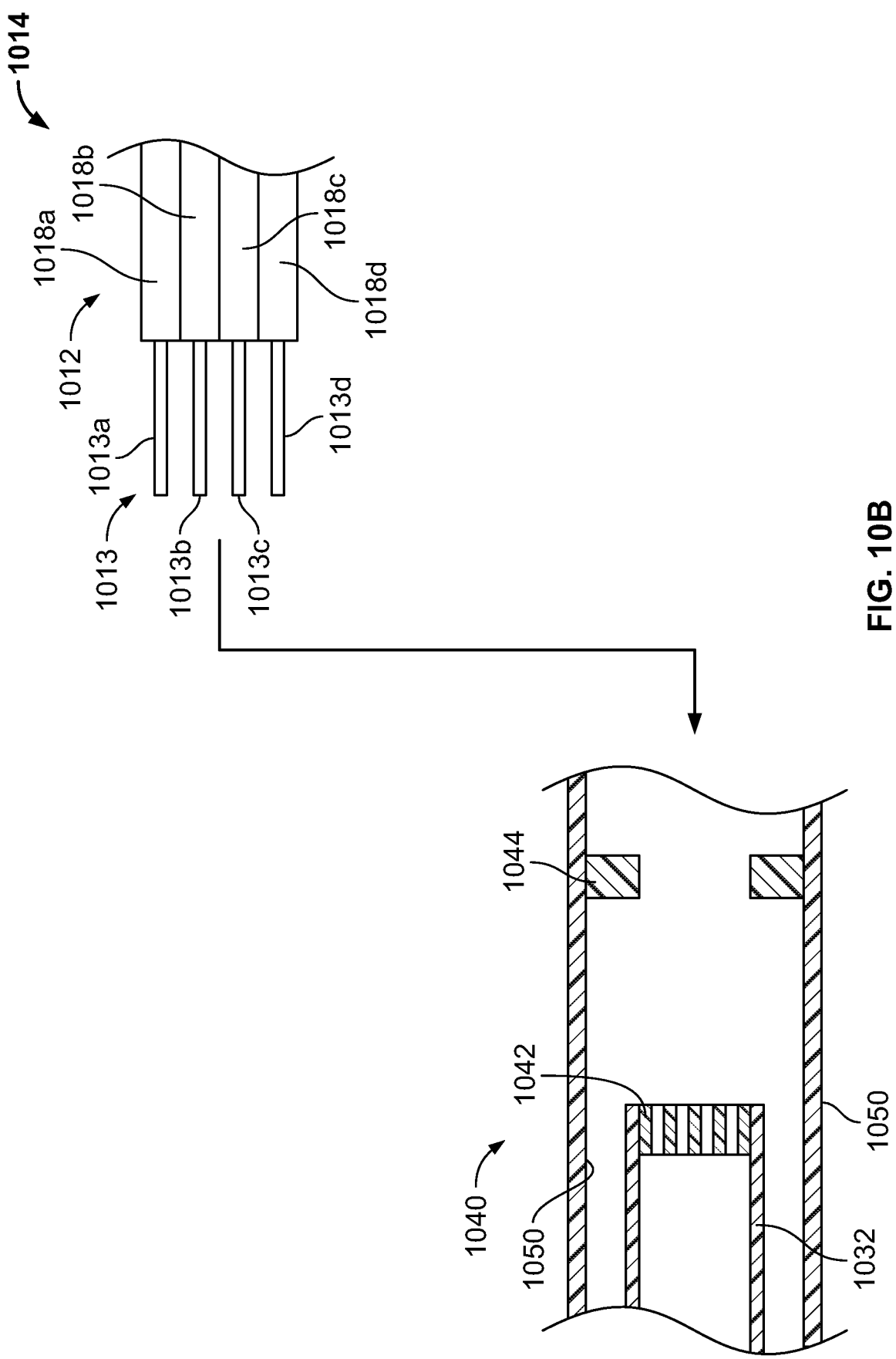
FIG. 10B is a partial exploded view of the proximal ends of the tube elements and the distal end of the intermediate section of an embodiment of a catheter shown in FIG. 8.

FIG. 10B shows an exploded view of a proximal section of the tube bundle 1012 and the intermediate section of catheter 1040. Tube bundle 1012, having inner tubular elements 1013a-1013d extending beyond outer tubular elements/covers 1018a-1018d of fluid delivery lines 1014, can be inserted into intermediate section of catheter 1040.

With reference to FIGS. 10A-10B, fluid delivery lines 1014 are shown bundled together and inserted/joined to main line 1032. An adhesive plug 1042 or seal, gasket, or stopper, etc. may be applied to facilitate and ensure a fluid seal between the tube members. The cooling power fluid (CPF) is transported to the fluid delivery lines 1014 from the fluid delivery main line 1032.

The proximal ends of outer tubular elements/covers 1018a-d, which are offset from proximal ends of inner tubular elements 1013a-d, are shown inserted into intermediate section 1040 of catheter such that the thermally conductive fluid (TCF) within lumen 1050 can fill gaps 1020 (FIG. 9B) of each of the multi-layer cryoenergy tubular elements. An adhesive plug 1044 (weld or bond) may be applied to facilitate a fluid tight and robust connection. Press fits, heat, and other fabrication techniques can be applied to join components as is known to those of skill in the art.

FIG. 11 shows another cryoablation catheter 500 including a distal treatment section 510, a handle 520, and an umbilical cord 530. The proximal end of the umbilical cord 530 terminates in connector 540, which is inserted into receptacle port 560 on console 550.

One or more ancillary connector lines 570 are shown extending proximally from the handle 520. The tubular lines 570 may serve to provide various functionality including without limitation (a) flushing; (b) vacuum; (c) thermally conductive liquid described above; and/or (d) temperature and pressure sensor conductors.

The catheter 500 is also shown having electrical connector 580 extending proximally from the handle 520. Electrical connector 580 may be coupled to an EP recording system for analyzing electrical information detected in the distal treatment section 510. Examples of systems for analyzing the electrical activity include, without limitation, the GE Healthcare CardioLab II EP Recording System, manufactured by GE Healthcare, USA and the LabSystem PRO EP Recording System manufactured by Boston Scientific Inc. (Marlborough, Mass.). The recorded electrical activity may also be used to evaluate or verify the continuous contact with the target tissue as described in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes.

Figure 12:
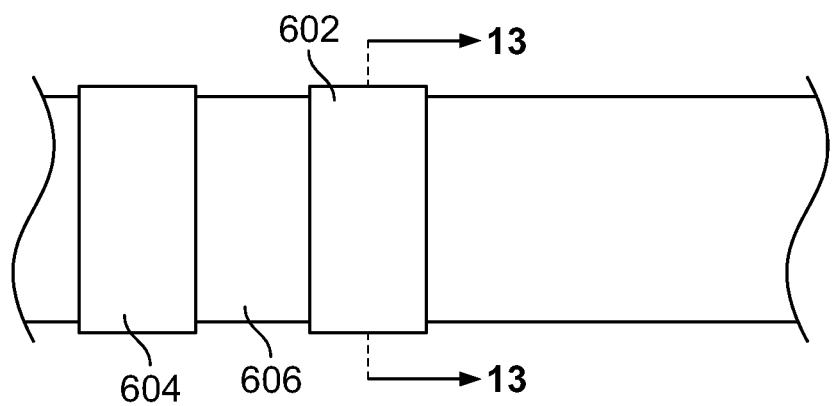
FIG. 12 is an enlarged view of a portion of the distal section shown in FIG. 11.

FIG. 12 shows an enlarged view of a portion of the distal section 510 of the catheter 500. Ring-shaped electrodes 602, 604 are circumferentially disposed about shaft 606. Although two electrodes are shown, more or less electrodes may be present on the shaft for sensing electrical activity. In embodiments, up to 12 electrodes are provided on the shaft. In one embodiment, 8 electrodes are axially spaced along the shaft 606.

Figure 13:
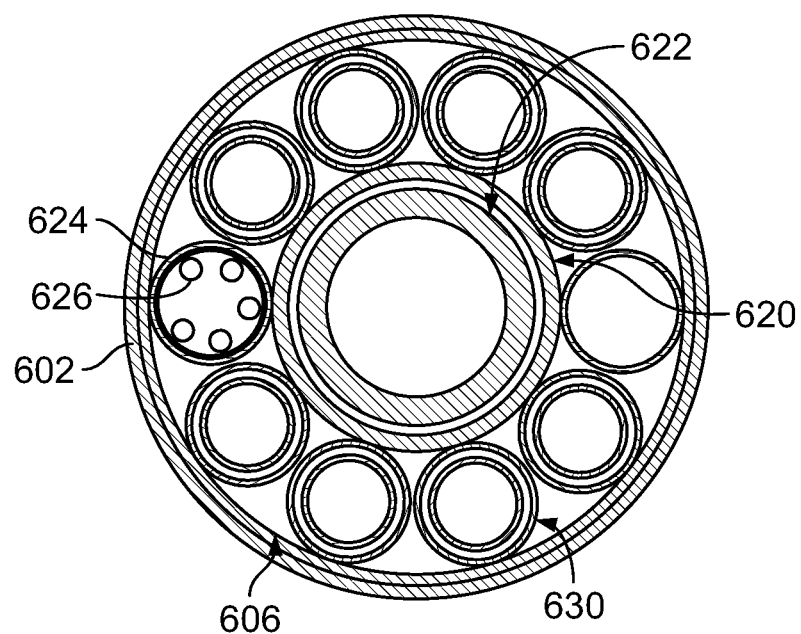
FIG. 13 is a cross sectional view of the catheter shown in FIG. 12 taken along line 13-13 in FIG. 12.

FIG. 13 is a cross section of the catheter shown in FIG. 12 taken along line 13-13. The catheter shaft is shown having a mechanical core 620 extending along the central axis, and a plurality of energy delivering tube constructs 630 extending parallel and circumferentially disposed about the mechanical core.

Each tube construct 630 is shown having dual layers as described above in connection with FIGS. 8-9 and a thermally conductive liquid layer disposed there between.

A tubular line 624 is shown for housing conducting wires 626 for the various sensors described herein.

The mechanical core 620 may be constructed to provide a preset shape to the catheter distal treatment section. With reference to FIG. 13, the mechanical core includes a metal tubular member 622 having a preset shape. The preset shape matches the target anatomy to make continuous contact with the target anatomy. An exemplary material for the preset tubular element 622 is Nitinol. FIG. 13 also shows an exterior layer or cover concentrically surrounding the Nitinol tube. The exterior cover may be a flexible polymer such as, for example, PET. Collectively, the inner PET layer 620 and outer shaft layer 606 form a fluidly-sealed annular chamber to house the plurality of tubular constructs 630.

Figure 15:
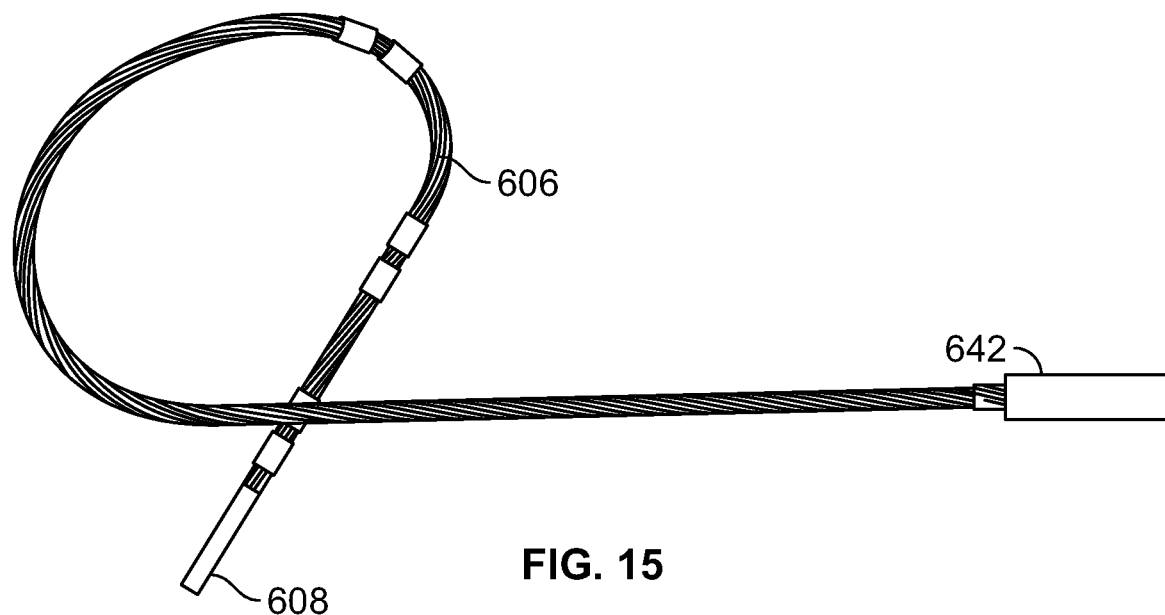

With reference to FIGS. 14-15, a catheter 608 is shown being deployed from an outer sheath 642. Initially, catheter distal section 606 is disposed within a lumen of external sheath 642, and prohibited from assuming its preset shape. The distal section 606 and external sheath 642 are moved axially relative to one another. For example, the catheter may be ejected from the sheath. Once the catheter is free from constraint, it assumes the preset shape as shown in FIG. 15.

Mechanical core assembly biases the shape of the catheter distal section 608, forcing the energy delivering elements into a curvilinear shape. In embodiments, the catheter shape is adapted to create lesions in the right atrium useful in treating atrial flutter. The shape shown in FIG. 15, for example, is a single loop or elliptical shape which has curvature to match target zones of tissue in the right atrium useful in treating atrial flutter. Additional apparatus and methods for treating atrial flutter are described in commonly assigned U.S. Patent Application No. 61/981,110, filed Apr. 17, 2014, now International Patent Application No. PCT/US2015/024778, filed Oct. 21, 2015 entitled "ENDOVASCULAR NEAR CRITICAL FLUID BASED CRYOABLATION CATHETER HAVING PLURALITY OF PREFORMED TREATMENT SHAPES," the contents of both of which are incorporated herein by reference in their entireties for all purposes.

FIG. 16 shows another cryoablation catheter 700 including a distal treatment section 710, a handle 720, and an umbilical cord 730 which terminates in connector 740. Similar to the system described above in connection with FIG. 11, connector 740 may be inserted into a receptacle port on a console.

Additional lines 742, 744 are shown extending proximally from handle. Lines 742, 744 provide various functionalities to the distal treatment section 710 during a procedure. Example functionalities include, without limitation, temperature, EP recording, pressure, fluid flush, source liquids, etc.

Figure 17:
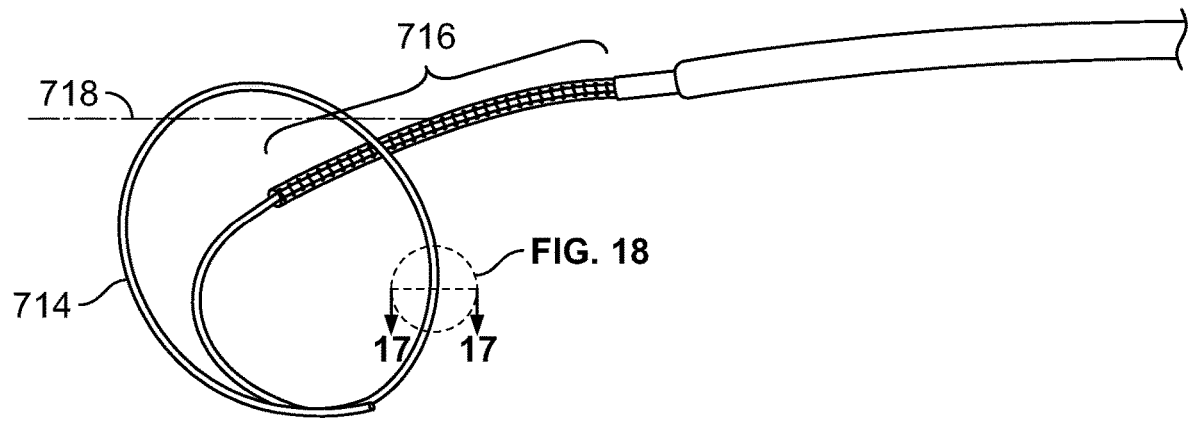
FIG. 17 is an enlarged view of the distal section of the catheter shown in FIG. 16.

FIG. 17 is an enlarged view of the catheter distal section following deployment. The treatment section is shown having a generally looped or elliptical shape 714. An intermediate section 716 is shown providing a bend or articulation from central axis 718. Such functionality aids in positioning the treatment section in continuous direct contact with the tissue. In embodiments, the shape is configured to create complete PVI in the left atrium.

Figure 18:
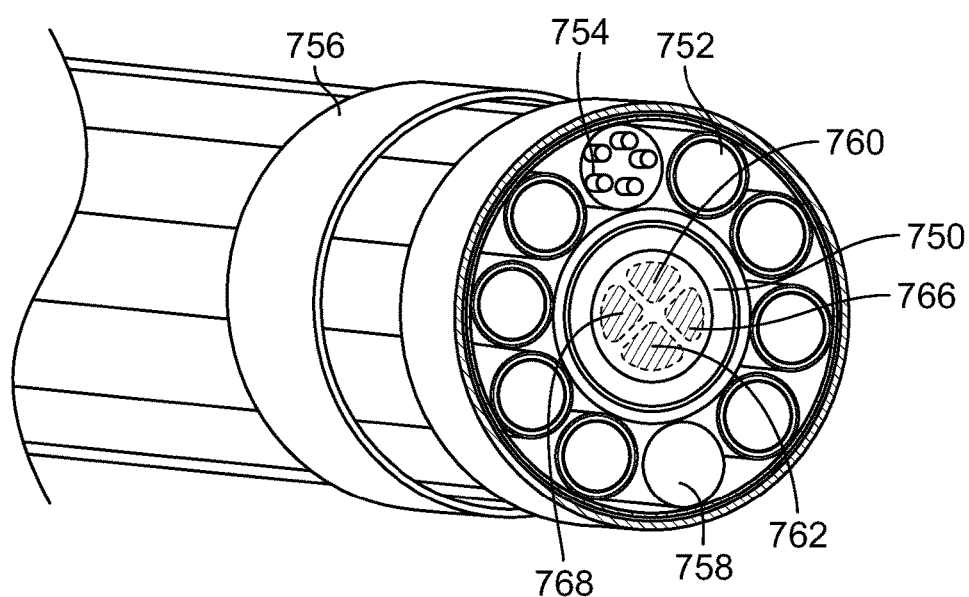
FIG. 18 is a cross sectional view of the catheter shown in FIG. 17 taken along line 17-17 in FIG. 17.

FIG. 18 is an enlarged cross sectional view of a portion of the distal treatment section. The catheter shaft is shown having a mechanical core 750 extending along the central axis, and a plurality of energy delivering tube constructs 752 extending parallel and circumferentially about the mechanical core. One or more spare tubular elements 754,758 can be incorporated into the perimeter space in combination with energy delivery elements. Tubular element 754 holds a plurality of electrical conductors to transmit electrical activity from sensors or ring electrodes 756 present on the distal treatment section. Tubular element 758 may provide vacuum or liquid to the catheter for various functions described herein.

Mechanical core 750 is shown extending axially through the treatment section and comprising a plurality of members 760, 762 which extend through the distal treatment section to bias the distal section into a preset shape such as the loop shape shown in FIG. 17. In particular, in embodiments, the mechanical core can include a biased shape element 760 such as a Nitinol wire, and an axially movable control member 762 connected to a distal tip of the treatment section to adjust the curvature of the preset shape. Core may include additional lumens 766,768 if desired. The mechanical core acts to shape the distal treatment section to a first preset loop shape, and can be further adjusted by the control member to make continuous contact with a target tissue surface.

FIGS. 19A-19D illustrate sequentially deployment of an ablation catheter 810 from a first arcuate shape having a slight bend to a second configuration having a complete ring or circular shape 820. The shape is assumed once the catheter treatment section is not constrained by the outer sheath 812.

Figure 19A:
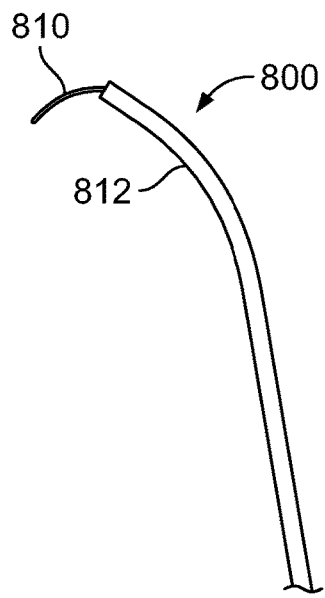
FIGS. 19A-19D show deployment of a distal section of the catheter, according to an embodiment of the invention.
Figure 19B:
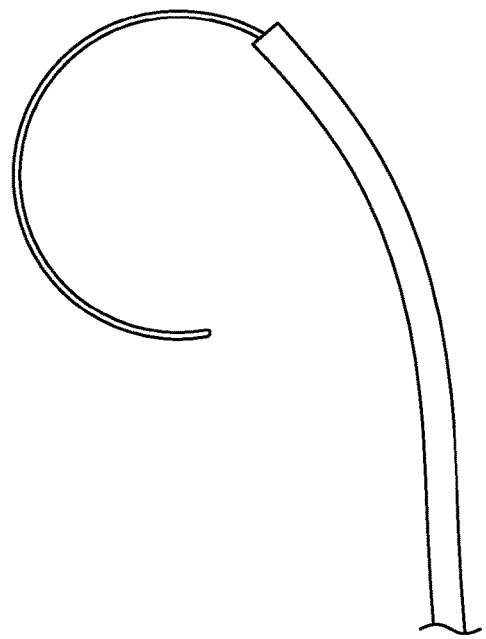
Figure 19C:
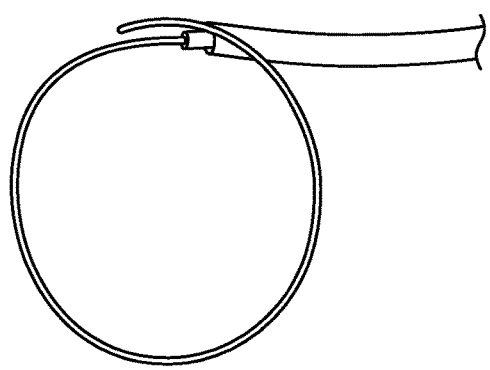
Figure 19D:
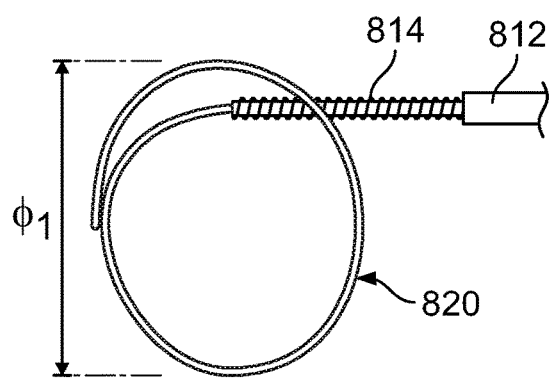
Figure 20A:
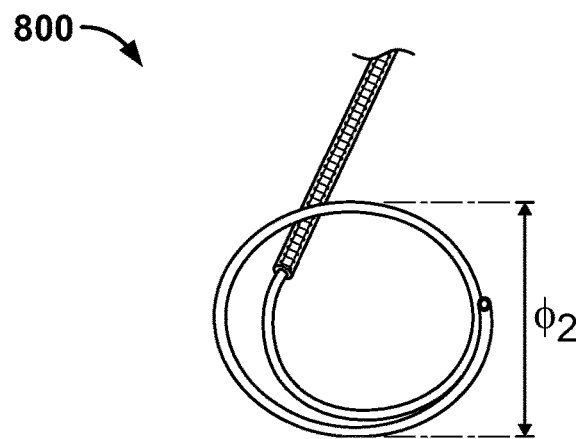
FIGS. 20A-20B show reducing the diameter of the preset loop shape of the catheter shown in FIG. 19D.
Figure 20B:
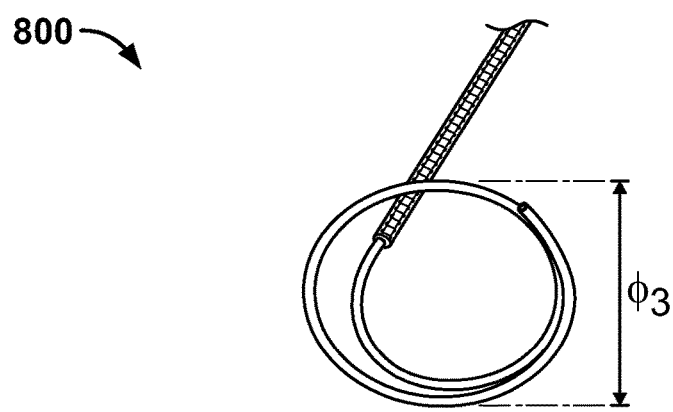

FIGS. 20A-20B show an enlarged view of the catheter 800 of FIG. 19D except that the loop has been adjusted by reducing its diameter $\Phi_1$. As described herein, a control member extending through the shaft of the distal treatment section is pulled to reduce the diameter of the preset loop $\Phi_1$ to diameter $\Phi_2$ as shown in FIG. 20A. FIG. 20B shows the loop adjusted to an even smaller diameter $\Phi_3$ than that shown in FIG. 20A.

The diameter $\Phi$ of the loop may vary. In embodiments, the diameter of the loop is controlled to range from 2 cm to 5 cm, and in embodiments, preferably about 2-3 cm.

Figure 21A:
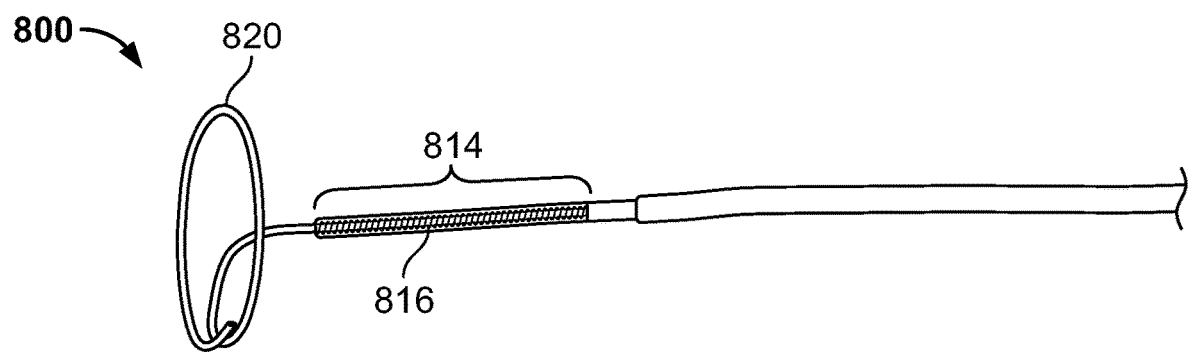
FIGS. 21A-21C show articulation of a catheter shaft, according to an embodiment of the invention.
Figure 21B:
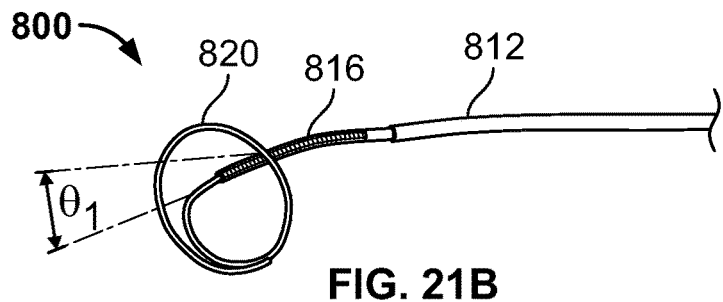
Figure 21C:
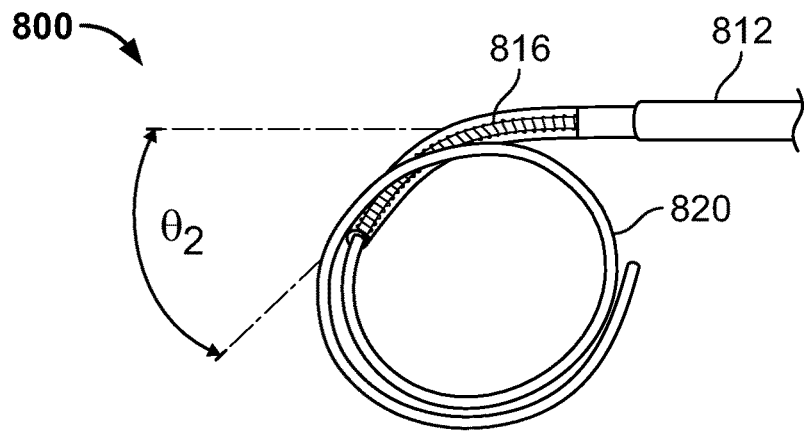

FIGS. 21A-21C show sequentially articulation of the intermediate section 814 of the catheter. The intermediate section 814 is shown having an outer support or reinforcing structure 816. In embodiments, the support layer 816 is a spring or coil.

FIG. 21A shows catheter intermediate section 814 substantially straight or aligned with the shaft axis.

FIG. 21B shows catheter intermediate section having a slight articulation forming angle $\theta_1$ with shaft axis.

FIG. 21C shows catheter intermediate section having further articulation $\theta_2$ with shaft axis. The degree of articulation may vary and be adjusted by the physician as described below. In embodiments, the degree of articulation is up to 120 degrees from the central shaft axis, and more preferably up to about 90 degrees.

Figure 22A:
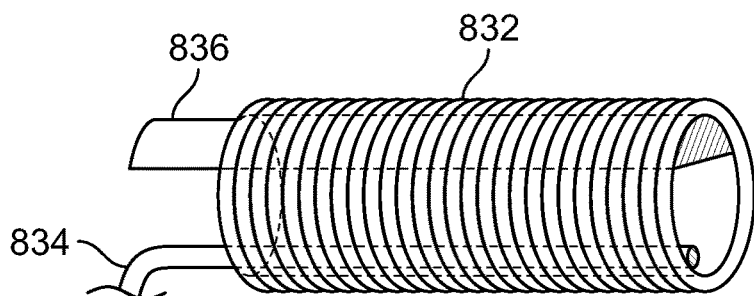
FIGS. 22A-22B show components of an intermediate section of the catheter.
Figure 22B:
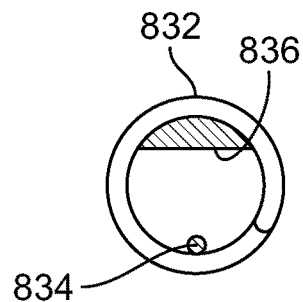

FIGS. 22A-22B show examples of components/structures for articulating the intermediate section. The components include a coil 832, second pull wire 834, and spine 836. The pull wire 834 is fixed to a distal location of the intermediate section. Pulling on the pull wire results in deflecting or articulating the coil 832. Spine 836 is shown diametrically opposite the pull wire. The spine serves to bias the direction that the catheter bends when the pull wire is retracted and serves to return the catheter to its straightened position when the pull wire is released. In particular, when the pull wire is retracted, the catheter bends towards the pull wire along a plane including the pull wire, central coil axis, and the spine.

The various articulating components/structures may be made of a wide variety of materials. Exemplary materials include without limitation Nitinol, stainless steel, or other materials having the functionality described herein. Additionally, the components may be fabricated from wire, tubular elements, or sheets of stock material. In one embodiment, the coil and spring are integrally formed from a sheet of metal alloy. The desired shape may be machined or laser cut to create the spine and rib elements, allowing for biased articulation. See also US Patent Publication No. 2003/

0195605, filed May 30, 2003, entitled "Cryogenic Catheter with Deflectable Tip" to Kovalcheck et al. for further details describing catheters comprising a spring, pull wire and spine for controlling deflection.

Figure 23A:
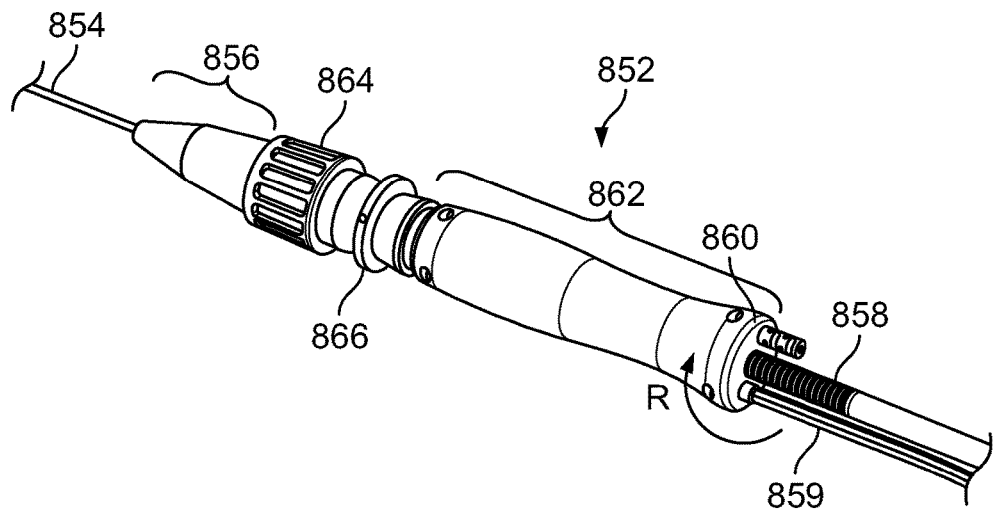
FIG. 23A shows a perspective view of a handle for an ablation catheter, according to an embodiment of the invention.

FIG. 23A shows a perspective view of a handle 852 of an ablation catheter. A flexible catheter shaft 854 extends from a distal section 856 of the handle. Umbilical cord 858 and various other functional lines and connectors 859 are shown extending proximally from a proximal section 860 of handle.

Handle 852 is shown having an ergonomic design including a smooth gently curved intermediate section 862 that allows a user to conveniently hold the handle.

Handle is shown comprising a knob 864 which may be rotated relative to the handle body to control the diameter of the deployed loop as described above. An axially movable hub 866 is shown proximal to the knob. Movement of the hub 866 forward or backwards serves to adjust or articulate the deployed shaft as described above. Additionally, handle may be rotated as a whole to steer the catheter in one direction or another. Collectively, the handle provides a convenient and semi automatic apparatus to turn, articulate, and control the diameter or size of the deployed structure.

Figure 23B:
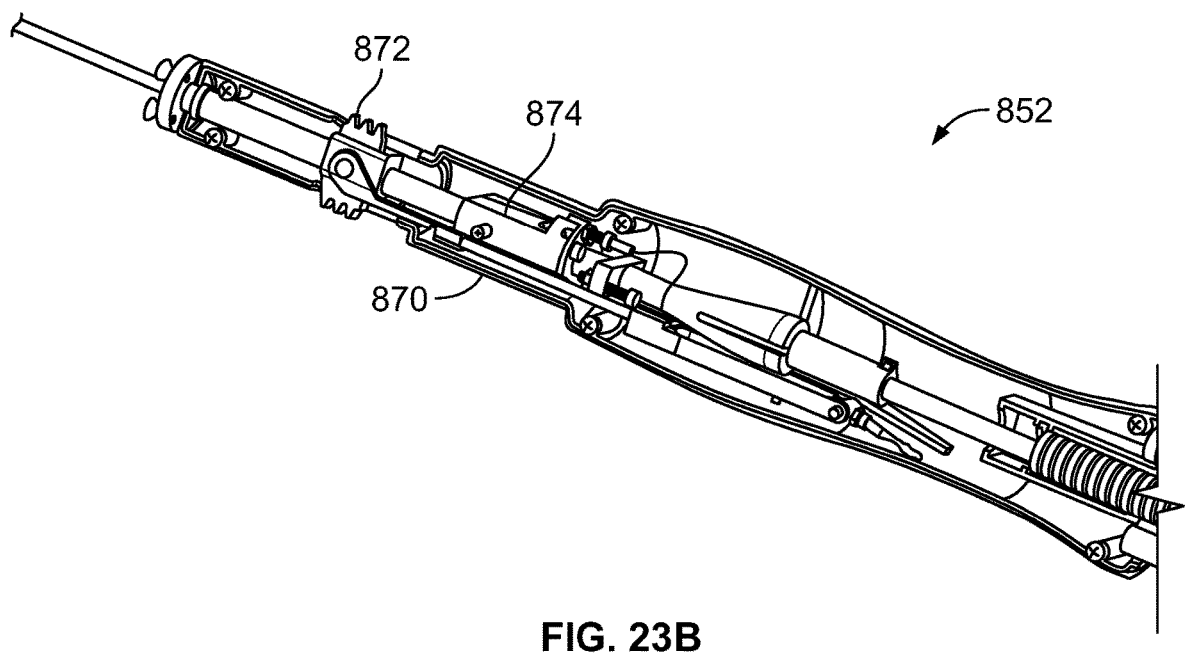
FIG. 23B shows a partial perspective view of the handle shown in FIG. 23A with the exterior removed.

FIG. 23B shows a partial perspective view of the handle shown in FIG. 23A with the exterior removed for clarity. A segment of an external thread or teeth 872 are shown. The teeth 872 mate with grooves or thread in the knob 864. The teeth are linked to a first control member described above for changing the shape or diameter of the loop. As the knob is rotated, the pull wire is moved simultaneously.

Slider 874 is also shown in handle. Slider 874 is joined to hub 866 such that movement of the hub causes the slider to move. Slider is also linked to a second control member as described above for articulating the catheter shaft. When the exterior hub is moved by the physician, the second control member articulates the shaft.

Although the handle is shown having a knob, hub, and slider, the invention is not intended to be so limited. The invention can include other levers, gears, buttons, and means for causing the above described functionality.

Figure 24:
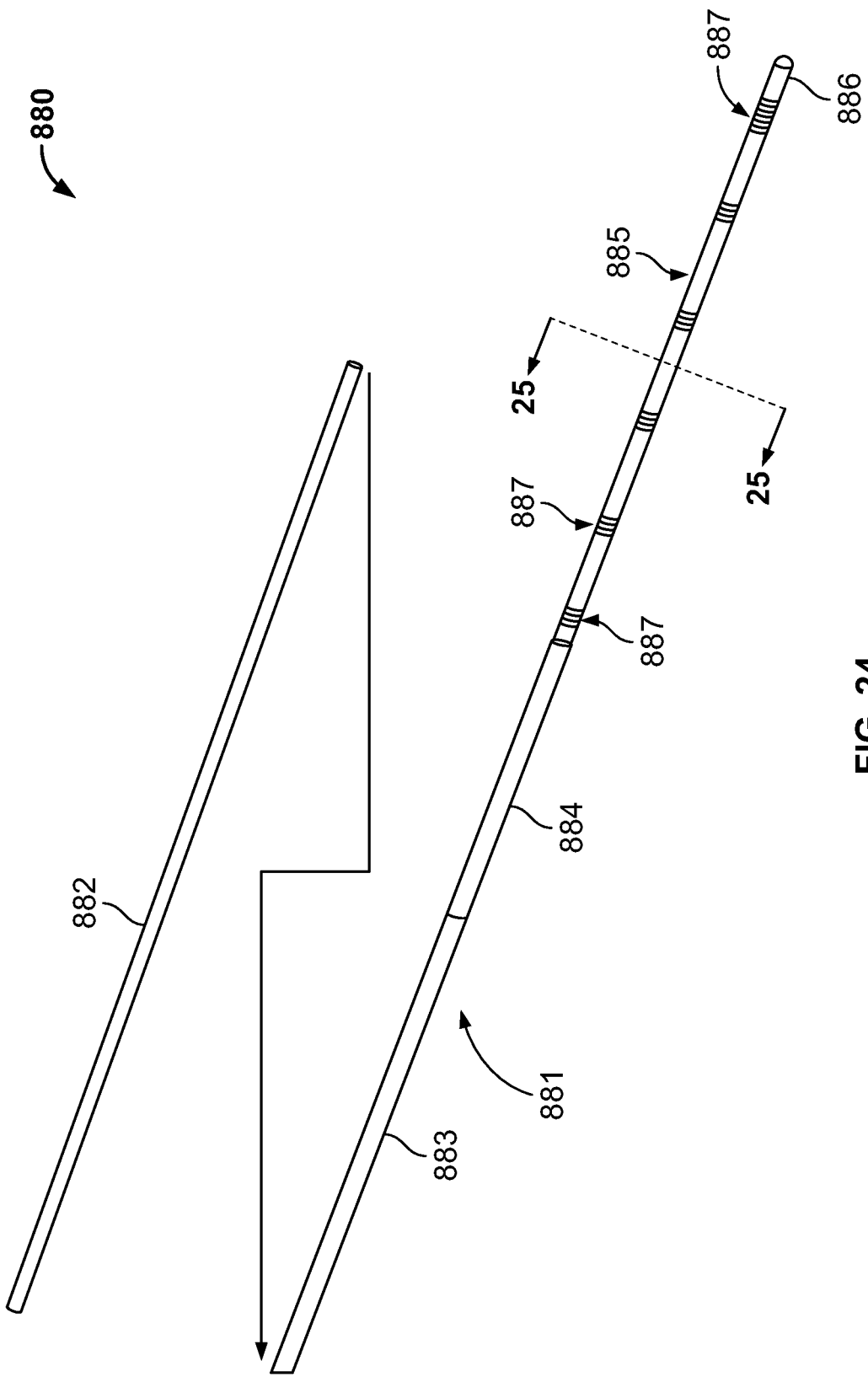
FIG. 24 is a perspective view of another embodiment of a cryoablation catheter having an internal stylet.

Depicted in FIG. 24 is an ablation catheter 880 according to another embodiment of the invention. In this embodiment, the ablation catheter 880 comprises two main components—(a) an ablation shaft/sleeve 881 for delivering ablation energy to a site of interest within the human body and (b) a stylet 882 that is capable of being inserted into an internal hollow cavity within the ablation shaft/sleeve 881. As will be discussed in more detail below, at least a portion of the ablation shaft/sleeve 881 is made of a flexible material such that this portion of the ablation shaft/sleeve 881 can assume a shape of the stylet 882 that is inserted therein and that is constructed from a shape memory alloy. While the ablation catheter 880 will be described herein for use as a cryoablation catheter that creates lesions by freezing tissue with any suitable cryogen (for example, and not limited to, nitrogen, argon, neon, helium, hydrogen, and oxygen), in other embodiments, the ablation catheter can be used with other ablation energies such as, for example, radiofrequency, microwave, laser, and high frequency ultrasound (HIFU).

As depicted in FIG. 24, the ablation shaft/sleeve 881 includes a handle portion (not shown and which may be constructed in accordance with any of the handle embodiments disclosed herein), a first shaft portion 883, a flexible shaft portion 884, a flexible distal ablation portion 885 and a distal ablation tip 886. In some embodiments, the ablation catheter 880 may also include a plurality of electrodes 887 on the flexible distal ablation portion 885 that may be used to detect electrical activity in the target tissue in order to evaluate or verify continuous contact of the flexible distal ablation portion 885 with the target tissue as described in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes. In some embodiments, electrodes 887 may be included on the distal ablation tip 886. In some embodiments, the first shaft portion 883 may be flexible, semi-flexible, semi-rigid or rigid. In some embodiments, the first shaft portion 883 is less flexible than the flexible shaft portion 884, however, the first shaft portion 883 will still be flexible such that it can be delivered through the venous system of the body to the target tissue.

Figure 25:
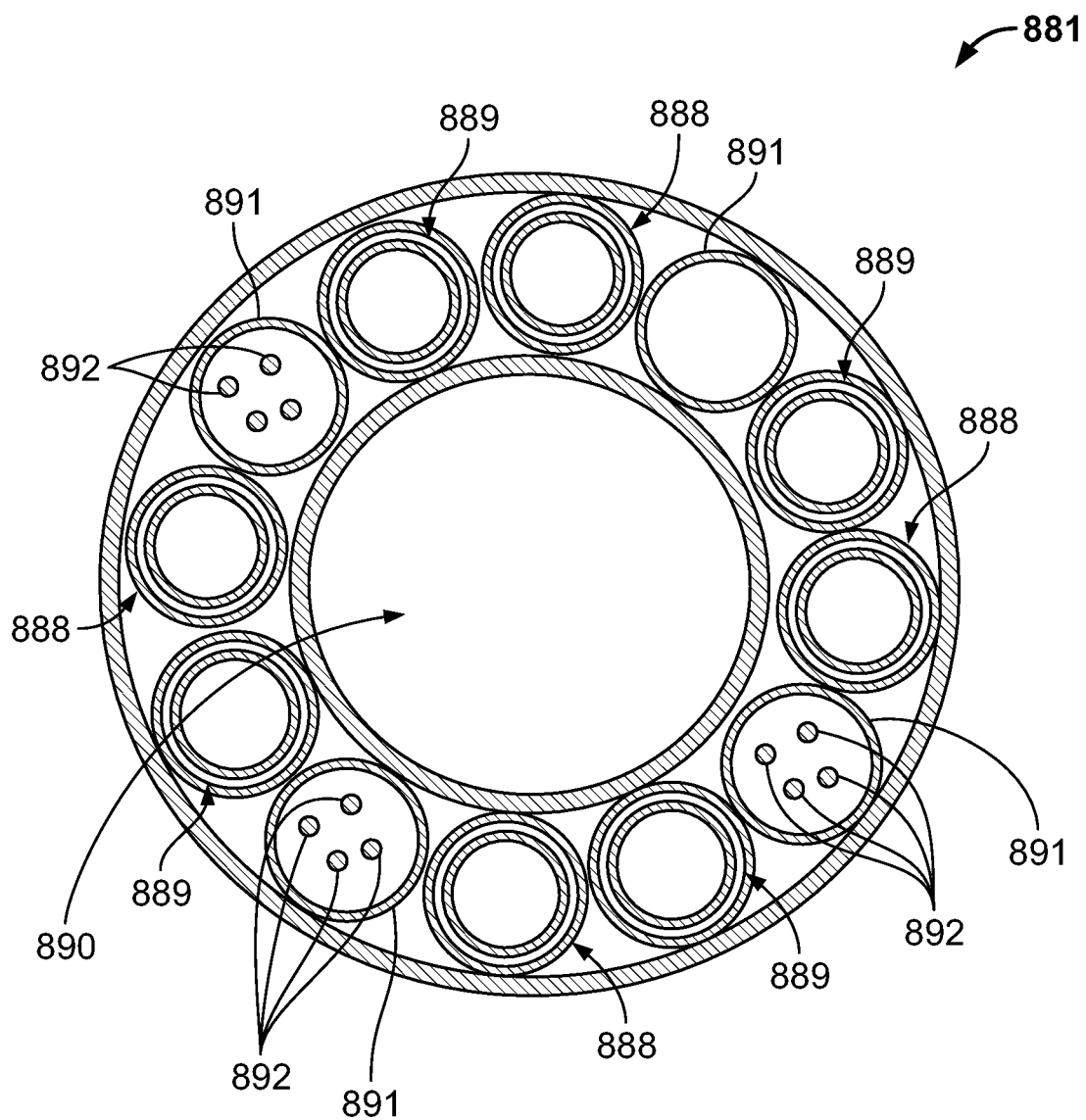
FIG. 25 is a cross sectional view of the catheter shown in FIG. 24 taken along line 25-25 in FIG. 24.

In some embodiments, the ablation shaft/sleeve 881 may comprise a handle portion, a flexible shaft portion 884, a flexible distal ablation portion 885 and a distal ablation tip 886. That is, the ablation shaft/sleeve 881 may be flexible along its entire length, FIG. 25 depicts a cross-sectional view of the ablation catheter 881 taken along line 25-25 in FIG. 24 with the stylet 882 not being inserted into the ablation shaft/sleeve 881. As can be seen in the cross-sectional view, the ablation shaft/sleeve 881 includes a plurality of multilayer cryogen delivery tubes/lumens 888 for transporting the cryogen to the flexible distal ablation portion 885 and a plurality of multilayer cryogen return tubes/lumens 889 for transporting the cryogen away from the flexible distal ablation portion 885. Also shown are a plurality of service tubes/lumens 885 that may include catheter control wires, electrode wires 892, or any other elements that may be desired. The plurality of multilayer cryogen delivery tubes/lumens 888, the plurality of multilayer cryogen return tubes/lumens 889 and the plurality of service tubes/lumens 885 are arranged in a circular array around a hollow tube/lumen 890 that is adapted to receive the stylet 882 therein. The hollow tube/lumen 890 extends along the length of the ablation shaft/sleeve 881 from the handle to at least the flexible distal ablation portion 885.

While FIG. 25 depicts four (4) multilayer cryogen delivery tubes 888, four (4) multilayer cryogen return tubes 889 and four (4) service tubes/lumens 891, the embodiments of the invention are not intended to be so limited and may include any number of multilayer cryogen delivery tubes 888, multilayer cryogen return tubes 889 and service tubes/lumens 891 depending on the desired ablating power of the catheter or the condition that the catheter will be used to treat. Additionally, while FIG. 25 depicts a certain configuration of the multilayer cryogen delivery tubes 888, the multilayer cryogen return tubes 889 and the service tubes/lumens 891, specifically that pairs of multilayer cryogen delivery tubes 888 and multilayer cryogen return tubes 889 are located adjacent to one another and separated with a service tubes/lumens 891, the embodiments of the invention are not intended to be so limited and may include any number of different configurations for the multilayer cryogen delivery tubes 888, the multilayer cryogen return tubes 889 and the service channels/tubes 891.

Figure 26:
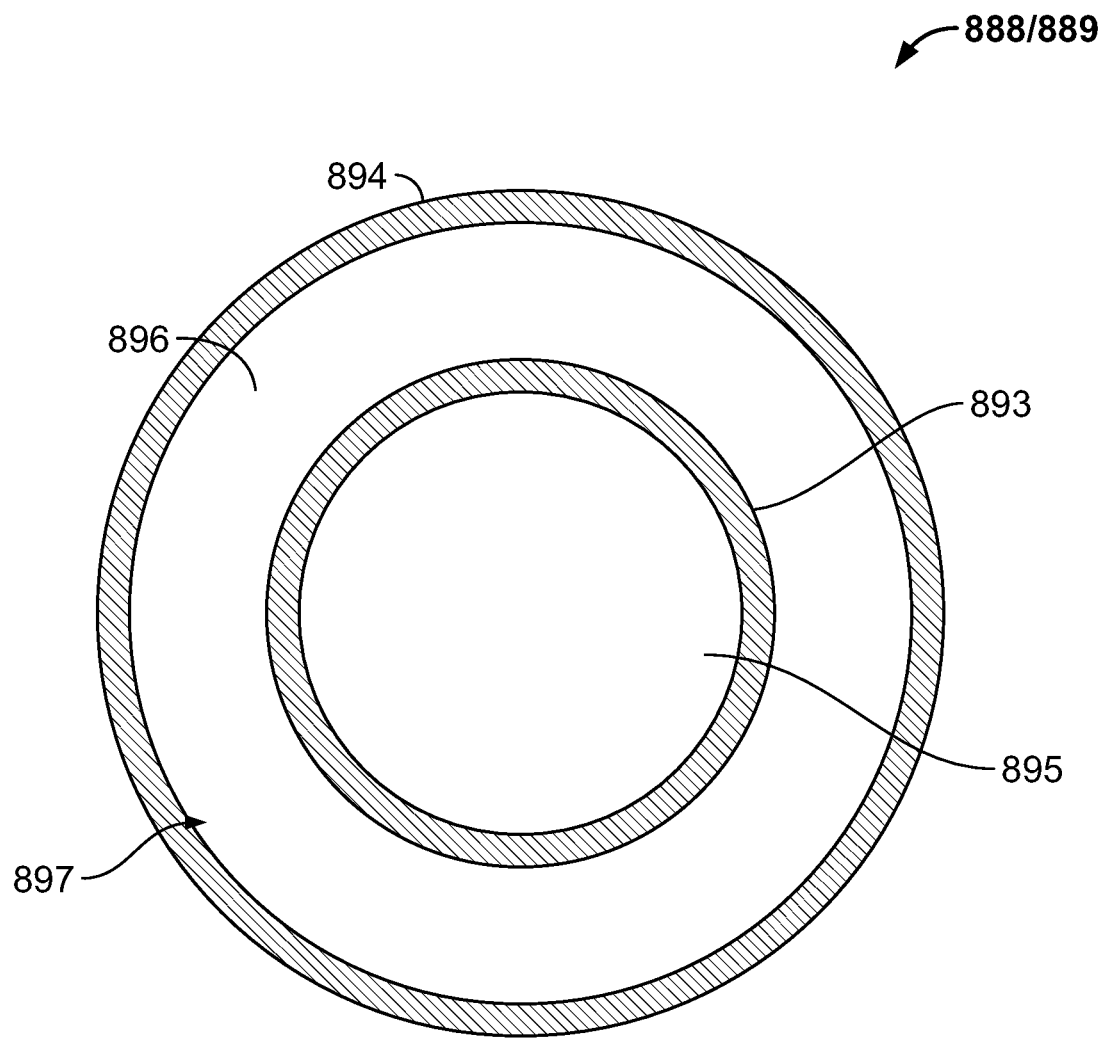
FIG. 26 is an enlarged view of the multi-layered cryogen delivery/return tubes shown in FIG. 25.

FIG. 26 shows an enlarged cross-sectional view of the multilayer cryogen delivery tubes 888 and multilayer cryogen return tubes 889 of FIG. 25. The first or inner tube 893 is shown coaxially surrounded by a second or outer tube 894. The lumen 895 of the inner tube 893 is designed to receive the flow of cryogen. The inner tube 893 and outer tube 894 are arranged such that a space or gap 896 is created between the exterior surface of the inner tube 893 and the interior surface of the outer tube 894. This gap 896 is capable of being filled with a thermally conductive media 897 as described herein. In some embodiments, the gap 896 has an annular shape. All of the multilayer cryogen delivery tubes 888 as well as the multilayer cryogen return tubes 889 can have a similar tube within a tube construction.

In the event of a leak of the cryogen flowing through lumen 895 or breach of the inner tube 893 during use, the leaking cryogen is contained within the gap 896 between the inner tube 893 and the outer tube 894. This tube within a tube construction adds an additional safety element to the device as any leaking fluid/cryogen is contained within the catheter and is prevented from entering the patient. In some embodiments, a pressure sensor/device or gauge may be incorporated to monitor the pressure of the thermally conductive media 897 in the gap 896. Therefore, if fluid/cryogen breaches the inner tube 893 and leaks into the gap 896, the pressure in the gap 896 and hence, the pressure of the conductive media 897 will increase. Should a change in pressure occur above a threshold limit, the system can be programmed to (a) halt ablation thereby preventing potential harm to a patient and/or (b) notify the surgeon of this change in pressure.

The inner tubes 893 may be fabricated and made from materials as described herein in connection with other flexible tubes for transporting the cryogen/cooling fluid. The outer tubes 895 may also be manufactured from a flexible material to enable elastic deflection of the flexible shaft portion 884 and the flexible distal ablation portion 885 of the ablation shaft/sleeve 881 to allow these portions to transform their shapes to assume the shape of the stylet 882 as disclosed herein. In some embodiments, the outer tube 895 is not inflatable, distensible nor expandable such that its size and shape remains substantially unaffected by the presence of the thermally conductive media 897 contained therein. Non-limiting exemplary materials for the outer tube 895 include polymers and metals or alloys. An example of an outer tube 894 material is polyimide.

The diameter of the flexible distal ablation portion 885 may vary. In some embodiments, the diameter of the flexible distal ablation portion 885 ranges from about 1-3 mm, and is preferably about 2 mm.

Figure 27A:
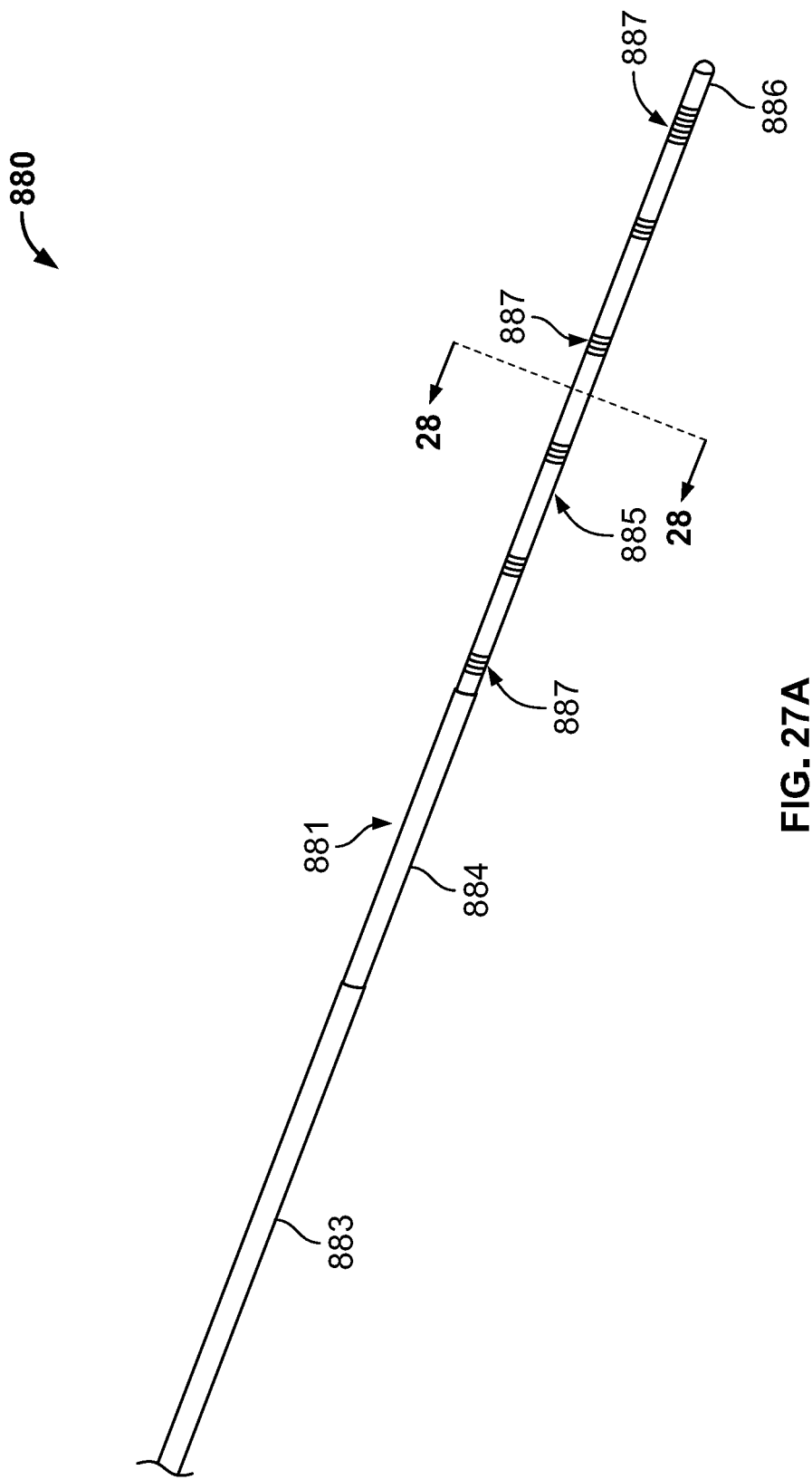
FIG. 27A is a perspective view of the cryoablation catheter depicted in FIG. 24 with the internal stylet inserted.
Figure 27B:
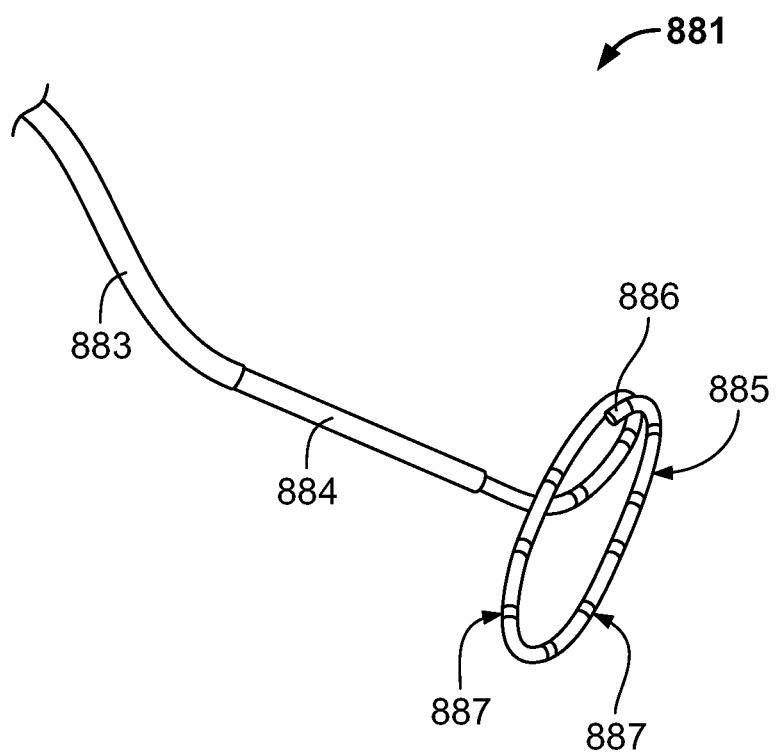
FIG. 27B is a perspective view of the cryoablation catheter depicted in FIG. 24 with the internal stylet inserted with the flexible distal ablation portion of the ablation shaft/sleeve transformed into the curved configuration of the stylet.

FIG. 27A and FIG. 27B depict an embodiment of the ablation catheter 880 with the stylet 882 fully inserted into the ablation shaft/sleeve 881 where FIG. 27A depicts the ablation catheter 880 with the stylet 882 inserted therein prior to the distal portion 898 of the stylet 882 transforming into its pre-set shape and FIG. 27B shows the ablation catheter 880 transformed into a pre-set shape of the distal portion 898 of the inserted stylet 882. FIG. 28 shows a cross-sectional view of the ablation catheter 880 of FIG. 27 taken along line 28-28 in FIG. 27A. As can be seen in FIG. 28, the stylet 882 is inserted into the hollow tube/lumen 890 of the ablation shaft/sleeve 881.

In some embodiments, in order to improve insertability/sliding of the stylet 882 within the hollow tube/lumen 890 of the ablation shaft/sleeve 881, the distal tip of the stylet 882 can be designed to have tip geometries that are tapered, that have a smaller diameter than the distal portion 898 of the stylet 882, are rounded, etc.

Figure 29:
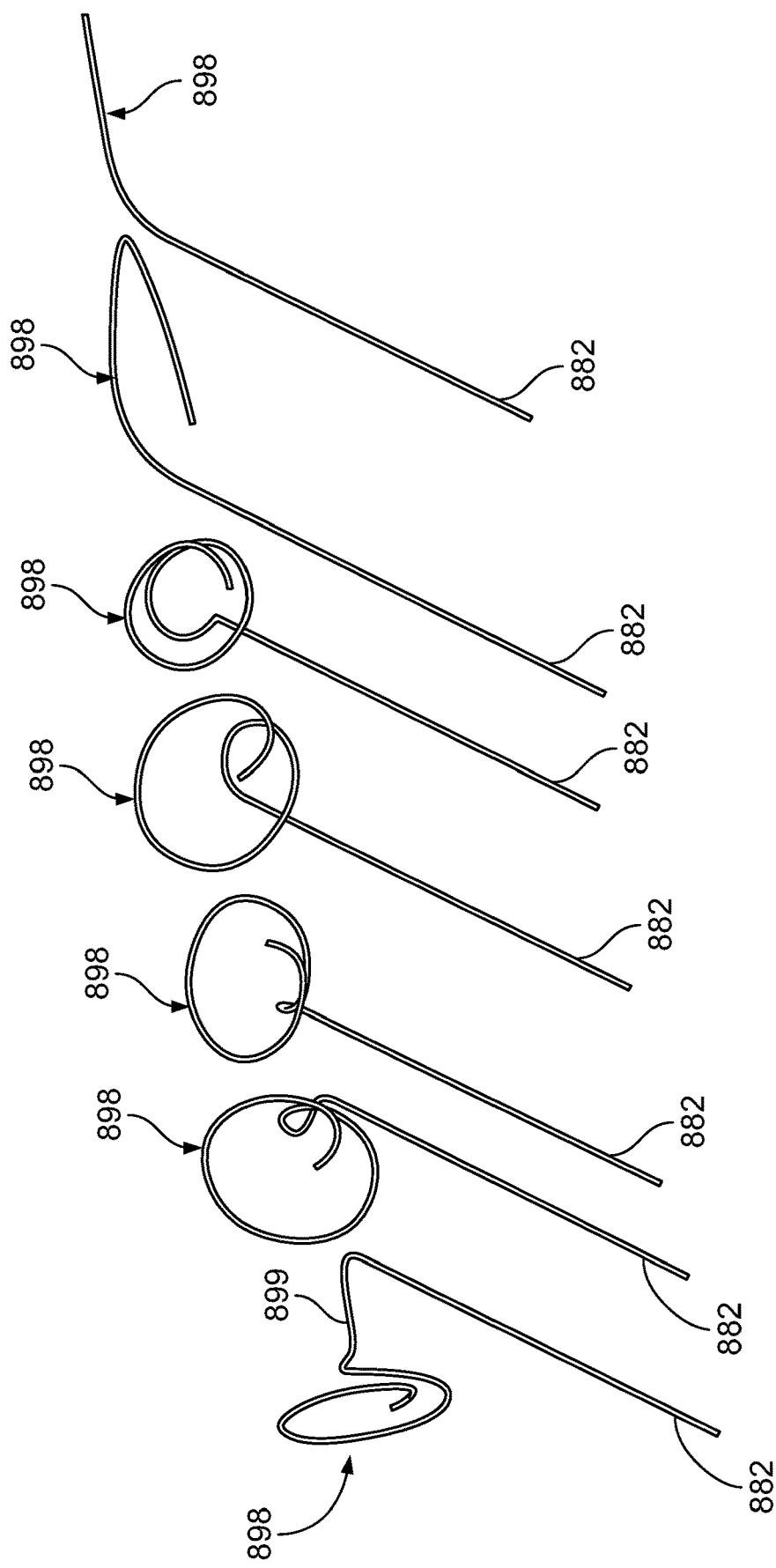
FIG. 29 depicts sample shapes for the stylet.

Depicted in FIG. 29 are sample shapes that can be pre-set into the distal portion 898 of the stylet 882. In some embodiments, the length of the distal portion 898 corresponds to at least a portion of the length of the flexible distal ablation portion 885 of the ablation shaft/sleeve 881. Thus, when the stylet 882 is in place in the hollow tube/lumen 890 of the ablation shaft/sleeve 881 and the flexible distal ablation portion 885 is positioned at the ablation site within the patient, the distal portion 898 of the stylet 882 transforms into its pre-set shape causing the flexible distal ablation portion 885 to transform to a corresponding shape as depicted in FIG. 27B.

Figure 27C:
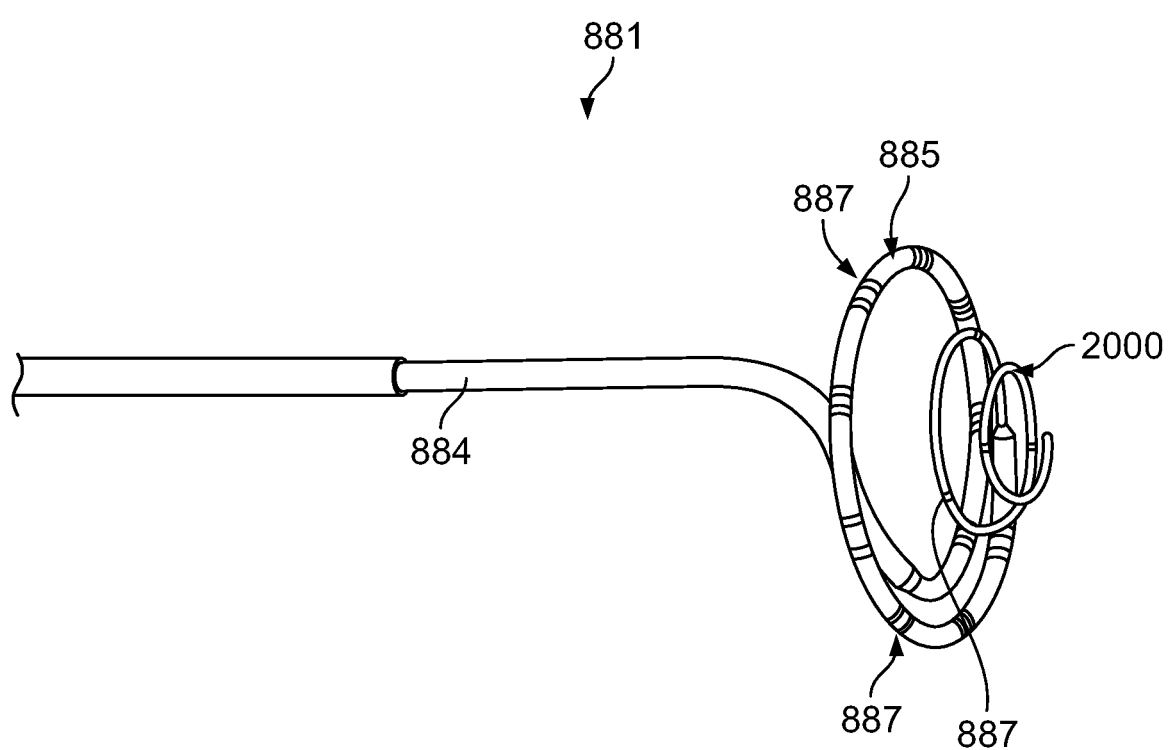
FIG. 27C is a perspective view of another embodiment of a cryoablation catheter having an internal stylet.
Figure 28:
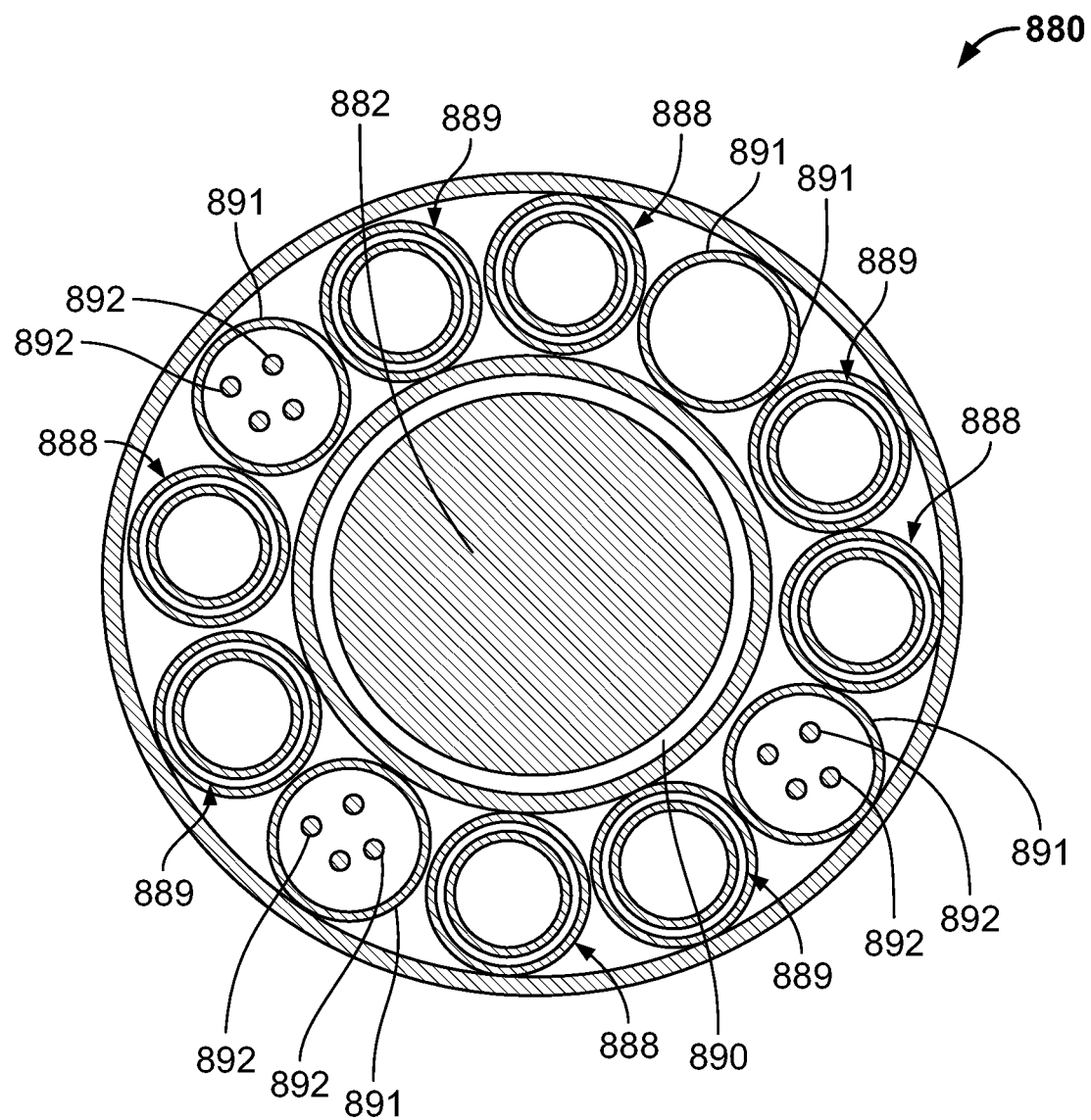
FIG. 28 is a cross sectional view of the catheter shown in FIG. 27A taken along line 28-28 in FIG. 27A.

FIG. 27C depicts another embodiment of the ablation catheter 880 with the stylet 882 fully inserted into the ablation shaft/sleeve 881. In this embodiment, instead of the flexible distal ablation portion 885 including a distal ablation tip, the flexible distal ablation portion 885 includes a non-ablating/non-freezing diagnostic portion 2000 that is used to position and/or hold the flexible distal ablation portion 885 in place against the target tissue to be ablated. Because the diagnostic portion 2000 is designed to be non-ablative, the ablation shaft/sleeve 881 portion that corresponds to the diagnostic portion 2000 does not include multilayer cryogen delivery tubes/lumens 888 and multilayer cryogen return tubes/lumens 889. In some embodiments, the diagnostic portion 2000 includes a plurality of electrodes 887.

The shape of the non-ablating diagnostic portion 2000 is pre-set in the shape memory alloy of the stylet 882. In the embodiment depicted in FIG. 27C, the diagnostic portion 2000 has a coiled spiral shape that is designed to be received within the pulmonary vein entries in the heart. Thus, when used to treat atrial fibrillation, the flexible distal ablation portion 885 is inserted into the left atrium. After the shape transforms into the shape depicted in FIG. 27C, the flexible distal ablation portion 885 is maneuvered adjacent to one of the pulmonary vein entries and the diagnostic portion 2000 is inserted into the pulmonary vein entry until the flexible distal ablation portion 885 contacts the tissue surrounding the pulmonary vein entry thereby encircling the pulmonary vein entry. Thus, the diagnostic portion 2000 ensures that the flexible distal ablation portion 885 is properly positioned around the pulmonary vein entry, that it will be held in place around the pulmonary vein entry and that a lesion will be formed completely around the pulmonary vein entry. As will be readily understood by those of skill in the art, the diagnostic portion 2000 can be designed to have any shape based on the area/tissue within the body to be ablated by the flexible distal ablation portion 885. That is, the diagnostic portion 2000 can be designed to have any shape that aids in properly and accurately positioning and/or holding the flexible distal ablation portion 885 in place in contact with the target tissue to be ablated.

The shape of the distal portion 898 of the stylet 882 can be based on the type of procedure/treatment that the ablation catheter 880 will be used to perform as well as the patient's anatomy where the treatment is being performed. Thus, if a procedure is performed with one stylet 882 having a specific shape/orientation and the ablation was not successful because of incomplete lesion formation, for example, the surgeon can simply remove the stylet 882 from the ablation shaft/sleeve 881 while leaving the ablation shaft/sleeve 881 in place in the patient. The surgeon can then (a) choose a different stylet 882 having a distal portion 898 with a different size and/or shape than that of the previously-used stylet 898, (b) insert this new stylet 882 into the hollow tube/lumen 890 of the ablation shaft/sleeve 881 and (c) continue with the ablation procedure. The surgeon can do this as many times as is necessary to achieve a successful ablation, e.g., complete lesion formation.

In some embodiments, a portion 899 of the stylet 882 can be set with a pre-determined articulation angle, which can be helpful in directing the flexible distal ablation portion 885 into contact with the target tissue for the ablation. In some embodiments, the articulation portion 899 of the stylet 882 corresponds to the flexible shaft portion 884 of the ablation shaft/sleeve 881.

Figure 30:
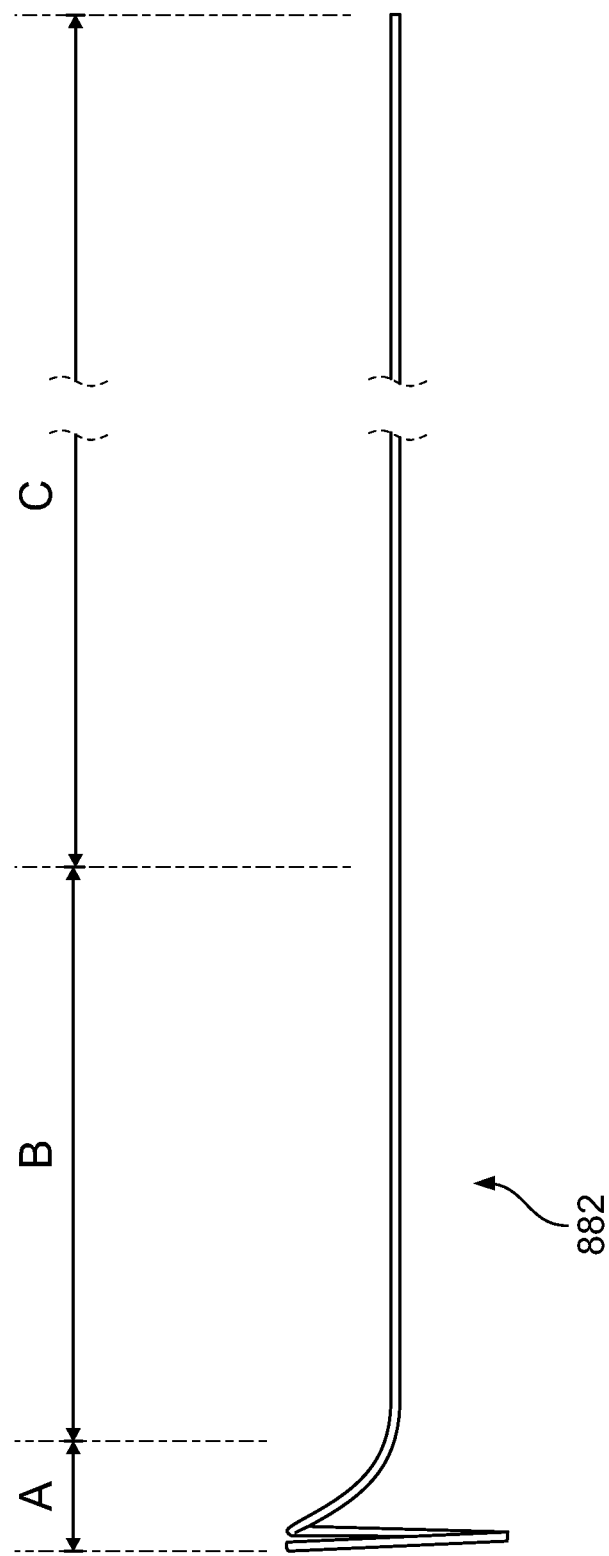
FIG. 30 depicts a stylet having multiple flexibilities long its length, according to an embodiment of the invention.

In some embodiments, the stylet 882 can be designed to have different flexibilities along its length. As depicted in FIG. 30, in one embodiment, the stylet 882 can be designed to have three (3) portions identified as portions "A," "B" and "C" with different flexibilities. For example, portion "A" can have a first flexibility, portion "B" can have a second flexibility and portion "C" can have a third flexibility. In some embodiments, portion "B" is more flexible that portions "A" and "C" as it may be necessary for portion "B" and its associated portion of the ablation shaft/sleeve 881 to articulate such that portion "A" and its associated portion of the ablation shaft/sleeve 881 can be manipulated into contact with the target tissue within the heart to be ablated. It may be necessary for portions "A" and "C" and their associated portions of the ablation shaft/sleeve 881 to be less flexible/more rigid or stiffer than portion "B" such that pressure/force can be applied during delivery of the ablation shaft/sleeve 881 and transferred to the flexible distal ablation portion 885 of the ablation shaft/sleeve 881 such that the flexible distal ablation portion 885 can be manipulated into the proper position against the target tissue and held in place.

In some embodiments, portions of the stylet 882 can be designed to have a flexibility similar to the flexibility of corresponding portions of the of the ablation shaft/sleeve 881. In some embodiments, the ablation shaft/sleeve 881 can be designed to have a uniform flexibility, however, the flexibility of specific portions the ablation shaft/sleeve 881 can be adjusted or controlled based on the flexibility of corresponding portions of the stylet 882. Thus, the stylet 882 may be responsible for controlling the flexibility of the catheter 880.

The flexibility along the length of the stylet 882 can be changed or altered in various ways. For example, in some embodiments, the properties of the shape memory material from which the stylet 882 is constructed, can be altered. One property that can be altered is the transition temperature of the shape memory alloy. Thus, a shape memory alloy that may have a certain flexibility at one temperature can have a different flexibility at the same temperature due to an altered transition temperature.

As depicted in FIG. 31A and FIG. 31B, in one embodiment, the flexibility along the length of the stylet 882 can be altered by changing the diameter of the stylet 882. FIG. 31B, which is a detail of View A in FIG. 31A, shows that material can be removed from stylet 882 such that portions of the stylet 882 have a diameter "d1" while other portions of the stylet 882 have a diameter "d2," which is less than diameter "d1." Thus, portions of the stylet 882 that have either diameters that alternate between "d1" and "d2" or that have extended lengths "L2" with a diameter "d2," are more flexible than portions of the stylet 882 that have a consistent diameter "d1." In some embodiments, the flexibility can be altered based on lengths "L1" and "L2" of the larger diameter portions "d1" and smaller diameter portions "d2," respectively. Thus, portions of the stylet 882 having lengths "L2" of smaller diameter portions "d2" that are greater in length than the length "L1" of larger diameter portions "d1" will be more flexible than portions of the stylet 882 having lengths "L2" of smaller diameter portions "d2" that are shorter in length than the length "L1" of larger diameter portions "d1." In other embodiments, any number of different diameter stylet portions, i.e., "d1," "d2," "d3," "d4," etc., of any lengths may be designed to impart the desired flexibility on the stylet 882 and these different diameter stylet portions may be arranged in any order and/or configuration to impart the desired flexibility on the stylet 882.

Figures 32A, 32B, 32C:
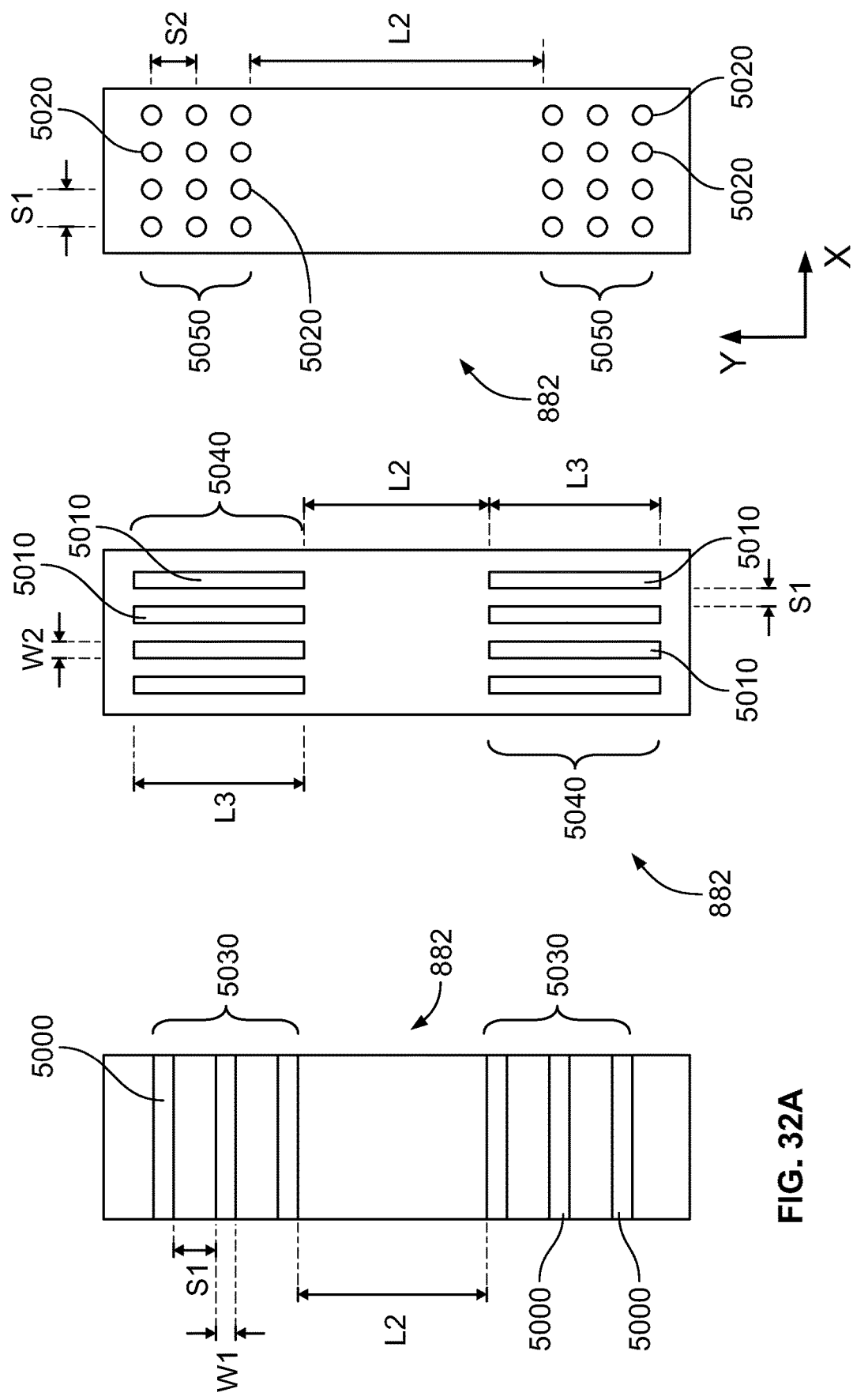
FIG. 32A depicts a method of altering the flexibility of a portion of a stylet, according to an embodiment of the invention.
FIG. 32B depicts a method of altering the flexibility of a portion of a stylet, according to an embodiment of the invention.
FIG. 32C depicts a method of altering the flexibility of a portion of a stylet, according to an embodiment of the invention.

In some embodiments, as depicted in FIGS. 32A-32C, the flexibility of portions of the stylet 882 can be altered with the inclusion of a plurality of circumferential grooves 5000, a plurality of longitudinal grooves 5010, or a plurality of holes 5020. In the embodiment depicted in FIG. 32A, the flexibility of the stylet 882 can be altered based on the width "W1" of the circumferential grooves 5000, the spacing "S1" between adjacent groves 5000 and the spacing "L2" between adjacent sets 5030 of circumferential grooves 5000. Thus, (a) embodiments having circumferential grooves 5000 that have a width "W1" that is greater than a width "W1" of circumferential grooves 5000 in other embodiments, (b) embodiments having circumferential grooves 5000 that have a closer spacing "S1" between adjacent grooves 5000 than spacing "S1" between circumferential grooves 5000 in other embodiments and (c) embodiments having sets 5030 of circumferential grooves 5000 that have a shorter distance "L2" between adjacent sets 5030 of circumferential grooves 5000 than in other embodiments, will be more flexible than in the other embodiments. Various combinations of widths "W1", spacings "S1" and distances "L2" can be designed to achieve the desired flexibilities of different portions of the stylet 882.

In the embodiment depicted in FIG. 32B, the flexibility of the stylet 882 can be altered based on the width "W2" of the longitudinal grooves 5010, the spacing "S1" between adjacent grooves 5010, the spacing "L2" between adjacent sets 5040 of longitudinal grooves 5010 and the length "L3" of the longitudinal grooves 5010. Thus, (a) embodiments having longitudinal grooves 5010 that have a width "W2" that is greater than a width "W2" of longitudinal grooves 5010 in other embodiments (b) embodiments having longitudinal grooves 5010 that have a length "L3" that is greater than a length "L3" of longitudinal grooves 5010 in other embodiments, (c) embodiments having longitudinal grooves 5010 that have a closer spacing "S1" between adjacent longitudinal grooves 5010 than spacing "S1" between adjacent longitudinal grooves 5010 in other embodiments and (d) embodiments having sets 5040 of longitudinal grooves 5010 that have a shorter distance "L2" between adjacent sets 5040 of longitudinal grooves 5010 than in other embodiments, will be more flexible than in the other embodiments. Various combinations of widths "W2", lengths "L3," spacings "S1" and distances "L2" can be designed to achieve the desired flexibilities of different portions of the stylet 882.

In the embodiment depicted in FIG. 32C, the flexibility of the stylet 882 can be altered based on the diameter "D3" of the holes 5020, the spacing "S1" between adjacent holes 5020 in the X-direction, the spacing "S2" between adjacent holes 5020 in the Y-direction and the spacing "L2" between adjacent sets 5050 of holes 5020. Thus, (a) embodiments having holes 5020 that have a diameter "D3" that is greater than a diameter "D3" of holes 5020 in other embodiments, (b) embodiments having holes 5020 that have a closer spacing "S1" between adjacent holes 5020 in the X-direction than spacing "S1" between adjacent holes 5020 in the X-direction in other embodiments, (c) embodiments having holes 5020 that have a closer spacing "S2" between adjacent holes 5020 in the Y-direction than spacing "S2" between adjacent holes 5020 in the Y-direction in other embodiments and (d) embodiments having sets 5050 of holes 5020 that have a shorter distance "L2" between adjacent sets 5050 of holes 5020 than in other embodiments, will be more flexible than in the other embodiments. Various combinations of diameters "D3", spacings "S1," spacings "S2" and distances "L2" can be designed to achieve the desired flexibilities of different portions of the stylet 882.

In most embodiments, the degree of flexibility correlates to the amount of stylet material that is removed or that remains in the portions of the stylet 882 where altered flexibilities are desired. Portions of the stylet 882 having more material removed will be more flexible than portions of the stylet 882 having less material removed.

In the stylet embodiments disclosed herein, combinations of alterations may be used. For example, desired flexibilities can be achieved by combining smaller diameter portions with circumferential grooves 5000 and/or longitudinal grooves 5010 and/or holes 5020.

The multiple flexibilities in the embodiments disclosed herein are due to a removal of material in portions of the stylet along its length. The removed material can be in the form of smaller diameter portions, circumferential grooves, longitudinal grooves and/or holes and any other shapes as will be readily apparent to those skilled in the art.

In some embodiments, multiple flexibilities along the length of the stylet 882 can be achieved by altering/changing the alloy composition of the shape memory alloy material used to construct certain portions of the stylet 882. In some embodiments, the multiple flexibilities of the stylet 882 can be achieved based on different shape setting heat treatments at different locations along the length of the stylet 882.

In some embodiments, the ablation catheter 880 may be packaged as a kit with multiple stylets 882 having various shapes and sizes thereby giving the physician different options regarding the size and shape of the lesions to be created during the ablation procedure. These kits can be treatment specific. Therefore, only stylets having shapes and sizes for the specific procedure can be included in the kits. Thus, the ablation catheter 880 of this embodiment allows a single, universal ablation shaft/sleeve 881 to be designed and constructed that can be used for a multitude of various ablation procedures based only on providing stylets 882 specific for the procedure being performed. Constructing a single, universal ablation shaft/sleeve 881 is more cost efficient and provides for higher production rates than having to construct multiple ablation catheters that are designed to have different shapes and different handle functionality.

In some embodiments, the ablation shaft/sleeve 881 can be used to perform ablations without a stylet 882 inserted therein.

As previously disclosed, in some embodiments, the stylet 882 can made from a shape memory alloy such as, for example, nickel titanium (Nitinol). The shape of the stylet can be set with varying degrees of shape setting/training heat treatments (temperature, time, the amount of prior cold work, Bend and Free Recovery ("BFR") testing, which determine the shape memory alloy's final mechanical properties, austenite finish ("Af") transformation temperature, and alloy composition.

In some experiments with embodiments of a cryoablation catheter, as freezing of the ablation catheter 880 begins, expansion of the stylet 882 distal portion 898 and hence, expansion of the distal ablation portion 885 was noticed. This expansion prevented the loop of the distal ablation portion 885 from completely encircling/enclosing causing non-continuous lesions to form around the respective anatomical features. Through experimentation and characterization of several temperatures, times, quench settings, and BFR testing, it was determined that the Af temperatures of the nitinol stylet 882 needed to be set to below freezing temperatures (0° C.) in order for ice to form around the catheter distal portion thereby locking the shape of the distal ablation portion 885 before the distal ablation portion 885 had an opportunity to expand. It was also determined that expansion of the distal ablation portion 885 could be controlled by setting the Af temperature as expansion increases with Af temperature. Although this expansion was originally viewed as a disadvantage, it was determined that a cryoablation catheter with both expanding and non-expanding capabilities could be advantageous when ablating various parts of the anatomy.

In some embodiments, a stylet 882 is formed using Nitinol wire for its unique properties of shape memory and superelasticity. The successful joining of the stylet 882 in combination with the flexible properties of the ablation shaft/sleeve 881 requires precise control of the stylet's 882 transformational and mechanical properties. Transformational and mechanical properties of the stylet 882 are imparted through heat treatment settings and BFR testing. During the shaping process, active Af temperature specifications are locked into the material by process temperature, time, and quench settings. Temperatures above the active Af temperatures such as ambient and body temperatures, keep the nitinol wire of the stylet 882 in a super elastic and austenitic state, while the material is in the twinned martensitic phase at temperatures below the active Af temperature and is therefore, easily deformed. This pre-programmed Af temperature controls the amount of movement or expansion of the shaped distal portion 898 of the stylet 882 as it undergoes phase transformation into the martensitic phase. Due to the flexibility of the ablation catheter distal ablation portion 885, a method was developed to "pre-program" in Af temperatures to control and manipulate expansion of the distal ablation portion's 885 shape for all anatomical structures resulting in improved efficacy.

As the stylet 882 is advanced into the ablation shaft/sleeve 881, it transforms the distal ablation portion 885 of the ablation shaft/sleeve 881 into the shape of the pre-set shape of the distal portion 898 of the stylet 882 as it is heated to body temperature (approximately 37° C.). As cryogen is delivered into the ablation shaft/sleeve 881, freezing begins in the distal section while temperatures drop from body temperature down to cryogenic temperatures, which in some embodiments, is approximately −196° C. Ice formation around the distal ablation portion 885 of the ablation shaft/sleeve 881 occurs near the freezing temperature of water (approximately 0° C.). The Af temperature of the distal portion 898 of the stylet 882 determines if either (i) movement or expansion will occur before ice formation on the distal ablation portion 885 of the ablation shaft/sleeve 881 because the Af temperatures are set above the freezing temperature or (ii) no movement or expansion will occur because the Af temperatures are set below the freezing temperature. Expansion/movement of the distal ablation portion 885 of the ablation shaft/sleeve 881 is increased as the Af temperature is increased in the distal portion 898 of the stylet 882. These pre-programmed Af temperatures can therefore either prevent the distal ablation portion 885 of the ablation shaft/sleeve 881 from expanding or cause the distal ablation portion 885 of the ablation shaft/sleeve 881 to expand incrementally, based on the Af temperature of the distal portion 898 of the stylet 882.

Furthermore, both expanding and non-expanding options for the distal ablation portion 885 of the ablation shaft/sleeve 881 are significant to the efficacy of the ablation as anatomical structures contain several mechanical properties including stiffness, elasticity, hardness, and lubricity while expanding/contracting with the vital functions of the body.

As will be discussed in more detail below, in use, the ablation shaft/sleeve 881 is delivered to an area of interest with the body, in some embodiments, for example, the left atrium of the heart to treat atrial fibrillation or the right atrium to treat atrial flutter or the right and left ventricles to treat ventricular tachycardia, through a delivery catheter. After the ablation shaft/sleeve 881 is in position and depending on the ablation treatment being performed and the patient's anatomy, the surgeon chooses a stylet 881 to use. The surgeon then inserts this stylet 881 through the catheter handle and into the hollow tube/lumen 890 of the ablation shaft/sleeve 881 until the distal portion 898 of the stylet 882 is in place within the flexible distal ablation portion 885. Once in place, the shape memory characteristics of the distal portion 898 of the stylet 882 cause the distal portion 898 to transform into its pre-set shape thereby causing the flexible distal ablation portion 885 to transform into a corresponding shape. The surgeon can then proceed with the ablation treatment.

Applications

Embodiments of the cryoablation apparatus (catheters, probes, etc.) described herein have a wide range of diagnostic and therapeutic applications including, for example, endovascular-based cardiac ablation and more particularly, the endovascular-based cardiac ablation treatment of atrial fibrillation.

Figure 33:
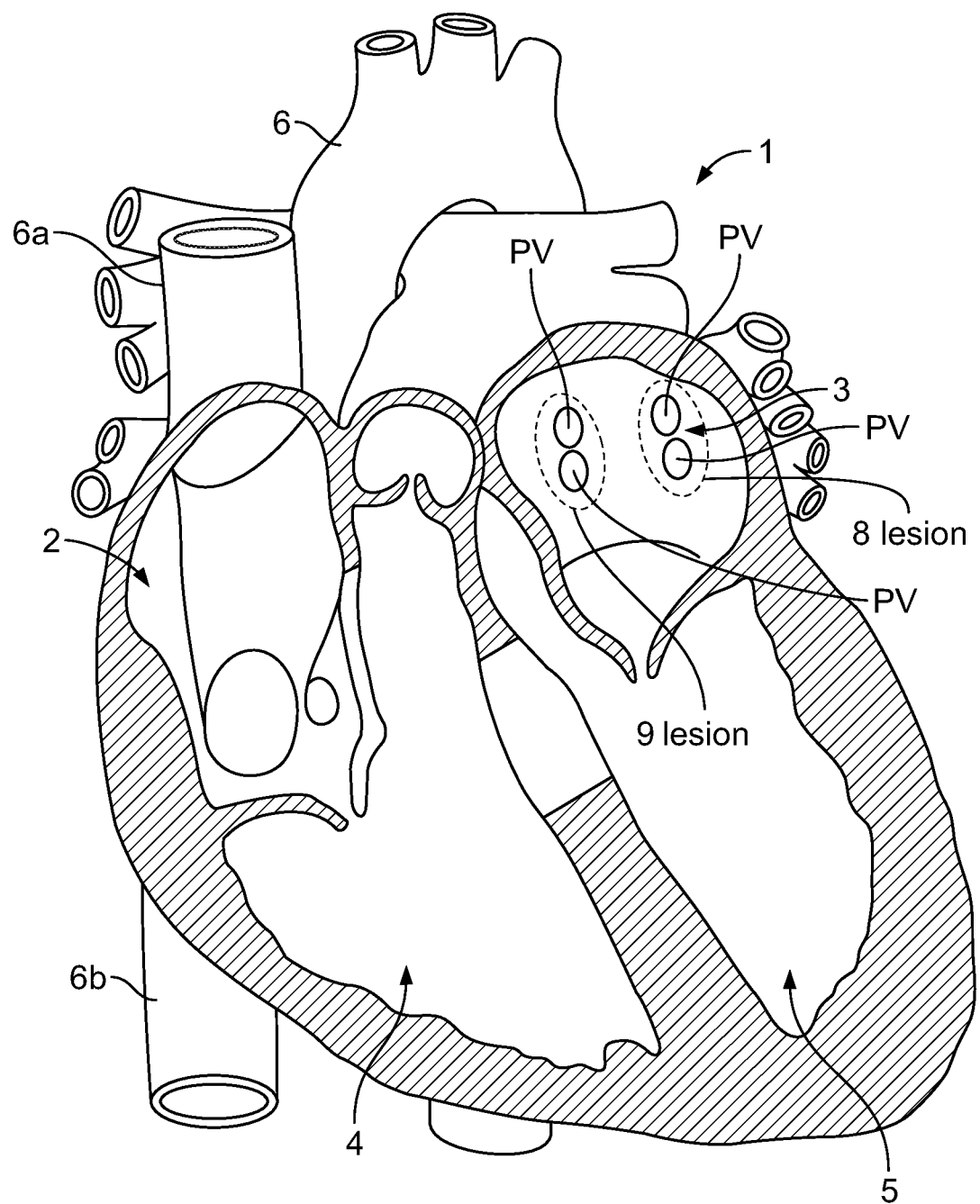
FIG. 33 is an illustration of a heart, and locations of various lesions according to an embodiment of the invention.

FIG. 33 shows examples of target ablation lesions in a pulmonary vein isolation (PVI) procedure for the treatment of atrial fibrillation.

The basic structures of the heart 1 are shown in FIG. 33 including the right atrium 2, the left atrium 3, the right ventricle 4 and the left ventricle 5. The vessels include the aorta 6 (accessed through the femoral artery), the superior vena cava 6a (accessed through the subclavian veins) and the inferior vena cava 6b (accessed through the femoral vein).

Exemplary target lesions for a PVI procedure include lesion 8 which surrounds and isolates all left pulmonary veins (PVs), and lesion 9 which surrounds and isolates all right pulmonary veins (PVs). As described further herein, the invention may include application or creation of additional lesions to increase the effectiveness of the treatment. Also, it is to be understood that although the following discussion primarily focuses on embodiments for performing PVI, the technology and procedure described herein for producing these lesions can be used to create other lesions in an around the heart and other organs such as that described in international patent application nos. PCT/US2012/047484 to Cox et al. and PCT/US2012/047487 to Cox et al. corresponding to International Publication Nos. WO 2013/013098 and WO 2013/013099 respectively, the contents of each of which is hereby incorporated by reference in their entirety.

Figure 34:
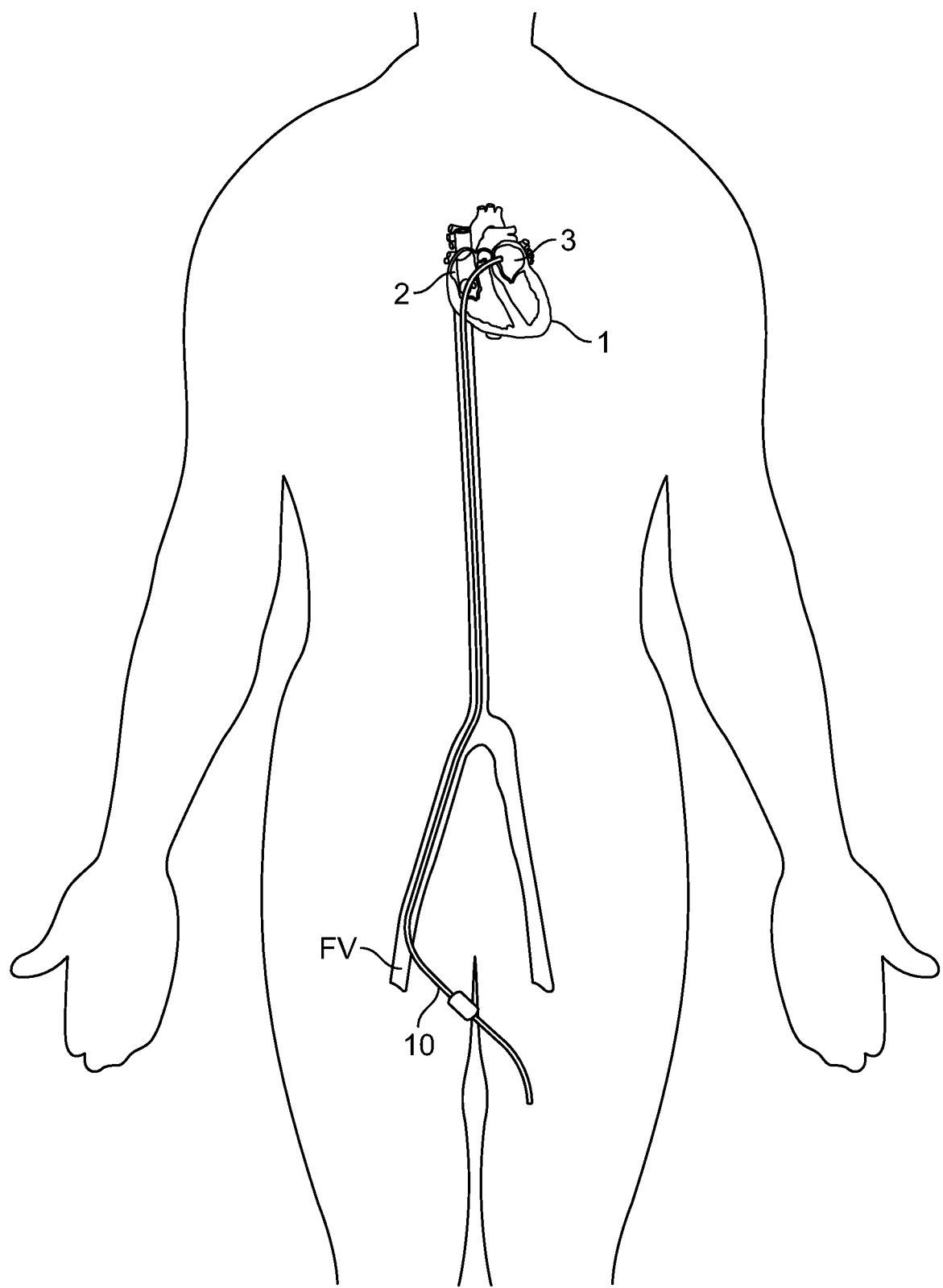
FIG. 34 is an illustration of an embodiment of endovascular catheterization to access the heart.

FIG. 34 illustrates one technique to reach the left atrium with the distal treatment section of a catheter. The procedure may be performed under conscious sedation, or general anesthetic if desired.

A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis.

With the introducer sheath in place, the guiding catheter 10 or sheath is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for devices through its own inner lumen and into the left atrium.

Placement of the above tools may be carried out with guidance from one or more of the following: fluoroscopy, intracardiac pressures, transesophageal echocardiography (TEE), and intracardiac echocardiography (ICE).

FIGS. 35-38 illustrate a method for deploying a ring-shaped catheter in the left atrium and around pulmonary vein entries for treating various heart conditions such as atrial fibrillation.

Figure 35:
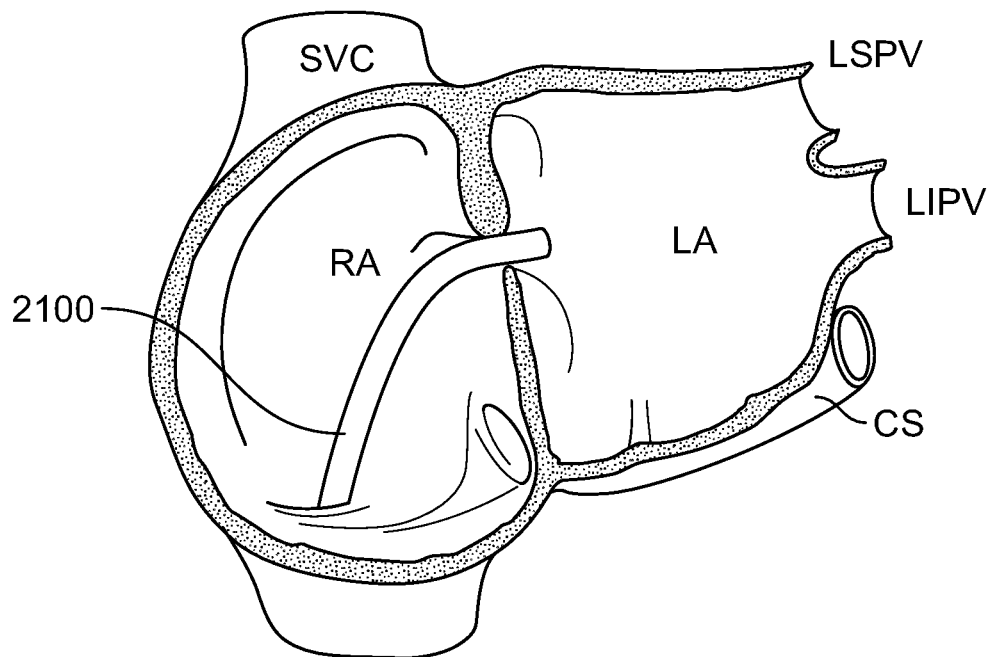
FIGS. 35-36 are illustrations of a procedure to place a distal section of a cryoablation catheter against the endocardial wall in the left atrium, circumscribing the left superior and inferior pulmonary vein entries, according to an embodiment of the invention.

With reference first to FIG. 35, a cross sectional view of the heart includes the right atrium RA 2, left atrium LA 3, left superior pulmonary vein LSPV entry, and left inferior pulmonary vein LIPV entry. Guide catheter 2100 is shown extending through the septum and into the left atrium.

Though not shown, mapping catheters may be positioned in the entry to the LSPV of the left atrium for monitoring electrical signals of the heart. The mapping catheters may be placed in other locations, such as, for example the coronary sinus (CS). Examples of mapping catheters include the WEBSTER® CS Bi-Directional Catheter and the LASSO® Catheter, both of which are manufactured by Biosense Webster Inc. (Diamond Bar, Calif. 91765, USA). Another example of mapping and cryo-treatment system is described in US Patent Publication No. 2015/0018809 to Mihalik.

Optionally, an esophageal warming balloon may be placed in the esophagus to mitigate collateral damage arising from creating the lesions. An esophageal warming balloon prevents the cold temperatures from reaching the inner layer of cells of the esophagus, and can prevent formation of, e.g., an atrio-esophageal fistula. An example of a suitable esophageal warming balloon apparatus that may be used is described in commonly assigned U.S. patent application Ser. No. 15/028,927, entitled "ENDOESOPHAGEAL BALLOON CATHETER, SYSTEM, AND RELATED METHOD," filed Oct. 12, 2014 by Alexei Babkin, et al., the contents of which is incorporated herein by reference in its entirety for all purposes.

Figure 36:
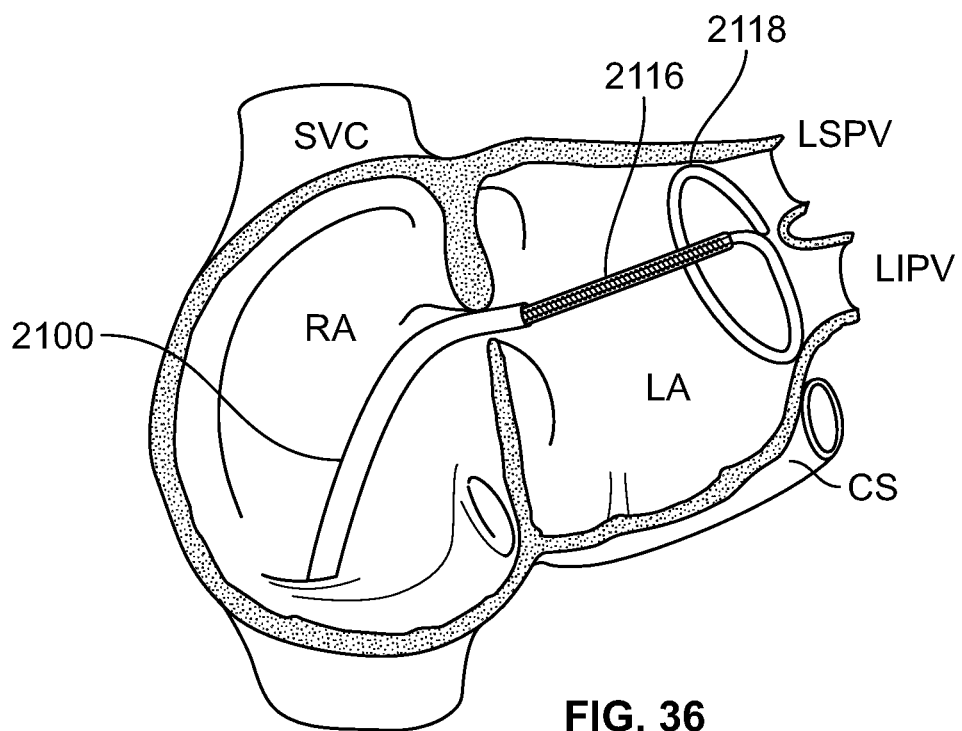

FIG. 36 illustrates a distal section of the cryoablation catheter 2116 advanced through the guide sheath 2100. The energy element 2118 is shown having a circular shape formed as disclosed and described herein and urged against the endocardium. As described herein the shape may be adjusted to make continuous contact with the tissue, and to form an elliptical or circular-shaped continuous lesion (such as lesion 8 shown in FIG. 33) which encloses all the left PV entries.

In embodiments the shape is modified by reducing the diameter of loop, articulating the intermediate section of the shaft, and rotating or steering the catheter distal section. Collectively, the steps of deployment, diameter control, steering and articulation can place the entire circumference of the loop in continuous contact with the endocardium tissue. When energy is applied to the distal treatment section such as, for example, by flowing a cryogen through the distal treatment section, a continuous elongate ring-shaped lesion (frozen tissue) is formed such as the lesion 8 shown in FIG. 33, enclosing all left pulmonary vein entries.

Figure 37:
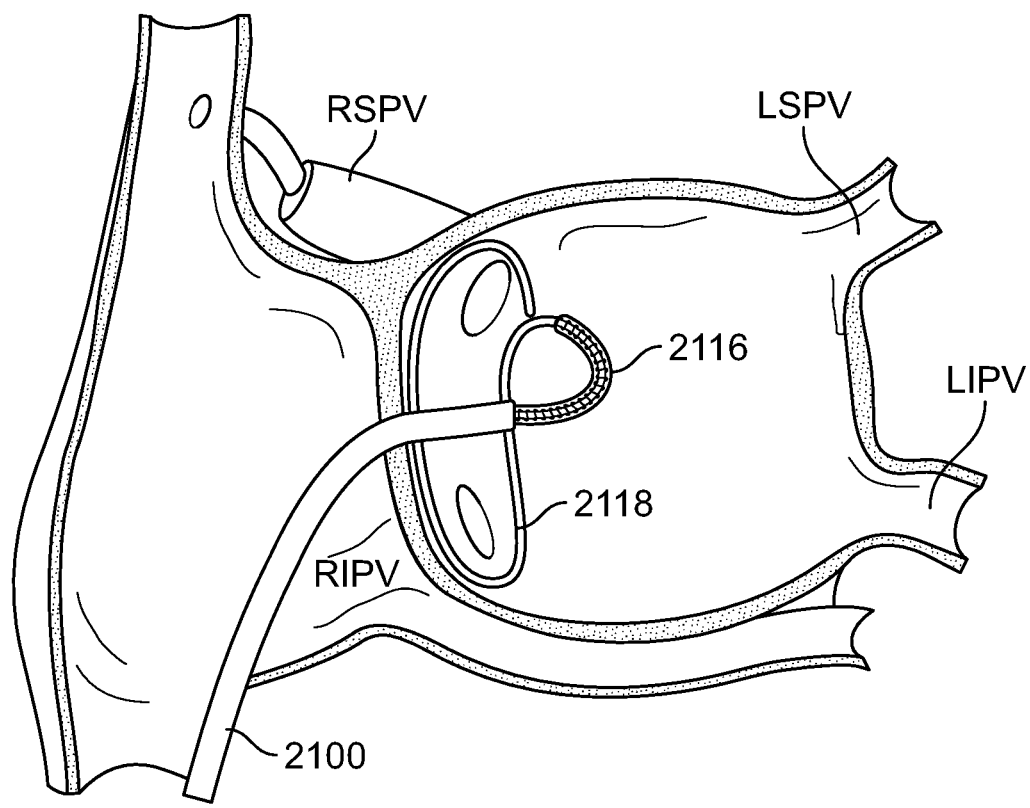
FIGS. 37-38 are illustrations of a procedure to place a distal section of a cryoablation catheter against the endocardial wall in the left atrium, circumscribing the right superior and inferior pulmonary vein entries, according to an embodiment of the invention.

FIG. 37 illustrates formation of a ring-shaped lesion around the right superior pulmonary vein (RSPV) entries and the right inferior pulmonary vein (RIPV) entries such as, for example, lesion 9 shown in FIG. 33. In contrast to the somewhat linear (straight shot) positioning shown in FIGS. 35-36, the catheter neck region 2116 shown in FIG. 37 is deflected nearly 180 degrees to aim towards the right pulmonary veins. Energy element portion 2118 is positioned around the RSPV and RIPV entries.

FIG. 37 shows the energy element 2118 deployed in a circular shape and contacting the endocardium. As described herein the shape may be adjusted to make better contact with the tissue in order to form an elongate ring-shaped, continuous lesion that engulfs or surrounds the RSPV and RIPV entries.

A similar elongate ring-shaped, continuous lesion can be formed to surround the left superior pulmonary vein (LSPV) entries and the left inferior pulmonary vein (LIPV) entries.

Figure 38:
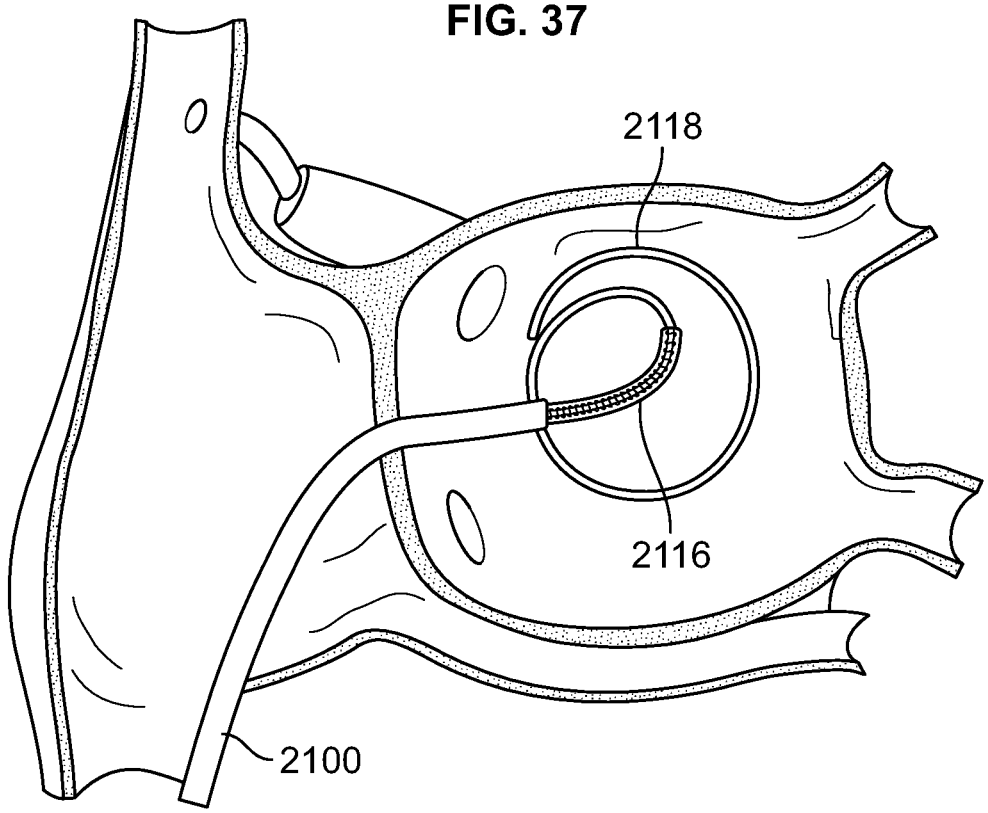

FIG. 38 shows the catheter 2116 deflected to aim towards the posterior wall of the left atrium. Energy element portion 2118 is manipulated to form a loop and urged against the posterior wall, overlapping with previously-formed right and left lesions.

Optionally, and not shown, guidewires can be advanced from the guide sheath and used to navigate the catheter treatment section into position.

The shape of the lesion and pattern may vary. In embodiments, and with reference to FIG. 39, a "box-shaped" lesion 900 is shown surrounding multiple pulmonary vein entries in a PVI procedure. The box-shaped lesion surrounds the pulmonary vein entries on both the left and right sides of the left atrium.

Figure 39:
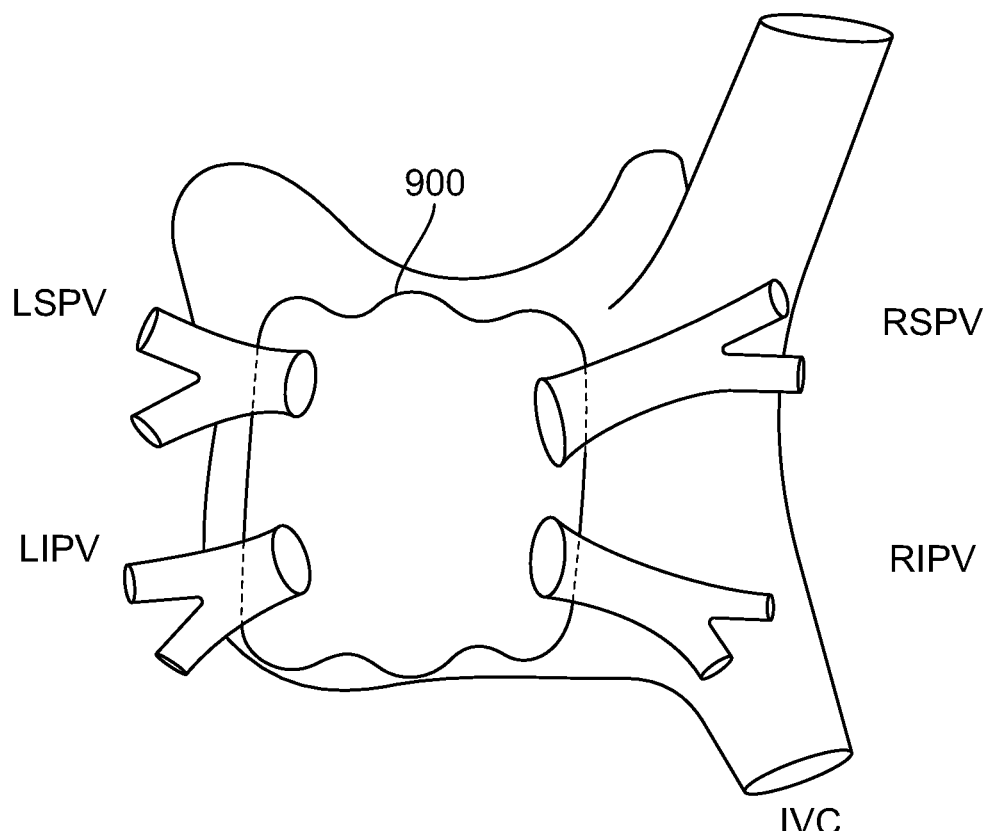
FIGS. 39-40 illustrate a method for creating a box-shaped lesion, according to an embodiment of the invention, where the figures depict the left atrium as viewed from the back of a patient.

The box-shaped lesion 900 may be formed in various ways. In some embodiments, the box-shaped lesion is formed by overlapping a combination of lesions, which can have similar or different shapes (e.g., oval, ellipse, ring, etc.) to form an overall larger continuous lesion, which may have a box-like shape 900 as shown in FIG. 39.

Figure 40:
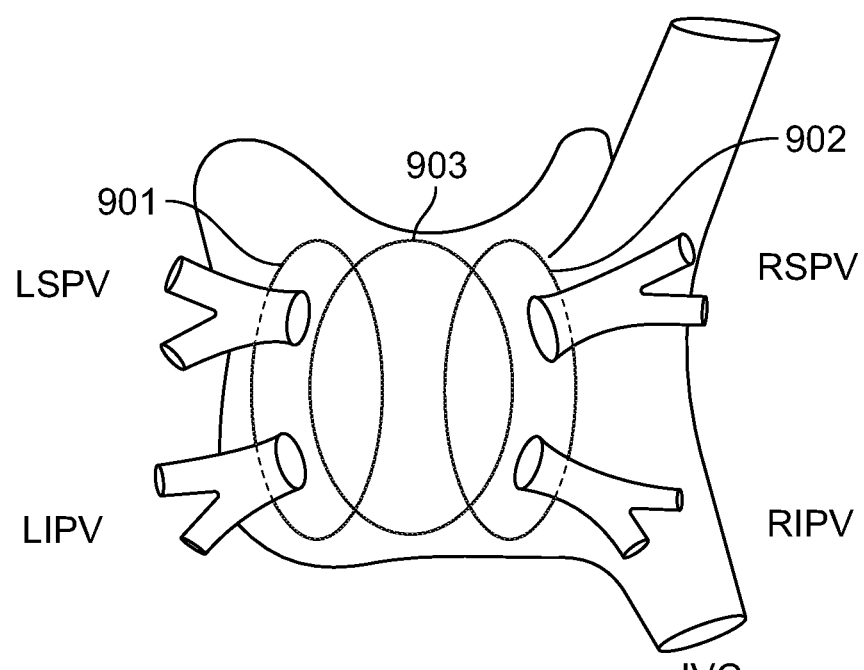
Figure 41:
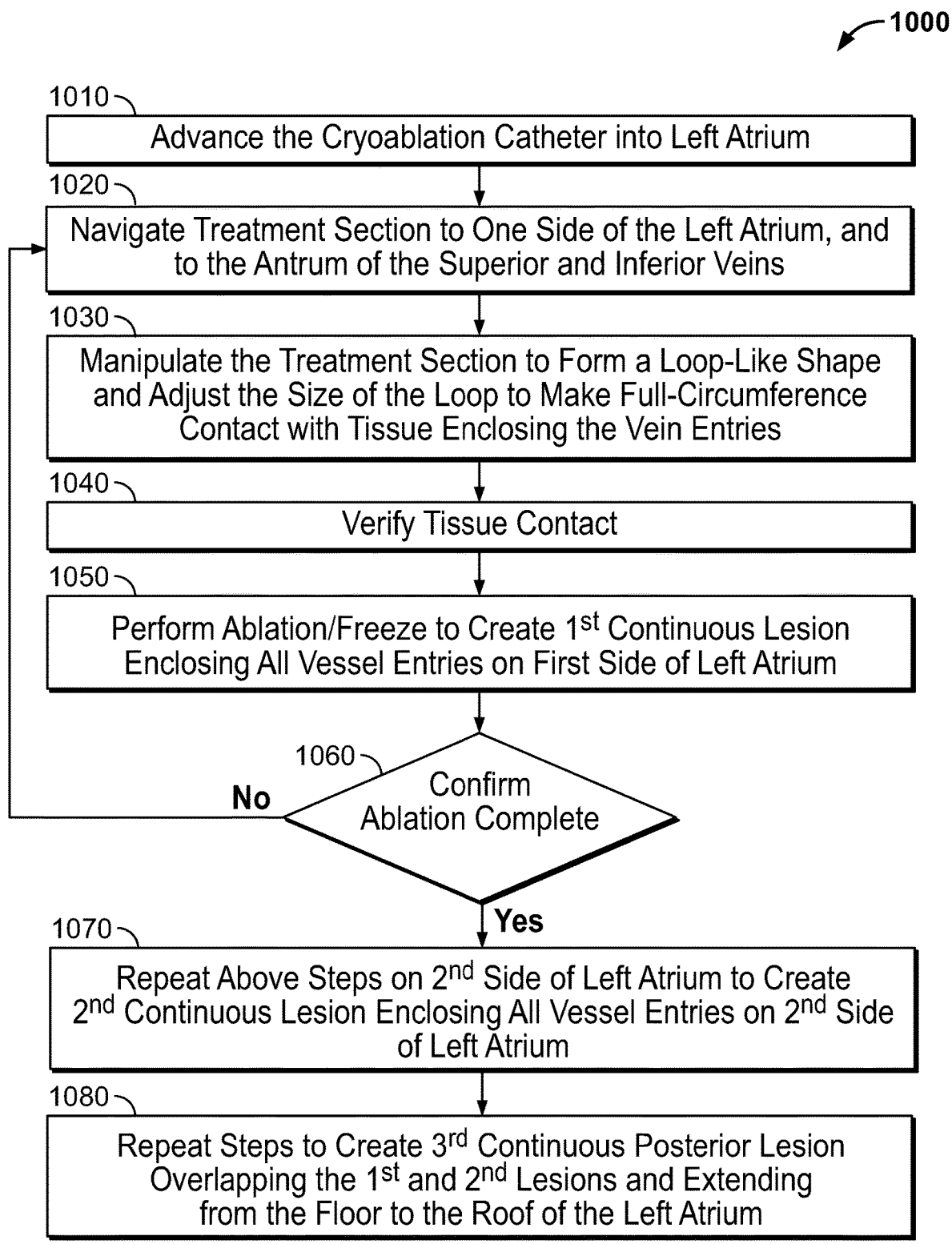
FIG. 41 is flow diagram showing a method of creating a box-shaped lesion to enclose multiple PVs in the left atrium, according to an embodiment of the invention.

With reference to the illustration shown in FIG. 40, and the corresponding flow diagram shown in FIG. 41, a method 1000 for forming a box-shaped lesion in the left atrium that encircles/encloses all pulmonary vein (RSPV, RIPV, LSPV and LIPV) entries, is described.

Step 1010 states to advance the cryoablation catheter into the left atrium, which can be performed using a guide sheath, for example.

Step 1020 states to navigate the treatment section (energy element portion 2118) of the catheter to one side of the left atrium and into the antrum of the superior and inferior pulmonary veins on that side of the atrium.

Step 1030 states to manipulate the treatment section (energy element portion 2118) of the catheter to form a loop-like shape and to adjust the size of the loop to make full circumference tissue contact with tissue to enclose the superior and inferior vein entries on that side of the atrium.

Step 1040 states to verify tissue contact. This step may be performed using, for example, electrodes mounted on the distal treatment section as disclosed and escribed in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes. The tissue electrocardiograms (ECGs) may be displayed using an EP recording system.

Optionally, an esophageal balloon (EBB) (as discussed above) is advanced into the esophagus in the vicinity of the heart. The EBB is inflated and a thermally conducting liquid is circulated through the balloon for the duration of the ablation treatment. As described herein, the EEB minimizes collateral damage to tissue adjacent the ablation zone by warming the tissue during the ablation cycle.

Step 1050 states to perform the ablation by freezing the tissue to create a first continuous lesion enclosing/surrounding the pulmonary vein entries on the first side of the left atrium, for example, the left side lesion 901 in FIG. 40. The duration of the tissue freeze may be up to 3 minutes or more, and generally ranges from about 1 to 3 minutes, and preferable is about 2 minutes. In embodiments, the freeze step comprises a single application of uninterrupted ablation energy.

In some embodiments, the duration of the energy application ranges from approximately 10 to 60 seconds, and sometimes is less than or equal to approximately 30 seconds.

The duration of the freeze cycle may vary. A physician or electro physiologist can elect to terminate the freeze cycle as desired (e.g., before or after the anticipated time period has passed). Examples of reasons for early termination include: a desire to reposition the catheter, a desire to improve catheter-tissue contact, or a safety concern.

Step 1060 states to confirm ablation is complete. Electrical activity from the electrodes on the distal treatment section may be monitored. During freezing, the electrocardiograms (ECG) will present abnormal signals due to freezing of the tissue and blood in contact with the freezing tip. After freezing is completed, however, the ECGs should not show any signal or evidence of a voltage potential in the tissue due to tissue necrosis.

If, however, the ECG signals/signatures reappear after the freezing step indicating that there is still electrical activity in the tissue, this is evidence that the ablation was not complete and that PVI may not have been achieved. In the event PVI was not achieved, the above described applicable steps can be repeated.

In some embodiments, another freeze in the same location can be commenced. Or, the catheter may be repositioned or otherwise adjusted to make better contact with the target tissue. Then, an additional freeze may be performed.

Performing an additional freeze can be beneficial especially if the distance between the pulmonary veins is unusually large. When the distance between the pulmonary veins is unusually large, isolating the pulmonary vein entries with only one continuous lesion is a challenge. In a sub population of patients with unusually enlarged hearts, forming an additional lesion around the pulmonary vein entries increases the likelihood of a complete and durable PVI.

Additionally, in some situations, it may be desirable to narrow the ablation loop to accommodate a single vein. In embodiments, the method comprises performing a single vein isolation around the ostium of the single vein. The diameter of the catheter loop is reduced from the relatively large size for isolating multiple veins to the applicable size of the single vein. In embodiments, the single vein isolation is performed subsequent to the larger multiple vein isolations.

Step 1070 states to repeat the applicable steps for the pulmonary veins on the other side of the left atrium. That is, for example, after the left vein antrum is isolated, the catheter loop will be navigated to the right vein antrum and all relevant steps should be repeated to create a second, right side lesion (e.g., lesion 902 of FIG. 40).

Step 1080 states to repeat the applicable above described steps for the posterior wall lesion (lesion 903 in FIG. 40). Once both the LSPV and LIPV antrum and the RSPV and RIPV vein antrum are isolated, the looped treatment section of the catheter is navigated to the posterior wall of the left atrium.

Optionally, the EBB is inflated in the esophagus and activated prior to ablation of the posterior wall. The other applicable steps for placing the left and right lesions are repeated for the posterior lesion. The posterior lesion 903 is more centrally located, and shown in FIG. 40 overlapping the left and right antrum lesions (901 and 902, respectively). Lesion 903 is also shown extending from the floor to the ceiling of the left atrium.

Although the method describes a particular order to create the left pulmonary vein, right pulmonary vein and posterior wall lesions, embodiments of the invention are not intended to be so limited except where specifically recited in the appended claims. The order that the lesions are created may vary. For example, in embodiments, the right side or posterior lesion may be performed prior to the left side lesion.

As can be seen in FIGS. 39 and 40, collectively, the plurality of independent lesions (901, 902, 903) form a composite box-like shaped continuous lesion 900 (FIG. 39) that encloses all the pulmonary vein entries on all sides (left, right, top and bottom) of the left atrium. In embodiments, the sum of the sub-lesions form an enclosure in the shape of a box, square, or rectangle. Performing the ablations to form this composite, continuous lesion 900 effectively electrically isolates all the pulmonary vein entries in the left atrium.

Figure 42:
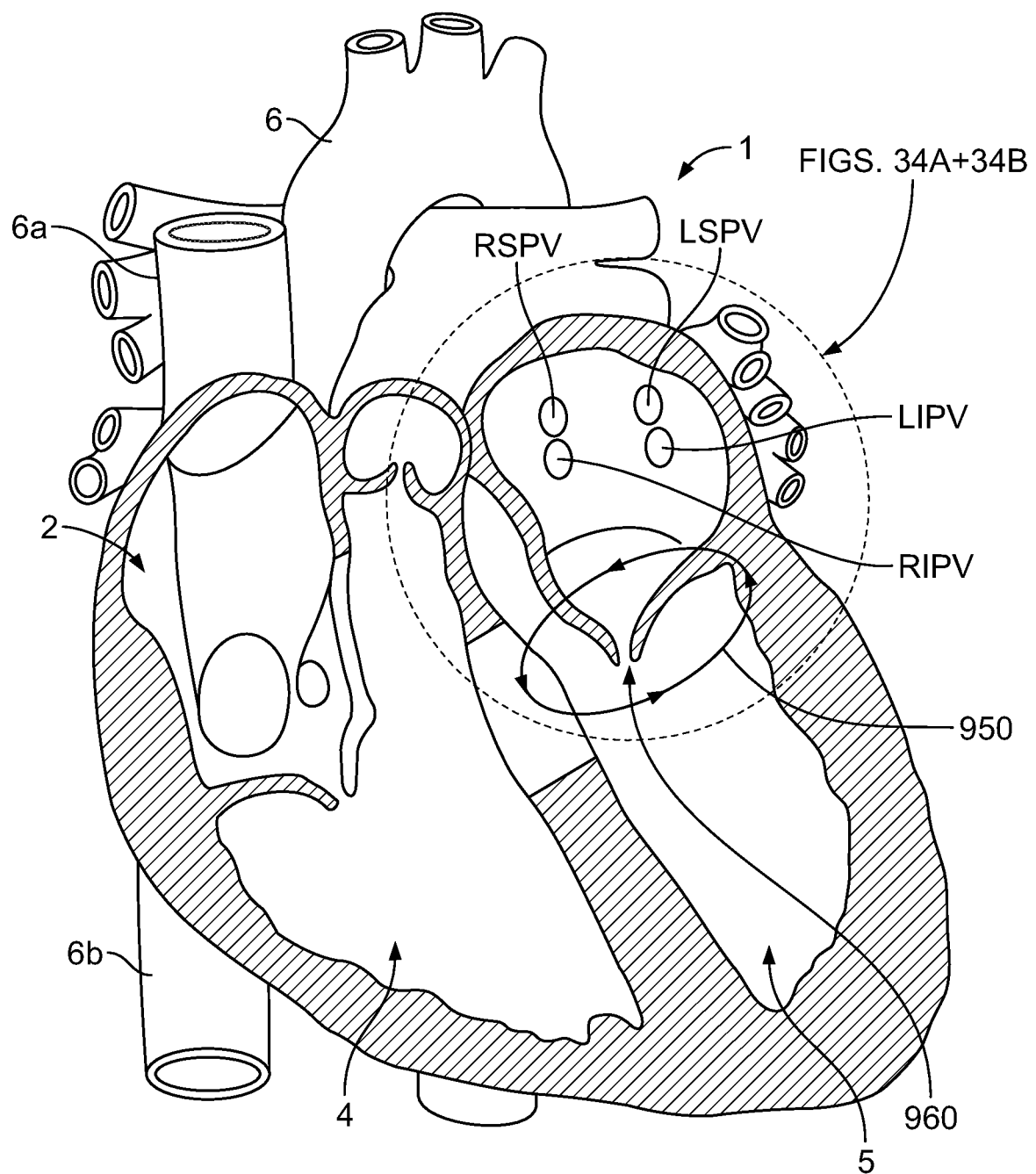
FIG. 42 is an illustration of a heart showing mitral valve electrical activity.
Figure 43A:
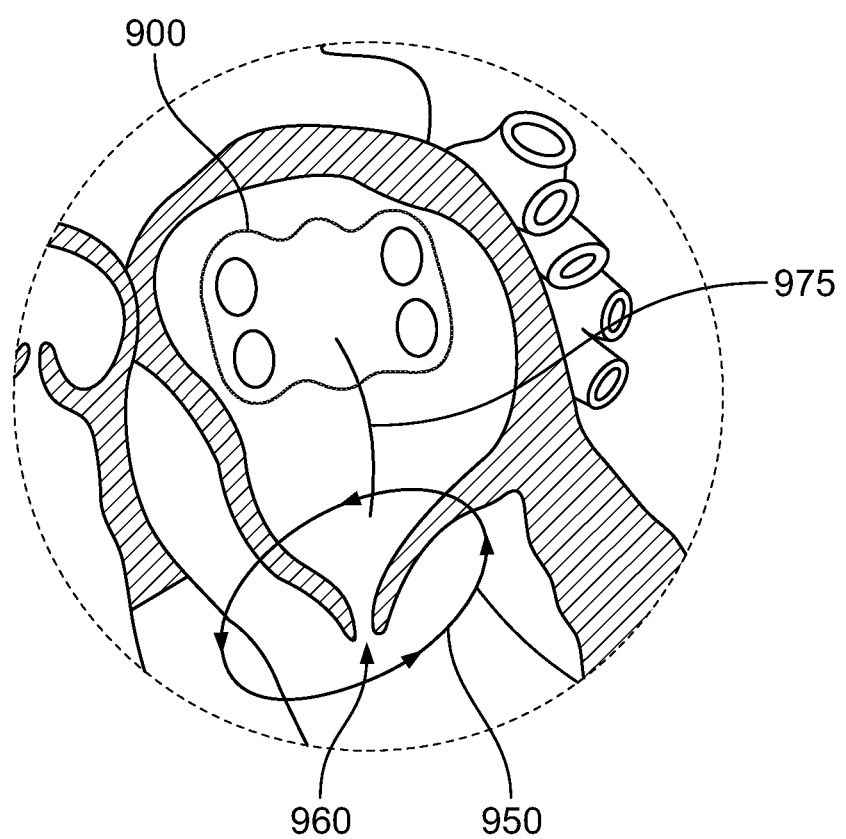
FIG. 43A depicts formation of a lesion to interrupt mitral valve electrical activity, according to an embodiment of the invention.
Figure 43B:
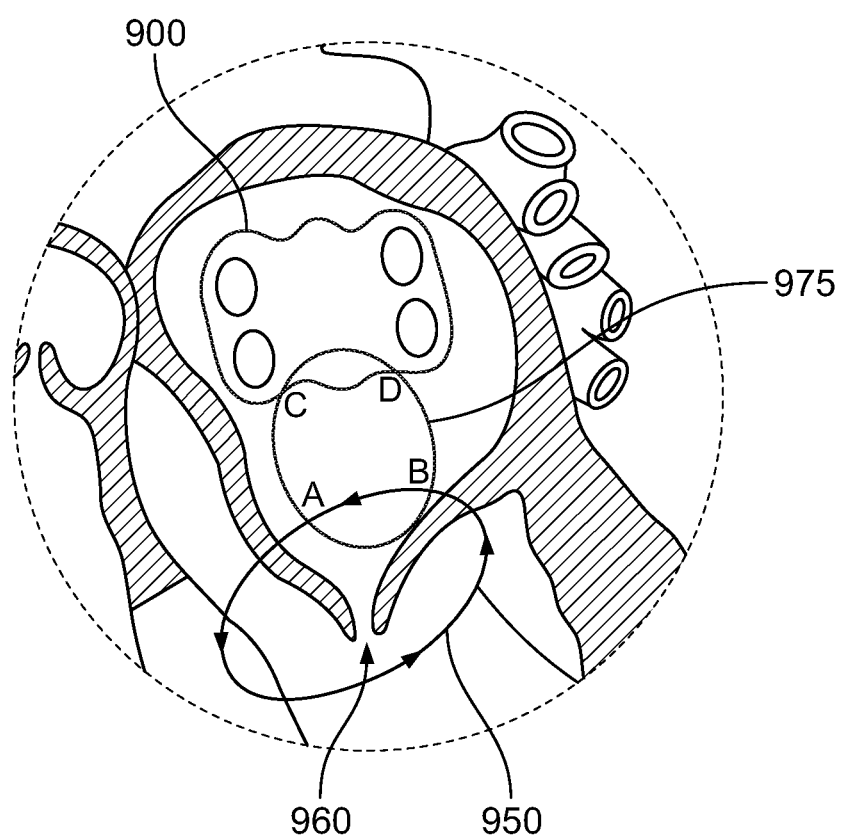
FIG. 43B depicts formation of a lesion to interrupt mitral valve electrical activity, according to an embodiment of the invention.

In patients that have atrial flutter in addition to paroxysmal atrial fibrillation and in patients that have non-paroxysmal atrial fibrillation, in addition to forming the lesions (901, 902, 903) discussed above with reference to FIGS. 39-41, it will be necessary to form an additional lesion to isolate the mitral valve. In these patients, as depicted in FIG. 42, there is electrical activity/current 950 that flows around the mitral valve 960. Therefore, the flow of this electrical activity/current 950, must be interrupted and stopped/prevented in order to treat these patients. Depicted in FIGS. 43A and 43B are embodiments of lesions that can be formed to interrupt the flow of current 950. As can be seen in the figures, this mitral lesion 975 connects to the box-like lesion 900 formed by the left pulmonary vein lesion 901, the right pulmonary vein lesion 902 and the posterior wall lesion 903.

As depicted in FIG. 43A, in one embodiment, the mitral lesion 975 extends from the vicinity of the mitral valve 960 (the mitral valve annulus) and intersects with the flow path of the current 950 and lesion 900. In this and other embodiments, it is important that the mitral lesion 975 at least intersects with the flow path of the current 950 and lesion 900. Therefore, the mitral lesion 975 can be formed at various locations within the left atrium as long as it intersects the flow path of the current 950 and connects to lesion 900. This type of lesion can be formed by modifying the shape of the treatment section of the catheter.

In the embodiment depicted in FIG. 43B, the same loop-like treatment section of the catheter used to create the left pulmonary vein lesion 901, the right pulmonary vein lesion 902 and the posterior wall lesion 903 can be used to create the mitral lesion 975. As can be seen in FIG. 43B, creating a loop-like or circular mitral lesion 975 cause the lesion 975 to intersect the flow path of the current 950 and lesion 900 at multiple points (A, B, C, D) thereby increasing the likelihood of a successful procedure.

Figure 44:
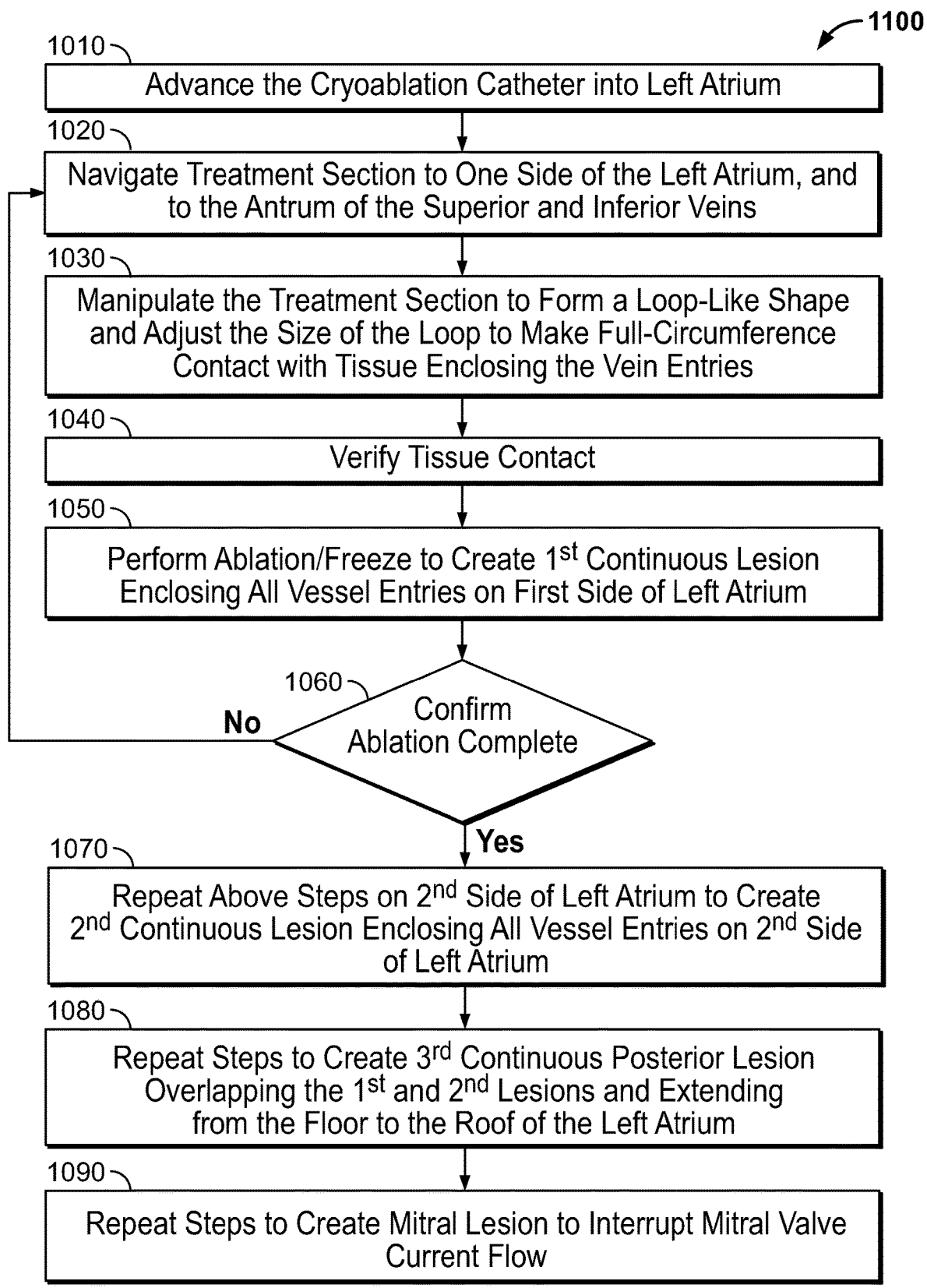
FIG. 44 is flow diagram showing a method of creating a box-shaped lesion to enclose multiple PVs in the left atrium and a lesion to interrupt mitral valve electrical activity, according to an embodiment of the invention.

If necessary, the mitral lesion 975 can be created after the box-like lesion 900 described above with respect to FIG. 41 is formed. A method 1100 for performing a procedure that includes forming the mitral lesion 975 as step 1090 after the box-like lesion 900 is formed is set forth in the flow diagram shown in FIG. 44. It will be readily apparent to those skilled in the art that the steps used in the procedure for forming the left pulmonary vein lesion 901, the right pulmonary vein lesion 902, the posterior wall lesion 903 and the mitral lesion 975 can be performed in any order as long as following the procedure, all the pulmonary vein entries are isolated and the flow path of current 950 is interrupted.

Figure 45:
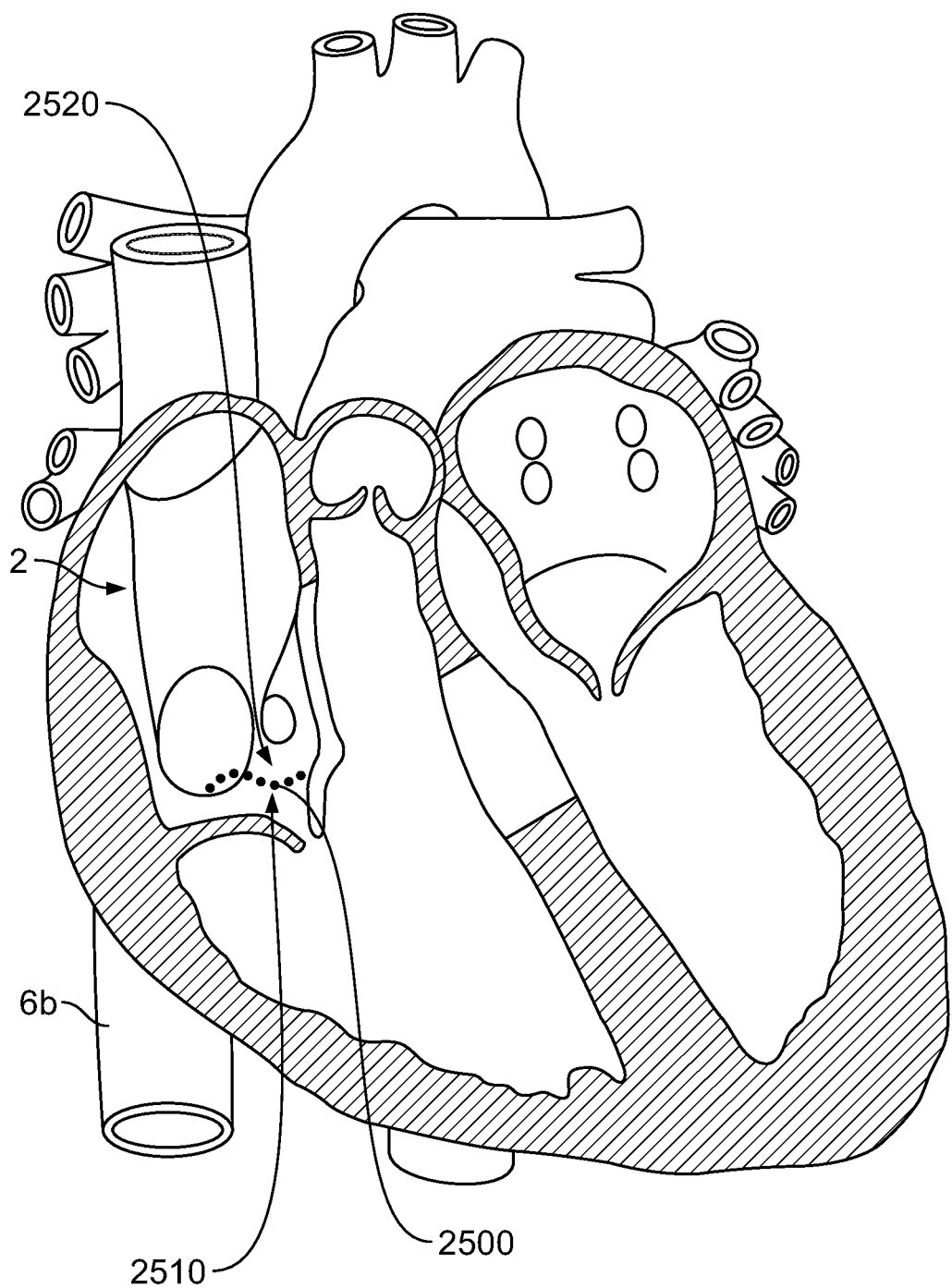
FIG. 45 depicts formation of a lesion to interrupt electrical activity in the right atrium, according to an embodiment of the invention.

In another embodiment, in some patients that suffer from persistent atrial fibrillation, a linear lesion in the right atrium 2 may be necessary. As depicted in FIG. 45, this linear lesion 2500 is created to connect the entrance of the Inferior Vena Cava (IVC) 6b and the annulus of the Tricuspid Valve (TV) 2510 and extends through the Cava Tricuspid Isthmus (CTI) 2520. This CTI lesion is used to prevent/interrupt the majority of potential re-entry circuits in the right atrium such as, for example, right atrial flutter and/or other arrhythmias that originate in the right atrium. This type of lesion is described in commonly assigned U.S. patent application Ser. No. 15/304,524, entitled "ENDOVASCULAR NEAR CRITICAL FLUID BASED CRYOABLATION CATHETER HAVING PLURALITY OF PREFORMED TREATMENT SHAPES," filed Oct. 15, 2016 by Alexei Babkin, et al., the contents of which is incorporated herein by reference in its entirety for all purposes.

In some embodiments, for certain patients, in addition to forming the lesions (901, 902, 903) discussed above with reference to FIGS. 39-41, it will be necessary to form the CTI lesion 2500 discussed above with reference to FIG. 45. It will be readily apparent to those skilled in the art that the steps used in the procedure for forming the left pulmonary vein lesion 901, the right pulmonary vein lesion 902, the posterior wall lesion 903 and the CTI lesion 2500 can be performed in any order as long as following the procedure, all the pulmonary vein entries are isolated and the majority of the potential re-entry circuits in the right atrium are interrupted/prevented.

In some embodiments, for certain patients, in addition to forming the lesions (901, 902, 903) discussed above with reference to FIGS. 39-41 and the mitral lesion 975 discussed above with reference to FIGS. 43A, 43B and 44, it will be necessary to form the CTI lesion 2500 discussed above with reference to FIG. 45. It will be readily apparent to those skilled in the art that the steps used in the procedure for forming the left pulmonary vein lesion 901, the right pulmonary vein lesion 902, the posterior wall lesion 903, the mitral lesion 975 and the CTI lesion 2500 can be performed in any order as long as following the procedure, all the pulmonary vein entries are isolated, the flow path of current 950 is interrupted and the majority of the potential re-entry circuits in the right atrium are interrupted/prevented.

Many modifications and variations of the present invention are possible in light of the above teachings. It is therefore to be understood that within the scope of the appended claims the invention may be practiced otherwise than as specifically described.

The invention claimed is:

1. An ablation apparatus for creating a lesion in target tissue,
the ablation apparatus comprising:
an ablation shaft comprising:
a handle;
a first portion;
an ablation portion;
distal tip;
at least one ablation energy delivery lumen;
at least one ablation energy return lumen; and
a stylet lumen that extends substantially along a length of the ablation shaft from the handle to at least the ablation portion; and
a set of different types of stylets, each type of stylet capable of being inserted into and withdrawn from the stylet lumen, each type of stylet comprising (a) a shape-memory material, (b) a unique pre-set shape, and (c) a unique austenite finish transformation temperature such that the stylet's degree of expansion during cooling is predictably controlled to assume the unique pre-set shape, and
wherein the austenite finish transformation temperature of at least one type of stylet is less than 0 degrees Celsius.

2. The ablation apparatus of claim 1, wherein the at least one ablation energy delivery lumen and the at least one ablation energy return lumen comprise an inner tube having an outer tube surrounding the inner tube thereby defining a gap between the inner tube and the outer tube.

3. The ablation apparatus of claim 2, further comprising a thermally conducting media, and wherein the gap is filled with the thermally conducting media.

4. The ablation apparatus of claim 1, wherein the ablation energy is provided by a cryogen.

5. The ablation apparatus of claim 4, wherein the cryogen is nitrogen.

6. The ablation apparatus of claim 5, wherein the nitrogen is near critical nitrogen.

7. The ablation apparatus of claim 1, wherein the shape-memory material is Nitinol.

8. The ablation apparatus of claim 1,
wherein the stylet has a plurality of flexibilities along its length.

9. The ablation apparatus of claim 8, wherein the plurality of flexibilities are due to mechanical alterations to the stylet.

10. The ablation apparatus of claim 8, wherein the ablation energy is provided by nitrogen.

11. The ablation apparatus of claim 8, wherein the shape-memory material is Nitinol.

12. The ablation apparatus of claim 8, wherein at least a distal portion of the stylet is pre-set with a shape that corresponds to a desired shape of the lesion to be formed.

13. The ablation apparatus of claim 1, wherein the at least one ablation energy delivery lumen and return lumen comprise a plurality of ablation energy delivery lumens and ablation energy return lumens arranged alternatingly in an annular configuration about the stylet lumen, thereby providing contiguous uniform cooling along the entire circumference and length of the ablation portion regardless of different shapes imposed on the ablation portion arising from different types of stylets advanced into the ablation shaft.

14. A cryoablation catheter for creating a lesion in target tissue,
the cryoablation catheter comprising:
an ablation shaft comprising:
a handle;
a freezing portion;
a non-freezing portion;
a plurality of cryogen delivery tubes, wherein each cryogen
delivery tube comprises an inner tube having an outer tube surrounding the inner tube thereby defining a gap between the inner tube and the outer tube;
a plurality of cryogen return tubes, wherein each cryogen return tube comprises an inner tube having an outer tube surrounding the inner tube thereby defining a gap between the inner tube and the outer tube;
a plurality of electrodes on an exterior surface of the freezing portion;
at least one service lumen; and
a stylet lumen that extends substantially along a length of the ablation shaft from the handle to the non-freezing portion;
a first stylet advanceable into and withdrawable from the stylet lumen, the first stylet comprising a shape-memory material and having a distal portion that is pre-set with a first shape that corresponds to (i) a desired shape of the lesion to be formed and (ii) a shape of a diagnostic portion to be received within a pulmonary vein entry,
wherein the first stylet has an austenite finish transformation temperature such that the first stylet does not expand during freezing thereby maintaining the pre-set shape; and
wherein the austenite finish transformation temperature is less than 0 degrees Celsius;
wherein the diagnostic portion of the stylet corresponds to the distal non-freezing portion of the ablation shaft; and
a second stylet advanceable into and withdrawable from the stylet lumen, the second stylet having a distal portion that is pre-set with a second shape different than the first shape of the first stylet, and wherein the difference between the first shape and second shape is based on programming a difference in the austenite finish transformation temperature between the first stylet and the second stylet.

15. The cryoablation catheter of claim 14, wherein the plurality of cryogen delivery tubes and return tubes are arranged in a single layer annular configuration about the stylet lumen.

16. The cryoablation catheter of claim 15, wherein the diagnostic portion has a coiled shape.

* * * * *